(12) United States Patent
Dietz et al.

(10) Patent No.: US 11,692,028 B2
(45) Date of Patent: Jul. 4, 2023

(54) MAP KINASE PATHWAY TARGETS FOR THE TREATMENT OF MARFAN SYNDROME

(71) Applicant: The Johns Hopkins University, Baltimore, MD (US)

(72) Inventors: Harry C. Dietz, Towson, MD (US); Jefferson J. Doyle, Baltimore, MD (US); Alexander J. Doyle, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/490,546

(22) PCT Filed: Mar. 2, 2018

(86) PCT No.: PCT/US2018/020692
§ 371 (c)(1),
(2) Date: Feb. 21, 2020

(87) PCT Pub. No.: WO2018/160987
PCT Pub. Date: Sep. 7, 2018

(65) Prior Publication Data
US 2020/0247881 A1 Aug. 6, 2020

Related U.S. Application Data

(60) Provisional application No. 62/466,197, filed on Mar. 2, 2017.

(51) Int. Cl.
*A61K 31/517* (2006.01)
*C07K 16/28* (2006.01)
(Continued)

(52) U.S. Cl.
CPC .............. *C07K 16/22* (2013.01); *A61P 25/00* (2018.01); *C07D 239/94* (2013.01); *C07K 16/28* (2013.01); *A61K 31/517* (2013.01)

(58) Field of Classification Search
CPC ........... A61P 25/00; A61P 9/00; A61K 31/517
(Continued)

(56) References Cited

U.S. PATENT DOCUMENTS

| 8,883,473 | B2 | 11/2014 | Leonard et al. |
| 2010/0034806 | A1 | 2/2010 | Dietz et al. |
| 2010/0209923 | A1 | 8/2010 | Niikawa et al. |

FOREIGN PATENT DOCUMENTS

WO 2014/037316 A1 3/2014

OTHER PUBLICATIONS

Doyle "Elucidation of the pathogenesis of TGF-beta-vasculopathies identifies novel therapeutic strategies," A dissertation submitted to John Hopkins University, 2015.https://jscholarship.library.jhu.edU/bitstream/handle/1774.2/60604/DOYLE-DISSERTATION-2015.pdf?sequence=1&isAllowed=y#page=148 (Year: 2015).*
(Continued)

*Primary Examiner* — Shengjun Wang
(74) *Attorney, Agent, or Firm* — Fox Rothschild LLP

(57) ABSTRACT

The instant disclosure provides methods and compositions for the diagnosis, treatment and prevention of Marfan syndrome and related diseases, disorders and conditions. The disclosure further provides pharmaceutical compositions and kits for the diagnosis, treatment and prevention of Marfan syndrome and related diseases, disorders and conditions.

7 Claims, 21 Drawing Sheets

Specification includes a Sequence Listing.

(51) Int. Cl.
 C07K 16/22 (2006.01)
 A61P 25/00 (2006.01)
 C07D 239/94 (2006.01)
(58) Field of Classification Search
 USPC .................................................... 514/266.4
 See application file for complete search history.

(56) References Cited

OTHER PUBLICATIONS

Obama et al. "Epidermal growth factor receptor inhibitor protect against abdominal aortic aneurysm in an mouse model," Clinical Sciences, 2015, vol. 128, No. 9, pp. 559-565 (Year: 2015).*
Takayama et al. "True abdominal aortic aneurysm in Marfan syndrome," J. Vascular Surgery, 2008, vol. 49, No. 5, pp. 1162-1165. (Year: 2008).*
Paye, Alexandra, et al. "EGFR activation and signaling in cancer cells are enhanced by the membrane-bound metalloprotease MT4-MMP." Cancer research 74.23 (2014): 6758-6770.
Pearson, Gray, et al. "Mitogen-activated protein (MAP) kinase pathways: regulation and physiological functions." Endocrine reviews 22.2 (2001): 153-183.
Pyeritz, Reed E., and Victor A. McKusick. "The Marfan syndrome: diagnosis and management." New England Journal of Medicine 300.14 (1979): 772-777.
Rajakulendran, Thanashan, et al. "A dimerization-dependent mechanism drives RAF catalytic activation." Nature 461.7263 (2009): 542.
Regan, Christopher P., et al. "Erk5 null mice display multiple extraembryonic vascular and embryonic cardiovascular defects." Proceedings of the National Academy of Sciences 99.14 (2002): 9248-9253.
Reményi, Attila, et al. "The role of docking interactions in mediating signaling input, output, and discrimination in the yeast MAPK network." Molecular cell 20.6 (2005): 951-962.
Sheridan, Douglas L., et al. "Substrate discrimination among mitogen-activated protein kinases through distinct docking sequence motifs" Journal of Biological Chemistry 283.28 (2008): 19511-19520.
Takekawa, Mutsuhiro, Francesc Posas, and Haruo Saito. "A human homolog of the yeast Ssk2/Ssk22 MAP kinase kinase kinases, MTK1, mediates stress?induced activation of the p38 and JNK pathways." The EMBO Journal 16.16 (1997): 4973-4982.
Theodosiou, Aspasia, and Alan Ashworth. "MAP kinase phosphatases." Genome biology 3.7 (2002): reviews3009-1.
Uchiyama-Tanaka, Yoko, et al. "Involvement of HB-EGF and EGF receptor transactivation in TGF-?-mediated fibronectin expression in mesangial cells " Kidney international 62.3 (2002): 799-808.
Viñals, Francesc, and Jacques Pouysségur. "Transforming growth factor ?1 (TGF-?1) promotes endothelial cell survival during in vitro angiogenesis via an autocrine mechanism implicating TGF-? signaling." Molecular and Cellular Biology 21.21 (2001): 7218-7230.
Wahl, Geoffrey M., Shelby L. Barger, and Alan R. Kimmel. "[43] Molecular hybridization of immobilized nucleic acids: Theoretical concepts and practical considerations." Methods in enzymology. vol. 152. Academic Press, 1987. 399-407.
Wang, Chunmao, et al. "Angiotensin II increases matrix metalloproteinase 2 expression in human aortic smooth muscle cells via AT1R and ERK1/2." Experimental Biology and Medicine 240.12 (2015): 1564-1571.
Warshamana, G. Sakuntala, et al. "Susceptibility to asbestos-induced and transforming growth factor-?1-induced fibroproliferative lung disease in two strains of mice." American journal of respiratory cell and molecular biology 27.6 (2002): 705-713.
Wolfsberg, Tyra G. "Using the NCBI map viewer to browse genomic sequence data." Current protocols in bioinformatics 29.1 (2010): 1-5.
Wood, J. R., et al. "Pulmonary disease in patients with Marfan syndrome." Thorax 39.10 (1984): 780-784.

Xiong, Wanfen, et al. "MMP-2 regulates Erk1/2 phosphorylation and aortic dilatation in Marfan syndrome." Circulation research 110.12 (2012): e92-e101.
Yan, Wu, et al. "The hydrophobic domains in the carboxyl-terminal signal for GPI modification and in the amino-terminal leader peptide have similar structural requirements." Journal of molecular biology 275.1 (1998): 25-33.
International Search Report dated Jul. 12, 2018 in corresponding International Application No. PCT/US2018/020692 (7 pages).
Written Opinion dated Jul. 12, 2018 in corresponding International Application No. PCT/US2018/020692 (9 pages).
Bardwell, A. Jane, Erlynn Frankson, and Lee Bardwell. "Selectivity of docking sites in MAPK kinases." Journal of Biological Chemistry 284.19 (2009): 13165-13173.
Benton, W. David, and Ronald W. Davis. "Screening lambdagt recombinant clones by hybridization to single plaques in situ." Science 196.4286 (1977): 180-182.
Bourdeau, Annie, et al. "Potential role of modifier genes influencing transforming growth factor-?1 levels in the development of vascular defects in endoglin heterozygous mice with hereditary hemorrhagic telangiectasia." The American journal of pathology 158.6 (2001): 2011-2020.
Brooke, Benjamin S., et al. "Angiotensin II blockade and aortic-root dilation in Marfan's syndrome." New England Journal of Medicine 358.26 (2008): 2787-2795.
Burkhard, Kimberly, and Paul Shapiro. "Use of inhibitors in the study of MAP kinases." MAP Kinase Signaling Protocols. Humana Press, Totowa, NJ, 2010. 107-122.
Cargnello, Marie, and Philippe P. Roux "Activation and function of the MAPKs and their substrates, the MAPK-activated protein kinases." Microbiol. Mol. Biol. Rev. 75.1 (2011): 50-83.
Carta, Luca, et al. "p38 MAPK is an early determinant of promiscuous Smad2/3 signaling in the aortas of fibrillin-1 (Fbn1)-null mice." Journal of Biological Chemistry 284.9 (2009): 5630-5636.
Cohn, Ronald D., et al. "Angiotensin II type 1 receptor blockade attenuates TGF-?-induced failure of muscle regeneration in multiple myopathic states." Nature medicine 13.2 (2007): 204.
Coulombe, Phillipe, and Sylvain Meloche. "Atypical mitogen-activated protein kinases: structure, regulation and functions." Biochimica et Biophysica Acta (BBA)—Molecular Cell Research 1773.8 (2007): 1376-1387.
Cussac, Daniel, et al. "?2B-Adrenergic receptor activates MAPK via a pathway involving arachidonic acid metabolism, matrix metalloproteinases, and epidermal growth factor receptor transactivation." Journal of Biological Chemistry 277.22 (2002): 19882-19888.
Dietz, Harry C. "New therapeutic approaches to mendelian disorders." New England Journal of Medicine 363.9 (2010): 852-863.
Dietz, Harry. "Marfan syndrome." GeneReviews®[Internet], University of Washington, Seattle, 2017.
Doyle, Alexander J., et al. "Mutations in the TGF-? repressor SKI cause Shprintzen-Goldberg syndrome with aortic aneurysm." Nature genetics 44.11 (2012): 1249.
Doyle, Jefferson J., et al. "A deleterious gene-by-environment interaction imposed by calcium channel blockers in Marfan syndrome." Elife 4 (2015): e08648.
Du, Yan, et al. "Cdc42 induces activation loop phosphorylation and membrane targeting of mixed lineage kinase 3." Journal of Biological Chemistry 280.52 (2005): 42984-42993.
Déléris, Paul, et al. "Activation loop phosphorylation of ERK3/ERK4 by group I p21-activated kinases (PAKs) defines a novel PAK-ERK3/4-MAPK-activated protein kinase 5 signaling pathway." Journal of Biological Chemistry 286.8 (2011): 6470-6478.
Galian, Carmen, et al. "Efficient glycosylphosphatidylinositol (GPI) modification of membrane proteins requires a C-terminal anchoring signal of marginal hydrophobicity." Journal of Biological Chemistry 287.20 (2012): 16399-16409.
Gallo, Elena M., et al. "Angiotensin II-dependent TGF-? signaling contributes to Loeys-Dietz syndrome vascular pathogenesis." The Journal of clinical investigation 124.1 (2014): 448-460.
Garai, Ágnes, et al. "Specificity of linear motifs that bind to a common mitogen-activated protein kinase docking groove." Sci. Signal. 5.245 (2012): ra74-ra74.

(56) References Cited

OTHER PUBLICATIONS

Glatz, Gábor, et al. "Structural mechanism for the specific assembly and activation of the extracellular signal regulated kinase 5 (ERK5) module." Journal of Biological Chemistry 288.12 (2013): 8596-8609.

Goldsmith, Elizabeth J. "Three-dimensional docking in the MAPK p38?." Sci. Signal. 4.204 (2011): p. e47-p. e47.

Grunstein, Michael, and David S. Hogness. "Colony hybridization: a method for the isolation of cloned DNAs that contain a specific gene." Proceedings of the National Academy of Sciences 72.10 (1975): 3961-3965.

Habashi, Jennifer P., et al. "Angiotensin II type 2 receptor signaling attenuates aortic aneurysm in mice through ERK antagonism." Science 332.6027 (2011): 361-365.

Habashi, Jennifer P., et al. "Losartan, an AT1 antagonist, prevents aortic aneurysm in a mouse model of Marfan syndrome." Science 312.5770 (2006): 117-121.

Hall, John R., et al. "Pneumothorax in the Marfan syndrome: prevalence and therapy." The Annals of thoracic surgery 37.6 (1984): 500-504.

Han, Jiahuai, et al. "Characterization of the structure and function of a novel MAP kinase kinase (MKK6)." Journal of Biological Chemistry 271.6 (1996): 2886-2891.

Hayashi, Masaaki, and Jiing-Dwan Lee. "Role of the BMK1/ERK5 signaling pathway: lessons from knockout mice." Journal of Molecular Medicine 82.12 (2004): 800-808.

Higuchi, Sadaharu, et al. "Angiotensin II signal transduction through the AT1 receptor: novel insights into mechanisms and pathophysiology." Clinical science 112.8 (2007): 417-428.

Holm, Tammy M., et al. "Noncanonical TGF? signaling contributes to aortic aneurysm progression in Marfan syndrome mice." Science 332.6027 (2011): 358-361.

Huang, Zhonghui, Bo Zhou, and Zhong-Yin Zhang. "Molecular determinants of substrate recognition in hematopoietic protein-tyrosine phosphatase." Journal of Biological Chemistry 279.50 (2004): 52150-52159.

Judge, Daniel P., et al. "Evidence for a critical contribution of haploinsufficiency in the complex pathogenesis of Marfan syndrome." The Journal of clinical investigation 114.2 (2004): 172-181.

Kim, Do-Hee, and Taebo Sim. "Novel small molecule Raf kinase inhibitors for targeted cancer therapeutics." Archives of pharmacal research 35.4 (2012): 605-615.

Kimmel, Alan R. "[54] Identification and characterization of specific clones: Strategy for confirming the validity of presumptive clones." Methods in enzymology. vol. 152. Academic Press, 1987. 507-511.

Lacro, Ronald V., et al. "Atenolol versus losartan in children and young adults with Marfan's syndrome." New England Journal of Medicine 371.22 (2014): 2061-2071.

Laws, Nicola, and Andrew Hoey. "Progression of kyphosis in mdx mice." Journal of Applied Physiology 97.5 (2004): 1970-1977.

Li, Heng, Jue Ruan, and Richard Durbin. "Mapping short DNA sequencing reads and calling variants using mapping quality scores." Genome research 18.11 (2008): 1851-1858.

Li, Ruiqiang, et al. "SOAP: short oligonucleotide alignment program." Bioinformatics 24.5 (2008): 713-714.

Lindsay, Mark E., et al. "Loss-of-function mutations in TGFB2 cause a syndromic presentation of thoracic aortic aneurysm." Nature genetics 44.8 (2012): 922.

Loeys, Bart L., et al. "The revised Ghent nosology for the Marfan syndrome." Journal of medical genetics 47.7 (2010): 476-485.

Loeys, Bart L., Geert Mortier, and Harry C. Dietz. "Bone lessons from Marfan syndrome and related disorders: fibrillin, TGF-B and BMP at the balance of too long and too short." Pediatric endocrinology reviews: PER 10 (2013): 417-423.

Manning, Gerard, et al. "The protein kinase complement of the human genome." Science 298.5600 (2002): 1912-1934.

Martin-Alonso, Mara, et al. "Deficiency of MMP17/MT4-MMP proteolytic activity predisposes to aortic aneurysm in mice." Circulation research 117.2 (2015): e13-e26.

Massagué, Joan, Stacy W. Blain, and Rogers. Lo. "TGF? signaling in growth control, cancer, and heritable disorders." Cell 103.2 (2000): 295-309.

Matsuda, Yasunobu, and Manabu Fukumoto. "Sorafenib: complexities of Raf-dependent and Raf-independent signaling are now unveiled." Medical molecular morphology 44.4 (2011): 183-189.

Mehta, Puja K., and Kathy K. Griendling. "Angiotensin II cell signaling: physiological and pathological effects in the cardiovascular system." American Journal of Physiology-Cell Physiology 292.1 (2007): C82-C97.

Miyake, Zenshi, et al. "Activation of MTK1/MEKK4 by GADD45 through induced NC dissociation and dimerization-mediated trans autophosphorylation of the MTK1 kinase domain." Molecular and cellular biology 27.7 (2007): 2765-2776.

Murdoch, J. Lamont, et al. "Life expectancy and causes of death in the Marfan syndrome." New England Journal of Medicine 286.15 (1972): 804-808.

Nakamura, Kazuhiro, and Gary L. Johnson. "PB1 domains of MEKK2 and MEKK3 interact with the MEK5 PB1 domain tor activation of the ERK5 pathway." Journal of Biological Chemistry 278.39 (2003): 36989-36992.

Neptune, Enid R., et al. "Dysregulation of TGF-? activation contributes to pathogenesis in Marfan syndrome." Nature genetics 33.3 (2003): 407.

Ng, Connie M., et al. "TGF-?-dependent pathogenesis of mitral valve prolapse in a mouse model of Marfan syndrome." The Journal of clinical investigation 114.11 (2004): 1586-1592.

* cited by examiner

Mus musculus: C57BL6/J Strain (SEQ ID NO: 24)

DNA     ACTTCAGACGCACACAGGTTGGCACTGCCATCTCTGCTGCTTCTGACTCCA
Protein  -T--S--D--A--H--R--L--A--L--P--S--L--L--L--L--T--P-
DNA     CTGCTGTGGGGCCTGTGA
Protein  -L--L--W--G--L--*-

Mus musculus: 129S6/SvEvTac Strain (SEQ ID NO: 25)

DNA     ACTTCAGACGCACACAGGTTGGCACTGCCATCTCTGCTGCTTCTGACTCCA
Protein  -T--S--D--A--H--R--L--A--L--P--S--L--L--L--L--T--P-
DNA     CTGCTGTGGGGCCTGTGGACCTCAGTCTCTGCCAAGGCATCCTGA
Protein  -L--L--W--G--L--W--T--S--V--S--A--K--A--S--*-

Homo Sapiens (SEQ ID NO: 26)

DNA     CCGGGGGCCCCAGGCCCACTGGTGGCTGCCACCATGCTGCTGCTGCTGCCG
Protein  -P--G--A--P--G--P--L--V--A--A--T--M--L--L--L--L--P-
DNA     CCACTGTCACCAGGCGCCCTGTGGACAGCGGCCCAGGCCCTGACGCTATGA
Protein  -P--L--S--P--G--A--L--W--T--A--A--Q--A--L--T--L--*-

FIGURE 11

SEQUENCE LISTING

<160> NUMBER OF SEQ ID NOS: 29

<210> SEQ ID NO 1
<211> LENGTH: 603
<212> TYPE: PRT
<213> ORGANISM: Homo sapiens

<400> SEQUENCE: 1

```
Met Arg Arg Arg Ala Ala Arg Gly Pro Gly Pro Pro Pro Gly Pro
1               5                   10                  15

Gly Leu Ser Arg Leu Pro Leu Pro Leu Leu Leu Leu Ala Leu Gly
                20                  25                  30

Thr Arg Gly Gly Cys Ala Ala Pro Ala Pro Ala Arg Ala Glu Asp
                35                  40                  45

Leu Ser Leu Gly Val Glu Trp Leu Ser Arg Phe Gly Tyr Leu Pro
50                  55                  60

Ala Asp Pro Thr Thr Gly Gln Leu Gln Thr Gln Glu Glu Leu Ser Lys
65                  70                  75                  80

Ala Ile Thr Ala Met Gln Gln Phe Gly Gly Leu Glu Ala Thr Gly Ile
                85                  90                  95

Leu Asp Glu Ala Thr Leu Ala Leu Met Lys Thr Pro Arg Cys Ser Leu
                100                 105                 110

Pro Asp Leu Pro Val Leu Thr Gln Ala Arg Arg Arg Gln Ala Pro
                115                 120                 125

Ala Pro Thr Lys Trp Asn Lys Arg Asn Leu Ser Trp Arg Val Arg Thr
                130                 135                 140

Phe Pro Arg Asp Ser Pro Leu Gly His Asp Thr Val Arg Ala Leu Met
145                 150                 155                 160

Tyr Tyr Ala Leu Lys Val Trp Ser Asp Ile Ala Pro Leu Asn Phe His
                165                 170                 175

Glu Val Ala Gly Ser Ala Ala Asp Ile Gln Ile Asp Phe Ser Lys Ala
                180                 185                 190

Asp His Asn Asp Gly Tyr Pro Phe Asp Gly Pro Gly Gly Thr Val Ala
                195                 200                 205

His Ala Phe Phe Pro Gly His His Thr Ala Gly Asp Thr His Phe
                210                 215                 220

Asp Asp Asp Glu Ala Trp Thr Phe Arg Ser Ser Asp Ala His Gly Met
225                 230                 235                 240

Asp Leu Phe Ala Val Ala Val His Glu Phe Gly His Ala Ile Gly Leu
                245                 250                 255

Ser His Val Ala Ala His Ser Ile Met Arg Pro Tyr Tyr Gln Gly
                260                 265                 270

Pro Val Gly Asp Pro Leu Arg Tyr Gly Leu Pro Tyr Glu Asp Lys Val
                275                 280                 285

Arg Val Trp Gln Leu Tyr Gly Val Arg Glu Ser Val Ser Pro Thr Ala
                290                 295                 300

Gln Pro Glu Glu Pro Pro Leu Leu Pro Glu Pro Pro Asp Asn Arg Ser
305                 310                 315                 320

Ser Ala Pro Pro Arg Lys Asp Val Pro His Arg Cys Ser Thr His Phe
                325                 330                 335

Asp Ala Val Ala Gln Ile Arg Gly Glu Ala Phe Phe Lys Gly Lys
                340                 345                 350

Tyr Phe Trp Arg Leu Thr Arg Asp Arg His Leu Val Ser Leu Gln Pro
                355                 360                 365
```

Ala Gln Met His Arg Phe Trp Arg Gly Leu Pro Leu His Leu Asp Ser
    370                 375                 380

Val Asp Ala Val Tyr Glu Arg Thr Ser Asp His Lys Ile Val Phe Phe
385                 390                 395                 400

Lys Gly Asp Arg Tyr Trp Val Phe Lys Asp Asn Asn Val Glu Glu Gly
                405                 410                 415

Tyr Pro Arg Pro Val Ser Asp Phe Ser Leu Pro Pro Gly Gly Ile Asp
                420                 425                 430

Ala Ala Phe Ser Trp Ala His Asn Asp Arg Thr Tyr Phe Phe Lys Asp
            435                 440                 445

Gln Leu Tyr Trp Arg Tyr Asp Asp His Thr Arg His Met Asp Pro Gly
    450                 455                 460

Tyr Pro Ala Gln Ser Pro Leu Trp Arg Gly Val Pro Ser Thr Leu Asp
465                 470                 475                 480

Asp Ala Met Arg Trp Ser Asp Gly Ala Ser Tyr Phe Phe Arg Gly Gln
                485                 490                 495

Glu Tyr Trp Lys Val Leu Asp Gly Glu Leu Glu Val Ala Pro Gly Tyr
                500                 505                 510

Pro Gln Ser Thr Ala Arg Asp Trp Leu Val Cys Gly Asp Ser Gln Ala
            515                 520                 525

Asp Gly Ser Val Ala Ala Gly Val Asp Ala Ala Glu Gly Pro Arg Ala
    530                 535                 540

Pro Pro Gly Gln His Asp Gln Ser Arg Ser Glu Asp Gly Tyr Glu Val
545                 550                 555                 560

Cys Ser Cys Thr Ser Gly Ala Ser Ser Pro Gly Ala Pro Gly Pro
                565                 570                 575

Leu Val Ala Ala Thr Met Leu Leu Leu Pro Pro Leu Ser Pro Gly
            580                 585                 590

Ala Leu Trp Thr Ala Ala Gln Ala Leu Thr Leu
            595                 600

<210> SEQ ID NO 2
<211> LENGTH: 2432
<212> TYPE: DNA
<213> ORGANISM: Homo sapiens

<400> SEQUENCE: 2
agtccggcgg gggcgccgcg gagagcggag ggcgccgggc tgcggaacgc gaagcggagg      60
gcgcgggacc ctgcacgccg cccgcgggcc catgtgagcg ccatgcggcg ccgcgcagcc     120
cggggacccg gcccgccgcc cccagggccc ggactctcgc ggctgccgct gccgctgctg     180
ctgctgctgg cgctggggac ccgcgggggc tgcgccgcgc ccgcacccgc gccgcgcgcc     240
gaggacctca gctgggagt ggagtggcta agcaggttcg gttacctgcc cccggctgac     300
cccacaacag ggcagctgca gacgcaagag gagctgtcta aggccatcac agccatgcag     360
cagtttggtg gcctggaggc caccggcatc ctggacgagg ccaccctggc cctgatgaaa     420
accccacgct gctccctgcc agacctccct gtcctgaccc aggctcgcag agacgccag      480 gctccagccc ccaccaagtg gaacaagagg aacctgtcgt ggagggtccg gacgttccca     540
cgggactcac cactggggca cgacacggtg cgtgcactca tgtactacgc cctcaaggtc     600
tggagcgaca ttgcgcccct gaacttccac gaggtggcgg gcagcgccgc gacatccag      660 atcgacttct ccaaggccga ccataacgac ggctaccccct cgacggcccc ggcggcacc     720 gtggcccacg ccttcttccc cggccaccac cacaccgccg ggacacccca ctttgacgat     780

```
gacgaggcct ggaccttccg ctcctcggat gcccacggga tggacctgtt tgcagtggct    840
gtccacgagt ttggccacgc cattgggtta agccatgtgg ccgctgcaca ctccatcatg    900
cggccgtact accagggccc ggtgggtgac ccgctgcgct acgggctccc ctacgaggac    960
aaggtgcgcg tctggcagct gtacggtgtg cgggagtctg tgtctcccac ggcgcagccc   1020
gaggagcctc ccctgctgcc ggagccccca gacaaccggt ccagcgcccc gcccaggaag   1080
gacgtgcccc acagatgcag cactcacttt gacgcggtgg cccagatccg gggtgaagct   1140
ttcttcttca aaggcaagta cttctggcgg ctgacgcggg accggcacct ggtgtccctg   1200
cagccggcac agatgcaccg cttctggcgg ggcctgccgc tgcacctgga cagcgtggac   1260
gccgtgtacg agcgcaccag cgaccacaag atcgtcttct ttaaaggaga caggtactgg   1320
gtgttcaagg acaataacgt agaggaagga tacccgcgcc ccgtctccga cttcagcctc   1380
ccgcctggcg gcatcgacgc tgccttctcc tgggcccaca atgacaggac ttatttcttt   1440
aaggaccagc tgtactggcg ctacgatgac cacacgaggc acatggaccc cggctacccc   1500
gcccagagcc ccctgtggag gggtgtcccc agcacgctgg acgacgccat cgctggtcc    1560
gacggtgcct cctacttctt ccgtggccag gagtactgga aagtgctgga tggcgagctg   1620
gaggtggcac ccgggtaccc acagtccacg gcccgggact ggctggtgtg tggagactca   1680
caggccgatg gatctgtggc tgcgggcgtg gacgcggcag aggggccccg cgcccctcca   1740
ggacaacatg accagagccg ctcggaggac ggttacgagg tctgctcatg cacctctggg   1800
gcatcctctc ccccgggggc cccaggccca ctggtggctg ccaccatgct gctgctgctg   1860
ccgccactgt caccaggcgc cctgtggaca gcggcccagg ccctgacgct atgcacaca    1920
gcgcgagccc atgagaggac agaggcggtg ggacagcctg ccacagagg caaggactg     1980
tgccggagtc cctgggggag gtgctggcgc gggatgagga cgggccaccc tggcaccgga   2040
aggccagcag agggcactgc ccgccagggc tgggcaggct caggtggcaa ggacggagct   2100
gtcccctagt gagggactgt gttgactgac gagccgaggg gtggccgctc cagaagggtg   2160
cccagtcagg ccgcaccgcc gccagcctcc tccggccctg gagggagcat ctcgggctgg   2220
gggcccaccc ctctctgtgc cggcgccacc aaccccaccc acactgctgc ctggtgctcc   2280
cgccggccca cagggcctcc gtcccaggt ccccagtggg gcagccctcc ccacagacga    2340
gcccccaca tggtgccgcg gcacgtcccc cctgtgacgc gttccagacc aacatgacct    2400
ctccctgctt tgtaaaaaaa aaaaaaaaaa aa                                  2432
```

<210> SEQ ID NO 3
<211> LENGTH: 326
<212> TYPE: PRT
<213> ORGANISM: Homo sapiens

<400> SEQUENCE: 3

```
Met Ser Gln Ser Lys Gly Lys Lys Arg Asn Pro Gly Leu Lys Ile Pro
1               5                   10                  15

Lys Glu Ala Phe Glu Gln Pro Gln Thr Ser Ser Lys Ala Cys Ile Ser
            20                  25                  30

Ile Gly Asn Gln Asn Phe Glu Val Lys Ala Asp Asp Leu Glu Pro Ile
        35                  40                  45

Met Glu Leu Gly Arg Gly Ala Tyr Gly Val Val Glu Lys Met Arg His
    50                  55                  60

Val Pro Ser Gly Gln Ile Met Ala Val Lys Arg Ile Arg Ala Thr Val
65                  70                  75                  80
```

```
Asn Ser Gln Glu Gln Lys Arg Leu Leu Met Asp Leu Asp Ile Ser Met
                 85                  90                  95
Arg Thr Val Asp Cys Pro Phe Thr Val Thr Phe Tyr Gly Ala Leu Phe
            100                 105                 110
Arg Glu Gly Asp Val Trp Ile Cys Met Glu Leu Met Asp Thr Ser Leu
        115                 120                 125
Asp Lys Phe Tyr Lys Gln Val Ile Asp Lys Gly Gln Thr Ile Pro Glu
    130                 135                 140
Asp Ile Leu Gly Lys Ile Ala Val Ser Ile Val Lys Ala Leu Glu His
145                 150                 155                 160
Leu His Ser Lys Leu Ser Val Ile His Arg Asp Val Lys Pro Ser Asn
                165                 170                 175
Val Leu Ile Asn Ala Leu Gly Gln Val Lys Met Cys Asp Phe Gly Ile
            180                 185                 190
Ser Gly Tyr Leu Val Asp Ser Val Ala Lys Thr Ile Asp Ala Gly Cys
        195                 200                 205
Lys Pro Tyr Met Ala Pro Glu Arg Ile Asn Pro Glu Leu Asn Gln Lys
    210                 215                 220
Gly Tyr Ser Val Lys Ser Asp Ile Trp Ser Leu Gly Ile Thr Met Ile
225                 230                 235                 240
Glu Leu Ala Ile Leu Arg Phe Pro Tyr Asp Ser Trp Gly Thr Pro Phe
                245                 250                 255
Gln Gln Leu Lys Gln Val Val Glu Glu Pro Ser Pro Gln Leu Pro Ala
            260                 265                 270
Asp Lys Phe Ser Ala Glu Phe Val Asp Phe Thr Ser Gln Cys Leu Lys
        275                 280                 285
Lys Asn Ser Lys Glu Arg Pro Thr Tyr Pro Glu Leu Met Gln His Pro
    290                 295                 300
Phe Phe Thr Leu His Glu Ser Lys Gly Thr Asp Val Ala Ser Phe Val
305                 310                 315                 320
Lys Leu Ile Leu Gly Asp
                325

<210> SEQ ID NO 4
<211> LENGTH: 1879
<212> TYPE: DNA
<213> ORGANISM: Homo sapiens

<400> SEQUENCE: 4
agttccaagt tggagctttt tagctgccag ccctggccca tcatgtagct gcagcacagc      60
cttccctaac gttgcaactg ggggaaaaat cactttccag tctgttttgc aaggtgtgca    120
tttccatctt gattcctga aagtccatct gctgcatcgg tcaagagaaa ctccacttgc     180
atgaagattg cacgcctgca gcttgcatct tgttgcaaa actagctaca gaagagaagc     240
aaggcaaagt cttttgtgct ccctcccccc atcaaaggaa aggggaaaat gtctcagtcg    300
aaaggcaaga agcgaaaccc tggccttaaa attccaaaag aagcatttga caacctcag    360
accagttcca caccacctcg agatttagac tccaaggctt gcatttctat ggaaatcag    420
aactttgagg tgaaggcaga tgacctggag cctataatgg aactgggacg aggtgcgtac    480
ggggtggtgg agaagatgcg gcacgtgccc agcgggcaga tcatggcagt gaagcggatc    540
cgagccacag taaatagcca ggaacagaaa cggctactga tggatttgga tatttccatg    600
aggacgtgta actgtccatt cactgtcacc ttttatggcg cactgtttcg ggagggtgat    660
gtgtggatct gcatggagct catggataca tcactagata aattctacaa caagttatt    720
```

```
gataaaggcc agacaattcc agaggacatc ttagggaaaa tagcagtttc tattgtaaaa      780
gcattagaac atttacatag taagctgtct gtcattcaca gagacgtcaa gccttctaat      840
gtactcatca atgctctcgg tcaagtgaag atgtgcgatt ttggaatcag tggctacttg      900
gtggactctg ttgctaaaac aattgatgca ggttgcaaac catacatggc ccctgaaaga      960
ataaacccag agctcaacca gaagggatac agtgtgaagt ctgacatttg gagtctgggc     1020
atcacgatga ttgagttggc catccttcga tttccctatg attcatgggg aactccattt     1080
cagcagctca aacaggtggt agaggagcca tcgccacaac tcccagcaga caagttctct     1140
gcagagtttt ttgactttac ctcacagtgc ttaaagaaga attccaaaga acggcctaca     1200
tacccagagc taatgcaaca tccattttc accctacatg aatccaaagg aacagatgtg      1260
gcatcttttg taaaactgat tcttggagac taaaaagcag tggacttaat cggttgaccc     1320
tactgtggat tggtgggttt cggggtgaag caagttcact acagcatcaa tagaaagtca     1380
tctttgagat aatttaaccc tgcctctcag agggttttct ctcccaattt tcttttact     1440
cccctctta aggggccctt ggaatctata gtatagaatg aactgtctag atggatgaat      1500
tatgataaag gcttaggact tcaaaaggtg attaaatatt taatgatgtg tcatatgagt     1560
cctcaagctt ctcagacttc tcttattctt tacaaaatga atgcattggc cctgacaaaa     1620
aggtgctacg gtagtgatga aattataagt agatttgtag tttgtcccat ttattatttt     1680
aatatttatg tttaagtgct tggttgaaaa gattccattt tatacaagaa gggagattca     1740
aaaaaaaaat ataaggttgg gttagcaata tttatagggc ttttattttt taagttcaat     1800
tgtgtctgtg gtccagaaga aattatttaa tatgcatctt tgagaatatt ataaaaatat     1860
caaaaggaa aaaaaaaa                                                    1879

<210> SEQ ID NO 5
<211> LENGTH: 278
<212> TYPE: PRT
<213> ORGANISM: Homo sapiens

<400> SEQUENCE: 5

Met Glu Leu Gly Arg Gly Ala Tyr Gly Val Val Glu Lys Met Arg His
1               5                   10                  15

Val Pro Ser Gly Gln Ile Met Ala Val Lys Arg Ile Arg Ala Thr Val
            20                  25                  30

Asn Ser Gln Glu Gln Lys Arg Leu Leu Met Asp Leu Asp Ile Ser Met
        35                  40                  45

Arg Thr Val Asp Cys Pro Phe Thr Val Thr Phe Tyr Gly Ala Leu Phe
    50                  55                  60

Arg Glu Gly Asp Val Trp Ile Cys Met Glu Leu Met Asp Thr Ser Leu
65                  70                  75                  80

Asp Lys Phe Tyr Lys Gln Val Ile Asp Lys Gly Gln Thr Ile Pro Glu
                85                  90                  95

Asp Ile Leu Gly Lys Ile Ala Val Ser Ile Val Lys Ala Leu Glu His
            100                 105                 110

Leu His Ser Lys Leu Ser Val Ile His Arg Asp Val Lys Pro Ser Asn
        115                 120                 125

Val Leu Ile Asn Ala Leu Gly Gln Val Lys Met Cys Asp Phe Gly Ile
    130                 135                 140

Ser Gly Tyr Leu Val Asp Ser Val Ala Lys Thr Ile Asp Ala Gly Cys
145                 150                 155                 160
```

```
Lys Pro Tyr Met Ala Pro Glu Arg Ile Asn Pro Glu Leu Asn Gln Lys
            165                 170                 175

Gly Tyr Ser Val Lys Ser Asp Ile Trp Ser Leu Gly Thr Met Ile
        180                 185                 190

Glu Leu Ala Ile Leu Arg Phe Pro Tyr Asp Ser Trp Gly Thr Pro Phe
            195                 200                 205

Gln Gln Leu Lys Gln Val Val Glu Glu Pro Ser Pro Gln Leu Pro Ala
        210                 215                 220

Asp Lys Phe Ser Ala Glu Phe Val Asp Phe Thr Ser Gln Cys Leu Lys
225                 230                 235                 240

Lys Asn Ser Lys Glu Arg Pro Thr Tyr Pro Glu Leu Met Gln His Pro
                245                 250                 255

Phe Phe Thr Leu His Glu Ser Lys Gly Thr Asp Val Ala Ser Phe Val
            260                 265                 270

Lys Leu Ile Leu Gly Asp
            275
```

<210> SEQ ID NO 6
<211> LENGTH: 13577
<212> TYPE: DNA
<213> ORGANISM: Homo sapiens

<400> SEQUENCE: 6

```
ttgctgcaat ccgaacttga ggaggggtg gagtctgttc agttctgttt ctccttgccg      60
aagtgtggtc tttggagcta agtgaagaat gacttctgtt aggttttcct ctgctggtct    120
tccttgcagc ctcgaaaacc tcaccagagt cgcctctgct ggtctcttac tgtgctgctc    180
tgtcagagat gggcaagtaa gcgaactgca gagtgttgct gtgtgtgctt gtgatttgta    240
tttatttga tgtaaacgtg aaggcagagt attttctaac actgtaattc aactaggttt     300
tgtgtctcct ggatctattt tttttcttg ttgttctgag gagctgatat acttggaaat     360
attaggttta agatatgcag atgtccaact tatatacata gtcaagggtt tagagtctgg    420
agacaggagg ctggcaattt caactaggag gcagtaaatt cagggcaaga agcgaaaccc    480
tggccttaaa attccaaaag aagcatttga acaacctcag accagttcca caccacctcg    540
agatttagac tccaaggctt gcatttctat tggaaatcag aactttgagg tgaaggcaga    600
tgacctggag cctataatgg aactgggacg aggtgcgtac ggggtggtgg agaagatgcg    660
gcacgtgccc agcgggcaga tcatggcagt gaagcggatc cgagccacag taaatagcca    720
ggaacagaaa cggctactga tggatttgga tatttccatg aggacggtgg actgtccatt    780
cactgtcacc ttttatggcg cactgtttcg ggagggtgat gtgtggatct gcatggagct    840
catggataca tcactagata aattctacaa acaagttatt gataaaggcc agacaattcc    900
agaggacatc ttagggaaaa tagcagtttc tattgtaaaa gcattagaac atttacatag    960
taagctgtct gtcattcaca gagacgtcaa gccttctaat gtactcatca atgctctcgg   1020
tcaagtgaag atgtgcgatt ttggaatcag tggctacttg gtggactctg ttgctaaaac   1080
aattgatgca ggttgcaaac catacatggc ccctgaaaga ataaacccag agctcaacca   1140
gaagggatac agtgtgaagt ctgacatttg agtctgggc atcacgatga ttgagttggc   1200
catccttcga tttccctatg attcatgggg aactccattt cagcagctca acaggtggt    1260
agaggagcca tcgccacaac tcccagcaga caagttctct gcagagtttg ttgactttac   1320
ctcacagtgc ttaaagaaga attccaaaga acggcctaca tacccagagc taatgcaaca   1380
tccatttttc accctacatg aatccaaagg aacagatgtg catcttttg taaaactgat   1440
```

```
tcttggagac taaaaagcag tggacttaat cggttgaccc tactgtggat tggtgggttt    1500
cggggtgaag caagttcact acagcatcaa tagaaagtca tctttgagat aatttaaccc    1560
tgcctctcag agggttttct ctcccaattt tcttttact ccccctctta aggggccttt     1620
ggaatctata gtatagaatg aactgtctag atggatgaat tatgataaag cttaggact    1680 tcaaaggtg attaaatatt taatgatgtg tcatatgagt cctcaagctt ctcagacttc    1740
tcttattctt tacaaaatga atgcattggc cctgacaaaa aggtgctacg gtagtgatga    1800
aattataagt agatttgtag tttgtcccat ttattatttt aatatttatg tttaagtgct    1860
tggttgaaaa gattccattt tatacaagaa gggagattca aaaaaaaat ataaggttgg     1920 gttagcaata tttataggc ttttattttt aagttcaat tgtgtctgtg gtccagaaga      1980
aattatttaa tatgcatctt tgagaatatt ataaaaatat caaaaggag ctcttcttgt     2040 gaaatgtctg ttccagctgt tgtgactgct gccattttg caaacatctg cccaatcctg     2100
ggtgatcacc acatcttta ggggaagtga caagatgctc tggtcatact cttttccca     2160 actttggaaa acataaaaat cactcatata acagctcaaa gagtaaaaca tttggttctt    2220
ctgacacttg tggtatagta ttagtggaaa gtgatttgta atatgatttt atatccacct    2280
acctattcat ctacctgtgt gtatgtgtgt gtttgtgtgt ctatttggca attcacaagt    2340
cctgccaagt ggtttctatg agcatctctg tttggtaagg aggacaattg tcagttttga    2400 ggggacatg tgttaaatca cagaaaaaaa tggtgccttc ttctgcgttt gtccctcctg     2460
ccatgtgtaa gttgtaagga ttgccttttgt agttaatgta ctctttggct ttgtttgttt    2520
gttttcttct tcagtgaagc agccttacta ttcatagaag ggctagaata ggagaaaatg    2580
aaaggtagtg agtaattctt tgataagatg aggaaataat gggaaaggtt gaattaattc    2640
ctgggcatgg actaccagat gaccacaagt tgcgttgagg ccgcatcttt cttcagcagc    2700
gtgcaatagc tggctcctct ataggagatg agcttcattg ggagttccta gcaagttgac    2760
taaacagcaa aagttctttc tcgtgggtaa atatacccac aggttctatg atttgtagct    2820
ctaggtttct tgatgatcaa ggagtgaagt aattgacagg gaaaatatag acctatgata    2880
aataaccagg aagcattgct tttggacaag gaaggacaga gggttttgat tttaaaaga     2940 agaaaaaaaa accttatttt ttcttttcttg gcctcaagtt caatatggag aggattgctt    3000
ccctgaatcc tctcttcctt cccctttag attttgaagt gcaatcatat gtttttctct     3060
gtttgcattt tttcctcctt gttcttgaca aggaggagtt gctcctgccc agaatgagcg    3120
tgacacttcc gaacacttct tcatattcag ttccaagata tatctgcttg attaaacatg    3180
agcttcctct gctctgaagc tacctctgtc ctcattttat tctagccaga aaaggagtat    3240
caccctagtg attatggctg ttcactttcc catctatctt cctaaatctg gaagttcttc    3300
tcttggagat caagagaaaa attacaattg tattccttac tttattcacc cacctatgaa    3360
aacaggaagc aataggaaaa aaaatccggt tactccattt tagcttttgg tgaacgatgt    3420
agagcaaatt gtctctctgg tctaggtccg attactctta cctgttttc cactttgaga     3480 cattctaaac agaatgtgta acttctcata tgtatgcctc tcccatctgt gaacctaggc    3540
caaagttgca aaaacaatca tattaatagt agagtagaga aaaagttagt ctatggttct    3600
caaccctcgt gtacattgga accatctggg agctgtgaac actgtcgctg ccaatgttcc    3660
agccaccaga gatttggatt taactggtgg ggcctaggaa ttggtgtttt ttgttttgt     3720 tttgtttttt acacaccttc atgtgattct gatgtgaagc tgggttcaga acacttatct    3780
```

-continued

```
agtaccttct aaagagaact gacttaaatt tactttcttt tgaacatttg cagggagtaa      3840
catgccattg cagaaagtaa caaaaacagg tcctatttct ttccctgtcc tcatcagtgg      3900
aaatctcttt gtcactctga gagaaggcat gtacctggga tactgatagg aagtgtagaa      3960
cacctttttcc ccagagaagc aatattttgc actgttatta aatatcttac acggtaaagt    4020
caaaagaatg acctgatagc ctcacaagac taaattttag agcatggttt tgttttgga      4080
aaactgtgtt gtaagtgcca atcaaccaac ttttgaaaaa atcaagatac ctaaactata     4140
tataaatggg gagtattctg tacatataga cttatatata aagacatctg tgttcacgga    4200
tgaccctcaa aatagttaat gccccaccag catagaccat ctgaatatca gccctgtcta   4260
cacctatcaa tgtattacaa aatcagtata gctctacaaa agagatcatg cttatttccc   4320
cagatgtatt tgattttgta tcatataatt gtccatgtta aattttttga aaatgtttat    4380
taaaatagcc atctttttg atattattgg tttaagaggt gtgccaaaaa aagtaatatg    4440
cataactttt aagactatta ccctatgttt gtacgtatga gtgaatattg cccaccagag   4500
tagccatctt gagagactac atatttatat tcataatgct attaaattat ttttgccact  4560
cctctttcag aaaaggcttt agaatccact ccctcctctg agatgtgtgt catcatttga   4620
gaattcttac ttaggttttg ttgttgtttg ttttgctttt tacaaaaatc cttagcagat   4680
gtttccctct ttgatttacc tgccttgttt atcagatttt gcacaaagtt gtgtttgaca  4740
atttctagaa gttaaatctt ccctcagagc tggagttttta gcatcattga ctctttgtaa   4800
aacgccatgt catgggctct gaagataatt tcaaatgaag atttccacac cccgccccca   4860
ccaccctgc ccaaagtgca tgattatttt taaccagagt cattcttcca ccagaataag   4920
tgtaatctcc caaatgact actttgaagg agatagaacc cccataaagg tatatgtttg    4980
ttgataaaat atcaggtcat cacggatttt gcaagtgaaa gtcacctatc ttctatgatt    5040
gaaggtcctg atgtggggga ataatctatt ttttctaaag actgtgtttg gtcacactga    5100
tttaatcaga acaaatgggt taaataagca gcttttatca cagttaagcc atctgaaatg   5160
gaaacgagta tgtatgggca tggcttgaaa ttgtttgtat tttacagttc ttgtatatcc    5220
ttcaagccta acaaaaaatt gtatgtgcca gagattccta aactttctgt gttcagggtg   5280
ccattagttg tcttggtact tttttcatgg tgccccaggt caaaatatat acttaatagt   5340
tcagtgtttt aagtaattag gtcccaacag cttaataata gcagtttgca cagtgtcctg   5400
catatatcac tatatttccc ttaaaaattt ccagcattgg ctgagcatgg tgactcacgc    5460
ctgtaatccc agcactttgg gaggctgagg caggtggatc acctcaggtc aggaatttga    5520
gaccagcctg actaacatga tgaaacccg tctctactaa aaatacaaaa ttagctgggc   5580
atggtggcac atgcctgtaa tcccagctac tcaggaggct gaggcaggag aattgcttga   5640
acccgggagg cggaggttgc agtgagccga catcgtgtca gtgcactcca gcctgggcaa   5700
caagagcaaa acttcatctc aaaaaaaaa aaaaaaatg tacaacatct tgcttagcct     5760
gtgtgtgttc tgtggtacct tggaatagct cagtacataa tttggggacc acagatatct    5820
attatgccaa tgtttgcact gtctgctgtt ggtgaccctc aaaatgaaat tcttggccac    5880
tcaactctcc acattatttc actctttgtt ttgttattat tagtattctt cttgcttgcc    5940
attggctaat tcattttttta actgcaaccc tactcttctt tgctgttcat cagccctgca   6000
atgccgtagt gtcttagtct agaaaaatgc aatactcaaa agcccagca ttggaggagg    6060
ctggtgctaa gatggacagg gttcctgatt tctctcattg aacttgattt agtgtcttgg    6120
gaattataat ctcaaaggag gcagagaggg gttaatgttg cataatttat cactaaaatg   6180
```

-continued

```
tctttgttga ccaaggggct ttattaatta tgctcagaga aacaattctg tttctcttaa      6240
aagtgtctaa caaaacactt ttttctttgg cctgaaagga caatggatac ctagttccta      6300
atttcctacc caaatgctgt tttggctgtg ttactccctc tgccctcgaa gctaagattt      6360
atatatttac aaaatttatt ggagctggta gtcagatcta gtaaaatgga ttaaatgtca      6420
attgtgctgg gattttgcct taacatctat ctatgacttg aagagggatt tgttggctca      6480
aaggatcttc tgcttttaat gaattagcaa gtgaaaaggt atttgaataa atgtcaactt      6540
cataggactt tttttttttt taacttttca aatggaaggt gcagttttca attaggcctc      6600
tgaaaattta catagtcaga tggaaaaatg ccagagtaaa atctaggaag aaggagctac      6660
cagacccgat agaatagaaa gaaagctatt ttattctcgg aggtctatgt tcctcttgtg      6720
tttgagtgcc tctagcactg ttaaatgtgc tgacagctaa agatgctctt tgggtttttt      6780
ttttggcttt aatttgggta ctatggattc ttttgggaat tgttgaaag ctaggacctt       6840 ttccccagga aaatttacat tgtatatgaa gcacataatt ttgcaaactt tttttggttg      6900
ttgttgggag ggggttgcag tttatatact ccacggggtt agtagctctg ttctgtagaa      6960
tattgactgt gacatcctag accacggttg gcaaactttt tctgtatagg accagatagt      7020
aaatattttt ggctttgtgt gttataccat ctctgtcaca gttactcagc tctgctgttg      7080
tatcatgaaa gcatctatac gcaatacaca aatgaatgag cctggtggct gtgttccaat      7140
aaaactttat ttacaaacca gcaatgggc caaatttggc ccacaggcca tggtttgcca      7200
acaccagtct tagagcatta aatataaaac tctgattaac tagatatgta gagttcttcc      7260
attttagtga ctattgagct cagctgctgt tgaggcagat taggaagatg gacataggaa      7320
actggattca gaaaggatga ggactgttta gtcccatgaa agttgcttgt taatgtcctc      7380
aggtaagtat gaattgttct ggaagctgat agaacaattt tcttcagatc aaactgaagt      7440
acttactttt tccatttcta tgcaatcacc aacataattt acttcaattt ggaaataaat      7500
gtcacagttc tcttagttgt taactgtatc cttggcttag gttatttgca ttttctttct      7560
ttctttctgt agtgtggttt atacacaagg agaatcacga acccagacac tagtcaatct      7620
ctctattccc tgacttgtac tgagattggg gaatttggga ggtcagactt acctcaaacg      7680
tagaagaagg cagatagagt tcttaacctt tttcaactta gccacctcaa ttatttgttc      7740
acattttaag gaagtaggaa agagtagttt gaagtcacaa aatttgttct caggtgttct      7800
taaagctccc tgttctcact gcgacagaag actcaggcct actcattttg tgctgtccca      7860
caaaagtgag aggagtactt ctcttttttt aaatcatcag taaatttcaa ttttaagggg      7920
cctatgcaaa atgcctcctt tctgatgtga ttttcttggg ttgctggccc tagttgaatt      7980
tatgggccct gaagcctcta gtggaaatct tgtcttccct atagaacgag aacagctatg      8040
taatttgctt caccttctgt taggacttgc accctctttg ccatacagaa tgctataaaa      8100
aggacagtct gccagtgacc gaagctttct catttttttt tcttccagaa caatagcaca      8160
catcttggtt aaagctatag tctccttatt attcagaaat attctttttc ctgctgcacc      8220
attaggcaaa catacattat gcttagaatg atacttggaa actccttaac agggcatatt      8280
gaagtatttg atccagcaac ttacctaaaa gaatgtttgc tcttcaccta gggaaataaa      8340
acctgaattt cagagccttc aaaatgaaat tatccttcca ggggaagcac attgccacca      8400
aatacatcac tcactacctg ttcctggtga ctacatagaa gatgtgttat ttttctgagg      8460
tttagaaagt cactgtttac agctatgcaa atattgtact attacagatt tttctaatga      8520
```

-continued

```
agtagtttga aatcaaggct ttagtggaag gtaatctttt cagtttctga cccagatttc    8580
tttttcaagc aaaactcctc tgaaagcctc tttgctatag aggtgatgaa ggcacttgct    8640
agcctaagca gaaacataaa gtaaaaaatt tgtagtagg gaattttgt tggtaagaaa      8700 tcagtatcat cttgtaacac aaacacgtgt aatagaact taaaaatact cagcctaatt     8760
ccttgggact ttcagtatct tgacatcact tgtattatca tttgaacttg gacattgagc    8820
cctttatttt tgggagttta cagttaaatt ttggaagaat tgtgttgtat ttctttctta    8880
gatgttgtca gtatgaacag aattttttg tgaacagtta atcttgatgt gctccatagc     8940
tttctccagt ttacacttt gcatttctga gattcagggt cttttcaag gaaggaggct      9000 aatgtttaag gcctggaggc tgaattcagg gagcgtattg gcaagtttag gcacttactt    9060
gtgtcttaat gtgggaaaca gaactttcta agtaatctct ggagtttgta gcttagacca    9120
ggccttcaaa agtctttct gttttccttt gctacaattt gcttgttatt tctctgccgg     9180
tcacagatga cctggactga ctgaatgctt ttgtggtaag gaactgatct ggccattttc    9240
atataacaaa aatcaaagtc aacaattttg tatcaggctg cctaaatgaa ccctattgtt    9300
tccagttctt aaaatttaa gggctatcta agaaagttt aagcaaaacc ctcattccaa      9360
acatgcgacc ttataataag aacttccttt aaagatgagc agcaaggttg ggtatctgat    9420
ttcactaagt aatattctat tgtggtcaga aatgggtaat ttgcatcatt tggtcactat    9480
caatatttgt gttggagtct gcaagatatt tcaacaaagt aagccaaacc actatcttag    9540
gggattgttg ctggactttg aatataagg ctgaacagtg atgtgaagtc atgtttgggg     9600
gctggaagaa gtgataaatg caaggttgg tgctaaatta ggaacccctt gaaggagcaa     9660
gctgattaaa aaaaaagct ggcagacaag tatatctttt aatttatttg cagtgttgct     9720
atattataga gatgatttcc tatgggaaaa cccatcaaaa agccaaacct ttattgttat    9780
ttttccttaa aaatactgag ctataagaag attcagagag tggcattaat ttgggcatca    9840 gaacatttc ttttgtatcc ctagtgttat tgatttgaaa gagttacctt ttcagacaga     9900
tggctgaaca aaagtaaatg attaacggga aatttgatgg ttgagaaaaa ggaacgatat    9960
gcctaaagca ttttgagaat ataccccctca tccatcagcc acctctgggt aaagaaacac   10020
aaataccaaa gcctgagctc cttaaccttt tgttccagag ggcagacatt tttaagaaag    10080
gtgaatgtta gagaaggtta cctgatgagc aagcttcttt cccataattc agagaactgt    10140
gaatgtactt agaaatacac tacaggtctt caccagatga actagatttt ataattttaa    10200
aatataatac tgaaagctag tttgaagttt cagaagccat gaattatggg gaaggagtag    10260
ttttttattt tattttattt ttctgatctc aagttgtttg tcctgttgta tgttcaatac    10320
ttggggagat aagagcgagg tacagctgtg gttttcagac catattcagt ggtgcccctg    10380
agggtctctt gtgaacagaa gggaaaaaga gtgtgatgaa ggtgaactct gcctatctga    10440
acctctgtca acctccagtc agaatatctg gcttctagta ttgttccttt taactggaag    10500
tctctgtggc cattaaaaac ttgggaacgt tggattaaat gaccacttta ggactttaaa    10560
cagtctcaaa tatgggaaat tttatagcca accacggctg tgagtccctg gcttttgccg    10620
tactgagtat gctcacagag ataggggagat aggtggccag aagacagggt catttaattt   10680
taattgagca taaatcattt tgaaagaaaa atgcaaggaa ttgttgtatg acagccatgc    10740
attatagatc cttacatgcg acattttcct aaagtggttg agaatgacct gatctttgtt    10800
caccgtctca gtgacaaggc gtggagtgac tgggctcttc atatgcagtg gaattttgc     10860 atctctaggt ttgcagaggc aggagttacc gttttgttc attgacctat cagaaaaaag    10920
```

-continued

```
caaatccttt ggacaatgtt gacacagaca ggggtacggt ctgagactca agctaacaga   10980
gctaccccct gctgccttttt gcaaaggtgt tgtaggtgga aagggtaat ggaaacctgg   11040 tacagccttt agaagttgga agctatggtg gtgtatctgt catgaactgc acacaaggga   11100
atgcttaaac accagctgag tcatatcagg tgccttgtac acacacataa agagtctggt   11160
gaattctgac agtgttctgt ttgccactag agcaaattta atagctgggg tttcacagca   11220
actgttttag aaaactatat gtgccaaaaa tttacattgg gcagcagttt atagtgttct   11280
tggccaatct gcataaaagc cacttgagga ggtttgatta agaaaattgt gtttatctcc   11340
tgtattacct ctgtgtttga tttattcttt agtctcaaat ttattttctg agtggactga   11400
ttttctatat gaactgaaat gatgttttaa tagaataata ggtatttta gaggaaaagt   11460 attttttgt gtaatttgct tacacaacta ggacatactt cctatgatac tgaatcatca   11520
aattgagtca tttaaagctg aaagaggtgt taggaatgta gtttcacatt atttaaatac   11580
atgaacagtt ttctatatat tttgtgaaaa tcttgatgag acactagaat ttctttatgg   11640
aattgaactt tacaagaatt ttaataaaag aggtggattt cttcagcttt ctttgtgctt   11700
cagtttcata gctgaaaatg ctgcttccgt ttattaatat ggactttgta aggaaacaca   11760
acaacacgtt ttcttacctt ctgtaaattt tgtgatagac acatgttatt tgtatatatg   11820
attgattgtt tgcctgttgc accctaaagt tattttcaaa ccatgtttat tgcaaagaga   11880
gcctttgggc aagtggaaaa tgccctgatg ctagaatgag gtagttccat aagctagtta   11940
ggagcttgct acctcttctt ggtacctgaa atattctgaa aggatatcgg agaggtccta   12000
tgcacccctg tctttcaaaa cccacctcca gcacttcaaa gtagtgtctc tggagagttt   12060
aaaataaaag aatgaatgct attcagtgga ttccctcatt gaggctccca tctttcctgc   12120
caggtgcagc ttttctggt tggaatcatc tcttctttac ggattgccgc attgtctctt   12180
tgtgaatgag gcaggctgaa ctgtagagca tgaaactcat tagaagttta taaagtaaag   12240
acctgtaaag catgtgggtg gaatgtttcc atgctcttga ggtgaatatt aaatttaaat   12300
tctggccttt gggaactctt tgcttgtgag ctgaagaagg aaagaaggag ttggggtgt   12360 atatctaact gtgtttttct atatggaaat atatgagcat caagtgataa cttcaataag   12420
gcctcaggat tgtatttaaa atacctgttt tgtgggacag catgcctttg ttttctttgc   12480
ctgttggctt tggtggctcc aaacattttc attttaggct agcttcctg tcacccaggt   12540 tgtgtgcatt ttttttttca tttgaactat tgtttatcat tattaatgat gttatctcca   12600
aatcccaaag ccaaggaaat agccagtatg caggacttgc agtagatata agcattggtg   12660
ttaacatagg ttaagttttg ttagtgttcc cagaaatata ctgaattgag ggataatgta   12720
gctttaaaga aattatgttt ctttttaaca tttggagaag ccacctgtcc tgggtcccta   12780
ttcttgagaa attcatcttt tcatgcaaat aacattgatg ggggacaaga ctggatgatt   12840
gacttctatc agtcagtaga caaggaagta taataattgc caaaggtgag ggtaattttg   12900
ccttacaagt atgtaggtca ttctgtggtg ggatttccca tcacatctag taaaaaacaa   12960
ccttttcatt tccctccttt ctaatccaag atcatatttt taaaaagtag gtttctgatg   13020
tgccatgaaa tatttctgtg aatctgtgtt tttgaccaag gaaacagctg agatattaaa   13080
ccatgtggtt gttccacggt tcatctggct accgttctgg gtcccctctg accacctcaa   13140
aaagaaaatg aaattgggag attaaatcaa gcttgacctc ctctttaat gaggaacttt   13200 cacgttgact tccatctctca ggatattctt cagtttcata ctgctgagga gaaaggaaca   13260
```

```
agctgcagac actgtaactg gtctccagat gtgtgtatat gcgtgtaaaa cttcacaccg    13320
tgtgtgttgt gttcaatgtt gtgtcaatct acaaactgac tcaaacaaca gtttaacgat    13380
agagaagaca gtgataatgg caaaaaaaac acccaaccac cttttccgt  caaagtgctt    13440 gctatggctt tcatagctgg gacaagtaac attaagtatt caggagcaaa gtgttcttga    13500
aagaaaatgg tgtgttgatc tcataagaaa atgtacaacc aataaaagac attttaaaaa    13560 gaaaaaaaa  aaaaaaa                                                   13577
```

<210> SEQ ID NO 7
<211> LENGTH: 1608
<212> TYPE: PRT
<213> ORGANISM: Homo sapiens

<400> SEQUENCE: 7

```
Met Arg Glu Ala Ala Ala Ala Leu Val Pro Pro Ala Phe Ala Val
1               5                   10                  15

Thr Pro Ala Ala Ala Met Glu Glu Pro Pro Pro Pro Pro Pro
            20                  25                  30

Pro Pro Pro Pro Glu Pro Glu Thr Glu Ser Glu Pro Glu Cys Cys Leu
        35                  40                  45

Ala Ala Arg Gln Glu Gly Thr Leu Gly Asp Ser Ala Cys Lys Ser Pro
    50                  55                  60

Glu Ser Asp Leu Glu Asp Phe Ser Asp Glu Thr Asn Thr Glu Asn Leu
65                  70                  75                  80

Tyr Gly Thr Ser Pro Pro Ser Thr Pro Arg Gln Met Lys Arg Met Ser
                85                  90                  95

Thr Lys His Gln Arg Asn Asn Val Gly Arg Pro Ala Ser Arg Ser Asn
            100                 105                 110

Leu Lys Glu Lys Met Asn Ala Pro Asn Gln Pro Pro His Lys Asp Thr
        115                 120                 125

Gly Lys Thr Val Glu Asn Val Glu Glu Tyr Ser Tyr Lys Gln Glu Lys
    130                 135                 140

Lys Ile Arg Ala Ala Leu Arg Thr Thr Glu Arg Asp His Lys Lys Asn
145                 150                 155                 160

Val Gln Cys Ser Phe Met Leu Asp Ser Val Gly Gly Ser Leu Pro Lys
                165                 170                 175

Lys Ser Ile Pro Asp Val Asp Leu Asn Lys Pro Tyr Leu Ser Leu Gly
            180                 185                 190

Cys Ser Asn Ala Lys Leu Pro Val Ser Val Pro Met Pro Ile Ala Arg
        195                 200                 205

Pro Ala Arg Gln Thr Ser Arg Thr Asp Cys Pro Ala Asp Arg Leu Lys
    210                 215                 220

Phe Phe Glu Thr Leu Arg Leu Leu Leu Lys Leu Thr Ser Val Ser Lys
225                 230                 235                 240

Lys Lys Asp Arg Glu Gln Arg Gly Gln Glu Asn Thr Ser Gly Phe Trp
                245                 250                 255

Leu Asn Arg Ser Asn Glu Leu Ile Trp Leu Glu Leu Gln Ala Trp His
            260                 265                 270

Ala Gly Arg Thr Ile Asn Asp Gln Asp Phe Phe Leu Tyr Thr Ala Arg
        275                 280                 285

Gln Ala Ile Pro Asp Ile Ile Asn Glu Ile Leu Thr Phe Lys Val Asp
    290                 295                 300

Tyr Gly Ser Phe Ala Phe Val Arg Asp Arg Ala Gly Phe Asn Gly Thr
305                 310                 315                 320
```

```
Ser Val Glu Gly Gln Cys Lys Ala Thr Pro Gly Thr Lys Ile Val Gly
            325                 330                 335
Tyr Ser Thr His His Glu His Leu Gln Arg Gln Arg Val Ser Phe Glu
            340                 345                 350
Gln Val Lys Arg Ile Met Glu Leu Leu Glu Tyr Ile Glu Ala Leu Tyr
            355                 360                 365
Pro Ser Leu Gln Ala Leu Gln Lys Asp Tyr Glu Lys Tyr Ala Ala Lys
            370                 375                 380
Asp Phe Gln Asp Arg Val Gln Ala Leu Cys Leu Trp Leu Asn Ile Thr
385                 390                 395                 400
Lys Asp Leu Asn Gln Lys Leu Arg Ile Met Gly Thr Val Leu Gly Ile
            405                 410                 415
Lys Asn Leu Ser Asp Ile Gly Trp Pro Val Phe Glu Ile Pro Ser Pro
            420                 425                 430
Arg Pro Ser Lys Gly Asn Glu Pro Glu Tyr Glu Gly Asp Asp Thr Glu
            435                 440                 445
Gly Glu Leu Lys Glu Leu Glu Ser Ser Thr Asp Glu Ser Glu Glu Glu
            450                 455                 460
Gln Ile Ser Asp Pro Arg Val Pro Glu Ile Arg Gln Pro Ile Asp Asn
465                 470                 475                 480
Ser Phe Asp Ile Gln Ser Arg Asp Cys Ile Ser Lys Lys Leu Glu Arg
            485                 490                 495
Leu Glu Ser Glu Asp Asp Ser Leu Gly Trp Gly Ala Pro Asp Trp Ser
            500                 505                 510
Thr Glu Ala Gly Phe Ser Arg His Cys Leu Thr Ser Ile Tyr Arg Pro
            515                 520                 525
Phe Val Asp Lys Ala Leu Lys Gln Met Gly Leu Arg Lys Leu Ile Leu
            530                 535                 540
Arg Leu His Lys Leu Met Asp Gly Ser Leu Gln Arg Ala Arg Ile Ala
545                 550                 555                 560
Leu Val Lys Asn Asp Arg Pro Val Glu Phe Ser Glu Phe Pro Asp Pro
            565                 570                 575
Met Trp Gly Ser Asp Tyr Val Gln Leu Ser Arg Thr Pro Pro Ser Ser
            580                 585                 590
Glu Glu Lys Cys Ser Ala Val Ser Trp Glu Glu Leu Lys Ala Met Asp
            595                 600                 605
Leu Pro Ser Phe Glu Pro Ala Phe Leu Val Leu Cys Arg Val Leu Leu
            610                 615                 620
Asn Val Ile His Glu Cys Leu Lys Leu Arg Leu Glu Gln Arg Pro Ala
625                 630                 635                 640
Gly Glu Pro Ser Leu Leu Ser Ile Lys Gln Leu Val Arg Glu Cys Lys
            645                 650                 655
Glu Val Leu Lys Gly Gly Leu Leu Met Lys Gln Tyr Tyr Gln Phe Met
            660                 665                 670
Leu Gln Glu Val Leu Glu Asp Leu Lys Pro Asp Cys Asn Ile Asp
            675                 680                 685
Ala Phe Glu Glu Asp Leu His Lys Met Leu Met Val Tyr Phe Asp Tyr
            690                 695                 700
Met Arg Ser Trp Ile Gln Met Leu Gln Gln Leu Pro Gln Ala Ser His
705                 710                 715                 720
Ser Leu Lys Asn Leu Leu Glu Glu Glu Trp Asn Phe Thr Lys Glu Ile
            725                 730                 735
```

```
Thr His Tyr Ile Arg Gly Gly Glu Ala Gln Ala Gly Lys Leu Phe Cys
            740                 745                 750

Asp Ile Ala Gly Met Leu Leu Lys Ser Thr Gly Ser Phe Leu Glu Phe
            755                 760                 765

Gly Leu Gln Glu Ser Cys Ala Glu Phe Trp Thr Ser Ala Asp Asp Ser
        770                 775                 780

Ser Ala Ser Asp Glu Ile Arg Arg Ser Val Ile Glu Ile Ser Arg Ala
785                 790                 795                 800

Leu Lys Glu Leu Phe His Glu Ala Arg Glu Arg Ala Ser Lys Ala Leu
                805                 810                 815

Gly Phe Ala Lys Met Leu Arg Lys Asp Leu Glu Ile Ala Ala Glu Phe
            820                 825                 830

Arg Leu Ser Ala Pro Val Arg Asp Leu Leu Asp Val Leu Lys Ser Lys
            835                 840                 845

Gln Tyr Val Lys Val Gln Ile Pro Gly Leu Glu Asn Leu Gln Met Phe
        850                 855                 860

Val Pro Asp Thr Leu Ala Glu Glu Lys Ser Ile Ile Leu Gln Leu Leu
865                 870                 875                 880

Asn Ala Ala Ala Gly Lys Asp Cys Ser Lys Asp Ser Asp Val Leu
                885                 890                 895

Ile Asp Ala Tyr Leu Leu Leu Thr Lys His Gly Asp Arg Ala Arg Asp
            900                 905                 910

Ser Glu Asp Ser Trp Gly Thr Trp Glu Ala Gln Pro Val Lys Val Val
            915                 920                 925

Pro Gln Val Glu Thr Val Asp Thr Leu Arg Ser Met Gln Val Asp Asn
        930                 935                 940

Leu Leu Leu Val Val Met Gln Ser Ala His Leu Thr Ile Gln Arg Lys
945                 950                 955                 960

Ala Phe Gln Gln Ser Ile Glu Gly Leu Met Thr Leu Cys Gln Glu Gln
                965                 970                 975

Thr Ser Ser Gln Pro Val Ile Ala Lys Ala Leu Gln Gln Leu Lys Asn
            980                 985                 990

Asp Ala Leu Glu Leu Cys Asn Arg Ile Ser Asn Ala Ile Asp Arg Val
            995                 1000                1005

Asp His Met Phe Thr Ser Glu Phe Asp Ala Glu Val Asp Glu Ser
        1010                1015                1020

Glu Ser Val Thr Leu Gln Gln Tyr Tyr Arg Glu Ala Met Ile Gln
        1025                1030                1035

Gly Tyr Asn Phe Gly Phe Glu Tyr His Lys Glu Val Val Arg Leu
        1040                1045                1050

Met Ser Gly Glu Phe Arg Gln Lys Ile Gly Asp Lys Tyr Ile Ser
        1055                1060                1065

Phe Ala Arg Lys Trp Met Asn Tyr Val Leu Thr Lys Cys Glu Ser
        1070                1075                1080

Gly Arg Gly Thr Arg Pro Arg Trp Ala Thr Gln Gly Phe Asp Phe
        1085                1090                1095

Leu Gln Ala Ile Glu Pro Ala Phe Ile Ser Ala Leu Pro Glu Asp
        1100                1105                1110

Asp Phe Leu Ser Leu Gln Ala Leu Met Asn Glu Cys Ile Gly His
        1115                1120                1125

Val Ile Gly Lys Pro His Ser Pro Val Thr Gly Leu Tyr Leu Ala
        1130                1135                1140

Ile His Arg Asn Ser Pro Arg Pro Met Lys Val Pro Arg Cys His
```

```
                  1145                1150                1155

Ser  Asp  Pro  Pro  Asn  Pro  His  Leu  Ile  Ile  Pro  Thr  Pro  Glu  Gly
          1160                1165                1170

Phe  Ser  Thr  Arg  Ser  Met  Pro  Ser  Asp  Ala  Arg  Ser  His  Gly  Ser
          1175                1180                1185

Pro  Ala  Ala  Ala  Ala  Ala  Ala  Ala  Ala  Val  Ala  Ala  Ser
          1190                1195                1200

Arg  Pro  Ser  Pro  Ser  Gly  Gly  Asp  Ser  Val  Leu  Pro  Lys  Ser  Ile
          1205                1210                1215

Ser  Ser  Ala  His  Asp  Thr  Arg  Gly  Ser  Ser  Val  Pro  Glu  Asn  Asp
          1220                1225                1230

Arg  Leu  Ala  Ser  Ile  Ala  Ala  Glu  Leu  Gln  Phe  Arg  Ser  Leu  Ser
          1235                1240                1245

Arg  His  Ser  Ser  Pro  Thr  Glu  Glu  Arg  Asp  Glu  Pro  Ala  Tyr  Pro
          1250                1255                1260

Arg  Gly  Asp  Ser  Ser  Gly  Ser  Thr  Arg  Arg  Ser  Trp  Glu  Leu  Arg
          1265                1270                1275

Thr  Leu  Ile  Ser  Gln  Ser  Lys  Asp  Thr  Ala  Ser  Lys  Leu  Gly  Pro
          1280                1285                1290

Ile  Glu  Ala  Ile  Gln  Lys  Ser  Val  Arg  Leu  Phe  Glu  Glu  Lys  Arg
          1295                1300                1305

Tyr  Arg  Glu  Met  Arg  Arg  Lys  Asn  Ile  Ile  Gly  Gln  Val  Cys  Asp
          1310                1315                1320

Thr  Pro  Lys  Ser  Tyr  Asp  Asn  Val  Met  His  Val  Gly  Leu  Arg  Lys
          1325                1330                1335

Val  Thr  Phe  Lys  Trp  Gln  Arg  Gly  Asn  Lys  Ile  Gly  Glu  Gly  Gln
          1340                1345                1350

Tyr  Gly  Lys  Val  Tyr  Thr  Cys  Ile  Ser  Val  Asp  Thr  Gly  Glu  Leu
          1355                1360                1365

Met  Ala  Met  Lys  Glu  Ile  Arg  Phe  Gln  Pro  Asn  Asp  His  Lys  Thr
          1370                1375                1380

Ile  Lys  Glu  Thr  Ala  Asp  Glu  Leu  Lys  Ile  Phe  Glu  Gly  Ile  Lys
          1385                1390                1395

His  Pro  Asn  Leu  Val  Arg  Tyr  Phe  Gly  Val  Glu  Leu  His  Arg  Glu
          1400                1405                1410

Glu  Met  Tyr  Ile  Phe  Met  Glu  Tyr  Cys  Asp  Glu  Gly  Thr  Leu  Glu
          1415                1420                1425

Glu  Val  Ser  Arg  Leu  Gly  Leu  Gln  Glu  His  Val  Ile  Arg  Leu  Tyr
          1430                1435                1440

Ser  Lys  Gln  Ile  Thr  Ile  Ala  Ile  Asn  Val  Leu  His  Glu  His  Gly
          1445                1450                1455

Ile  Val  His  Arg  Asp  Ile  Lys  Gly  Ala  Asn  Ile  Phe  Leu  Thr  Ser
          1460                1465                1470

Ser  Gly  Leu  Ile  Lys  Leu  Gly  Asp  Phe  Gly  Cys  Ser  Val  Lys  Leu
          1475                1480                1485

Lys  Asn  Asn  Ala  Gln  Thr  Met  Pro  Gly  Glu  Val  Asn  Ser  Thr  Leu
          1490                1495                1500

Gly  Thr  Ala  Ala  Tyr  Met  Ala  Pro  Glu  Val  Ile  Thr  Arg  Ala  Lys
          1505                1510                1515

Gly  Glu  Gly  His  Gly  Arg  Ala  Ala  Asp  Ile  Trp  Ser  Leu  Gly  Cys
          1520                1525                1530

Val  Val  Ile  Glu  Met  Val  Thr  Gly  Lys  Arg  Pro  Trp  His  Glu  Tyr
          1535                1540                1545
```

| Glu | His | Asn | Phe | Gln | Ile | Met | Tyr | Lys | Val | Gly | Met | Gly | His | Lys |
|---|---|---|---|---|---|---|---|---|---|---|---|---|---|---|
| 1550 | | | | 1555 | | | | | 1560 | | | | | |

| Pro | Pro | Ile | Pro | Glu | Arg | Leu | Ser | Pro | Glu | Gly | Lys | Asp | Phe | Leu |
|---|---|---|---|---|---|---|---|---|---|---|---|---|---|---|
| 1565 | | | | | 1570 | | | | | 1575 | | | | |

| Ser | His | Cys | Leu | Glu | Ser | Asp | Pro | Lys | Met | Arg | Trp | Thr | Ala | Ser |
|---|---|---|---|---|---|---|---|---|---|---|---|---|---|---|
| 1580 | | | | | 1585 | | | | | 1590 | | | | |

| Gln | Leu | Leu | Asp | His | Ser | Phe | Val | Lys | Val | Cys | Thr | Asp | Glu | Glu |
|---|---|---|---|---|---|---|---|---|---|---|---|---|---|---|
| 1595 | | | | | 1600 | | | | | 1605 | | | | |

<210> SEQ ID NO 8
<211> LENGTH: 5564
<212> TYPE: DNA
<213> ORGANISM: Homo sapiens

<400> SEQUENCE: 8

```
gatctgggag gcttgtccct cgccgcccac cgtagcccg gcgctcggcc ggtcgccgtt      60
tccaagatgg ccgcggcgcg cacggctcct gcggcgggt agaggcggag gcggagtcga     120
gtcactcccg cacttcgggg ctccggtgcc ccgcgccagg ctgcagctta ctcccgccg     180
cggccatgcg gggctccgtg cacggatgag agaagccgct gccgcgctgg tccctcctcc     240
cgcctttgcc gtcacgcctg ccgccgccat ggaggagccg ccgccaccgc gccgccgcc     300
accaccgcca ccggaacccg agaccgagtc agaacccgag tgctgcttgg cggcgaggca     360
agagggcaca ttgggagatt cagcttgcaa gagtcctgaa tctgatctag aagacttctc     420
cgatgaaaca atacagaga atctttatgg tacctctccc cccagcacac ctcgacagat     480
gaaacgcatg tcaaccaaac atcagaggaa taatgtgggg aggccagcca gtcggtctaa     540
tttgaaagaa aaaatgaatg caccaaatca gcctccacat aaagacactg aaaaacagt      600
ggagaatgtg gaagaataca gctataagca ggagaaaaag atccgagcag ctcttagaac     660
aacagagcgt gatcataaaa aaaatgtaca gtgctcattc atgttagact cagtgggtgg     720
atctttgcca aaaaaatcaa ttccagatgt ggatctcaat aagccttacc tcagccttgg     780
ctgtagcaat gctaagcttc cagtatctgt gcccatgcct atagccagac ctgcacgcca     840
gacttctagg actgactgtc cagcagatcg tttaaagttt tttgaaactt tacgactttt     900
gctaaagctt acctcagtct caaagaaaaa agacagggag caaagaggac aagaaaatac     960
gtctggttc tggcttaacc gatctaacga actgatctgg ttagagctac aagcctggca    1020
tgcaggacgg acaattaacg accaggactt cttttatat acagcccgtc aagccatccc     1080
agatattatt aatgaaatcc ttactttcaa agtcgactat gggagcttcg cctttgttag     1140
agatagagct ggttttaatg gtacttcagt agaagggcag tgcaaagcca ctcctggaac     1200
aaagattgta ggttactcaa cacatcatga gcatctccaa cgccagaggg tctcatttga     1260
gcaggtaaaa cggataatgg agctgctaga gtacatagaa gcactttatc catcattgca     1320
ggctcttcag aaggactatg aaaaatatgc tgcaaaagac ttccaggaca gggtgcaggc     1380
actctgtttg tggttaaaca tcacaaaaga cttaaatcag aaattaagga ttatgggcac     1440
tgttttgggc atcaagaatt tatcagacat tggctggcca gtgtttgaaa tcccttcccc     1500
tcgaccatcc aaaggtaatg agccggagta tgagggtgat gacacagaag gagaattaaa     1560
ggagttggaa agtagtacgg atgagagtga agaagaacaa atctctgatc ctagggtacc     1620
ggaaatcaga cagcccatag ataacagctt cgacatccag tcgcgggact gcatatccaa     1680
gaagcttgag aggctcgaat ctgaggatga ttctcttggc tggggagcac cagactggag     1740
```

-continued

| | | | | |
|---|---|---|---|---|
| cacagaagca | ggctttagta | gacattgtct | gacttctatt | tatagaccat ttgtagacaa | 1800 |
| agcactgaag | cagatggggt | taagaaagtt | aattttaaga | cttcacaagc taatggatgg | 1860 |
| ttccttgcaa | agggcacgta | tagcattggt | aaagaacgat | cgtccagtgg agttttctga | 1920 |
| atttccagat | cccatgtggg | gttcagatta | tgtgcagttg | tcaaggacac caccttcatc | 1980 |
| tgaggagaaa | tgcagtgctg | tgtcgtggga | ggagctgaag | gccatggatt taccttcatt | 2040 |
| cgaacctgcc | ttcctagttc | tctgccgagt | ccttctgaat | gtcatacatg agtgtctgaa | 2100 |
| gttaagattg | gagcagagac | ctgctggaga | accatctctc | ttgagtatta agcagctggt | 2160 |
| gagagagtgt | aaggaggtcc | tgaagggcgg | cctgctgatg | aagcagtact accagttcat | 2220 |
| gctgcaggag | gttctggagg | acttggagaa | gcccgactgc | aacattgacg cttttgaaga | 2280 |
| ggatctacat | aaaatgctta | tggtgtattt | tgattacatg | agaagctgga tccaaatgct | 2340 |
| acagcaatta | cctcaagcat | cgcatagttt | aaaaaatctg | ttagaagaag aatggaattt | 2400 |
| caccaaagaa | ataactcatt | acatacgggg | aggagaagca | caggccggga agcttttctg | 2460 |
| tgacattgca | ggaatgctgc | tgaaatctac | aggaagtttt | ttagaatttg gcttacagga | 2520 |
| gagctgtgct | gaattttgga | ctagtgcgga | tgacagcagt | gcttccgacg aaatcaggag | 2580 |
| gtctgttata | gagatcagtc | gagccctgaa | ggagctcttc | catgaagcca gagaaagggc | 2640 |
| ttccaaagca | cttggatttg | ctaaaatgtt | gagaaaggac | ctggaaatag cagcagaatt | 2700 |
| caggcttttca | gcccccagtta | gagacctcct | ggatgttctg | aaatcaaaac agtatgtcaa | 2760 |
| ggtgcaaatt | cctgggttag | aaaacttgca | aatgtttgtt | ccagacactc ttgctgagga | 2820 |
| gaagagtatt | attttgcagt | tactcaatgc | agctgcagga | aaggactgtt caaaagattc | 2880 |
| agatgacgta | ctcatcgatg | cctatctgct | tctgaccaag | cacggtgatc gagcccgtga | 2940 |
| ttcagaggac | agctggggca | cctgggaggc | acagcctgtc | aaagtcgtgc ctcaggtgga | 3000 |
| gactgttgac | accctgagaa | gcatgcaggt | ggataatctt | ttactagttg tcatgcagtc | 3060 |
| tgcgcatctc | acaattcaga | gaaaagcttt | ccagcagtcc | attgagggac ttatgactct | 3120 |
| gtgccaggag | cagacatcca | gtcagccggt | catcgccaaa | gctttgcagc agctgaagaa | 3180 |
| tgatgcattg | gagctatgca | acaggataag | caatgccatt | gaccgcgtgg accacatgtt | 3240 |
| cacatcagaa | tttgatgctg | aggttgatga | atctgaatct | gtcaccttgc aacagtacta | 3300 |
| ccgagaagca | atgattcagg | ggtacaattt | tggatttgag | tatcataaag aagttgttcg | 3360 |
| tttgatgtct | ggggagttta | gacagaagat | aggagacaaa | tatataagct tgcccggaa | 3420 |
| gtggatgaat | tatgtcctga | ctaaatgtga | gagtggtaga | ggtacaagac ccaggtgggc | 3480 |
| gactcaagga | tttgattttc | tacaagcaat | tgaacctgcc | tttatttcag ctttaccaga | 3540 |
| agatgacttc | ttgagtttac | aagccttgat | gaatgaatgc | attggccatg tcataggaaa | 3600 |
| accacacagt | cctgttacag | gtttgtacct | tgccattcat | cggaacagcc ccgtcctat | 3660 |
| gaaggtacct | cgatgccata | gtgaccctcc | taacccacac | ctcattatcc ccactccaga | 3720 |
| gggattcagc | actcggagca | tgccttccga | cgcgcggagc | catggcagcc ctgctgctgc | 3780 |
| tgctgctgct | gctgctgctg | ctgttgctgc | cagtcggccc | agcccctctg gtggtgactc | 3840 |
| tgtgctgccc | aaatccatca | gcagtgccca | tgataccagg | ggttccagcg ttcctgaaaa | 3900 |
| tgatcgattg | gcttccatag | ctgctgaatt | gcagtttagg | tccctgagtc gtcactcaag | 3960 |
| ccccacggag | gagcgagatg | aaccagcata | tccaagagga | gattcaagtg ggtccacaag | 4020 |
| aagaagttgg | gaacttcgga | cactaatcag | ccagagtaaa | gatactgctt ctaaaactagg | 4080 |
| acccatagaa | gctatccaga | agtcagtccg | attgtttgaa | gaaaagaggt accgagaaat | 4140 |

```
gaggagaaag aatatcattg gtcaagtttg tgatacgcct aagtcctatg ataatgttat    4200
gcacgttggc ttgaggaagg tgaccttcaa atggcaaaga ggaaacaaaa ttggagaagg    4260
ccagtatggg aaggtgtaca cctgcatcag cgtcgacacc ggggagctga tggccatgaa    4320
agagattcga tttcaaccta atgaccataa gactatcaag gaaactgcag acgaattgaa    4380
aatattcgaa ggcatcaaac accccaatct ggttcggtat tttggtgtgg agctccatag    4440
agaagaaatg tacatcttca tggagtactg cgatgagggg actttagaag aggtgtcaag    4500
gctgggactt caggaacatg tgattaggct gtattcaaag cagatcacca ttgcgatcaa    4560
cgtcctccat gagcatggca tagtccaccg tgacattaaa ggtgccaata tcttccttac    4620
ctcatctgga ttaatcaaac tgggagattt tggatgttca gtaaagctca aaaacaatgc    4680
ccagaccatg cctggtgaag tgaacagcac cctggggaca gcagcataca tggcacctga    4740
agtcatcact cgtgccaaag gagagggcca tgggcgtgcg gccgacatct ggagtctggg    4800
gtgtgttgtc atagagatgg tgactggcaa gaggccttgg catgagtatg agcacaactt    4860
tcaaattatg tataaagtgg ggatgggaca taagccacca atccctgaaa gattaagccc    4920
tgaaggaaag gacttccttt ctcactgcct tgagagtgac ccaaagatga gatggaccgc    4980
cagccagctc ctcgaccatt cgtttgtcaa ggtttgcaca gatgaagaat gaagcctagt    5040
agaatatgga cttggaaaat tctcttaatc actactgtat gtaatattta cataaagact    5100
gtgctgagaa gcagtataag cctttttaac cttccaagac tgaagactgc acaggtgaca    5160
agcgtcactt ctcctgctgc tcctgtttgt ctgatgtggc aaaaggccct ctggagggct    5220
ggtggccacg aggttaaaga agctgcatgt taagtgccat tactactgta cacggaccat    5280
cgcctctgtc tcctccgtgt ctcgcgcgac tgagaaccgt gacatcagcg tagtgttttg    5340
acctttctag gttcaaaaga agttgtagtg ttatcaggcg tcccatacct tgtttttaat    5400
ctcctgtttg ttgagtgcac tgactgtgaa acctttacct ttttttgttgt tgttggcaag    5460 ctgcaggttt gtaatgcaaa aggctgatta ctgaaattta agaaaaaggt tctttttca    5520 ataaatggtt tattttagga aagctcaaaa aaaaaaaaaa aaaa                    5564

<210> SEQ ID NO 9
<211> LENGTH: 11
<212> TYPE: DNA
<213> ORGANISM: Homo sapiens

<400> SEQUENCE: 9
gaggtygtgg g                                                           11

<210> SEQ ID NO 10
<211> LENGTH: 11
<212> TYPE: DNA
<213> ORGANISM: Homo sapiens

<400> SEQUENCE: 10
ggctcygccg t                                                           11

<210> SEQ ID NO 11
<211> LENGTH: 11
<212> TYPE: DNA
<213> ORGANISM: Homo sapiens

<400> SEQUENCE: 11
tggccytcag c                                                           11
```

```
<210> SEQ ID NO 12
<211> LENGTH: 11
<212> TYPE: DNA
<213> ORGANISM: Homo sapiens

<400> SEQUENCE: 12
ccatgsctct g                                                        11

<210> SEQ ID NO 13
<211> LENGTH: 11
<212> TYPE: DNA
<213> ORGANISM: Homo sapiens

<400> SEQUENCE: 13
tcggaygact c                                                        11

<210> SEQ ID NO 14
<211> LENGTH: 11
<212> TYPE: DNA
<213> ORGANISM: Homo sapiens

<400> SEQUENCE: 14
ttcttwcagg c                                                        11

<210> SEQ ID NO 15
<211> LENGTH: 11
<212> TYPE: DNA
<213> ORGANISM: Homo sapiens

<400> SEQUENCE: 15
ctaaakgcca t                                                        11

<210> SEQ ID NO 16
<211> LENGTH: 11
<212> TYPE: DNA
<213> ORGANISM: Homo sapiens

<400> SEQUENCE: 16
ttccawttgg c                                                        11

<210> SEQ ID NO 17
<211> LENGTH: 11
<212> TYPE: DNA
<213> ORGANISM: Homo sapiens

<400> SEQUENCE: 17
tggccyagga g                                                        11

<210> SEQ ID NO 18
<211> LENGTH: 11
<212> TYPE: DNA
<213> ORGANISM: Homo sapiens

<400> SEQUENCE: 18
cccttrttat t                                                        11

<210> SEQ ID NO 19
<211> LENGTH: 11
<212> TYPE: DNA
<213> ORGANISM: Homo sapiens

<400> SEQUENCE: 19
actaaycaaa t                                                        11
```

```
<210> SEQ ID NO 20
<211> LENGTH: 11
<212> TYPE: DNA
<213> ORGANISM: Homo sapiens

<400> SEQUENCE: 20
aaatgrcgag g                                                        11

<210> SEQ ID NO 21
<211> LENGTH: 11
<212> TYPE: DNA
<213> ORGANISM: Homo sapiens

<400> SEQUENCE: 21
gagctrtaga t                                                        11

<210> SEQ ID NO 22
<211> LENGTH: 11
<212> TYPE: DNA
<213> ORGANISM: Homo sapiens

<400> SEQUENCE: 22
gtttcsaaac c                                                        11

<210> SEQ ID NO 23
<211> LENGTH: 11
<212> TYPE: DNA
<213> ORGANISM: Homo sapiens

<400> SEQUENCE: 23
tctttytatt t                                                        11

<210> SEQ ID NO 24
<211> LENGTH: 69
<212> TYPE: DNA
<213> ORGANISM: Mus musculus
<220> FEATURE:
<221> NAME/KEY: CDS
<222> LOCATION: (1)..(66)

<400> SEQUENCE: 24 act tca gac gca cac agg ttg gca ctg cca tct ctg ctg ctt ctg act    48
Thr Ser Asp Ala His Arg Leu Ala Leu Pro Ser Leu Leu Leu Leu Thr
 1               5                  10                  15 cca ctg ctg tgg ggc ctg tga                                         69
Pro Leu Leu Trp Gly Leu
            20

<210> SEQ ID NO 25
<211> LENGTH: 96
<212> TYPE: DNA
<213> ORGANISM: Mus musculus
<220> FEATURE:
<221> NAME/KEY: CDS
<222> LOCATION: (1)..(93)

<400> SEQUENCE: 25 act tca gac gca cac agg ttg gca ctg cca tct ctg ctg ctt ctg act    48
Thr Ser Asp Ala His Arg Leu Ala Leu Pro Ser Leu Leu Leu Leu Thr
 1               5                  10                  15 cca ctg ctg tgg ggc ctg tgg acc tca gtc tct gcc aag gca tcc tga    96
Pro Leu Leu Trp Gly Leu Trp Thr Ser Val Ser Ala Lys Ala Ser
            20                  25                  30
```

```
<210> SEQ ID NO 26
<211> LENGTH: 102
<212> TYPE: DNA
<213> ORGANISM: Homo sapiens
<220> FEATURE:
<221> NAME/KEY: CDS
<222> LOCATION: (1)..(99)

<400> SEQUENCE: 26 ccg ggg gcc cca ggc cca ctg gtg gct gcc acc atg ctg ctg ctg         48
Pro Gly Ala Pro Gly Pro Leu Val Ala Ala Thr Met Leu Leu Leu
1               5                   10                  15 ccg cca ctg tca cca ggc gcc ctg tgg aca gcg gcc cag gcc ctg acg     96
Pro Pro Leu Ser Pro Gly Ala Leu Trp Thr Ala Ala Gln Ala Leu Thr
                20                  25                  30 cta tga                                                            102
Leu

<210> SEQ ID NO 27
<211> LENGTH: 22
<212> TYPE: PRT
<213> ORGANISM: Mus musculus

<400> SEQUENCE: 27

Thr Ser Asp Ala His Arg Leu Ala Leu Pro Ser Leu Leu Leu Thr
1               5                   10                  15

Pro Leu Leu Trp Gly Leu
                20

<210> SEQ ID NO 28
<211> LENGTH: 31
<212> TYPE: PRT
<213> ORGANISM: Mus musculus

<400> SEQUENCE: 28

Thr Ser Asp Ala His Arg Leu Ala Leu Pro Ser Leu Leu Leu Thr
1               5                   10                  15

Pro Leu Leu Trp Gly Leu Trp Thr Ser Val Ser Ala Lys Ala Ser
                20                  25                  30

<210> SEQ ID NO 29
<211> LENGTH: 33
<212> TYPE: PRT
<213> ORGANISM: Homo sapiens

<400> SEQUENCE: 29

Pro Gly Ala Pro Gly Pro Leu Val Ala Ala Thr Met Leu Leu Leu
1               5                   10                  15

Pro Pro Leu Ser Pro Gly Ala Leu Trp Thr Ala Ala Gln Ala Leu Thr
                20                  25                  30

Leu
```

MAP KINASE PATHWAY TARGETS FOR THE TREATMENT OF MARFAN SYNDROME

CROSS REFERENCE TO RELATED APPLICATION(S)

The present application is the U.S. National Phase of International Application No. PCT/US2018/020692, filed Mar. 2, 2018, which claims the benefit of U.S. Provisional Patent Application No. 62/466,197 filed Mar. 2, 2017, the entire contents of which are incorporated by reference herein.

GOVERNMENT SUPPORT

This invention was made with government support under grant AR041135 awarded by the National Institutes of Health. The government has certain rights in the invention.

BACKGROUND

Marfan syndrome (MFS) is a systemic connective tissue disorder with autosomal dominant inheritance, caused by mutations in the FBN1 gene. It has cardinal features involving the ocular, skeletal and cardiovascular systems, with the major cause of mortality resulting from aortic root dilatation, dissection and rupture.

Many of the features of Marfan syndrome are common in the general population and represent a tremendous public health burden. These include aortic aneurysm (1-2% of the population at large), mitral valve prolapse (~7%), emphysema (11%), scoliosis (0.5%), cataract (30%), arthritis (very common), and myopathy (many common genetic and acquired forms).

SUMMARY

As described below, the present disclosure features compositions and methods for the treatment of Marfan syndrome diseases and disorders.

In one aspect, the instant disclosure provides a method for treating a subject having or at risk of developing Marfan Syndrome or a Marfan-associated condition involving administering to the subject an effective amount of an agent that modulates the activity of MAP kinase pathway signaling, thereby treating the subject.

In one embodiment, the agent that modulates the activity of MAP kinase pathway signaling is a MAP kinase pathway inhibitor. In certain embodiments, the agent that modulates the activity of MAP kinase pathway signaling is an inhibitor of MMP17, MAP2K6 or MAP3K4, or of a gene product thereof. Optionally, the inhibitor of MMP17, MAP2K6 or MAP3K4, or of a gene product thereof, is an antisense agent or a double-stranded nucleic acid, optionally a siRNA or shRNA specific for MMP17, MAP2K6 or MAP3K4.

In certain embodiments, the inhibitor of MMP17, MAP2K6 or MAP3K4, or of a gene product thereof, is specific for a nucleic acid molecule having at least a 50% sequence identity to SEQ ID NO: 2, SEQ ID NO: 4, SEQ ID NO: 6 or SEQ ID NO: 8.

In certain embodiments, the inhibitor of MMP17, MAP2K6 or MAP3K4, or of a gene product thereof, is specific for a nucleic acid molecule set forth as SEQ ID NO: 2, SEQ ID NO: 4, SEQ ID NO: 6 or SEQ ID NO: 8.

In another embodiment, the agent that modulates the activity of MAP kinase pathway signaling is a small molecule. Optionally, the agent that modulates the activity of MAP kinase pathway signaling comprise Batimastat, GI 254023X, GM 6001, TMI 1, WAY 170523, WX-554 or combinations thereof.

In certain embodiments, the agent that modulates the activity of MAP kinase pathway signaling is an antibody.

In some embodiments, the Marfan syndrome-associated disease or disorder is a clinical condition associated with Marfan syndrome. Optionally, the disease or disorder is an aneurysm, an aortic aneurysm, or emphysema. In certain embodiments, the disease or disorder is an aneurysm.

Another aspect of the disclosure provides a method for treating a subject having Marfan syndrome or a Marfan-associated condition involving identifying a variant allele of MMP17, MAP2K6 or MAP3K4 that produces elevated expression and/or activity of a gene product of the MMP17, MAP2K6 or MAP3K4 gene; and replacing the variant allele of MMP17, MAP2K6 or MAP3K4 with an allele of MMP17, MAP2K6 or MAP3K4 that does not produce elevated expression and/or activity of a gene product of the MMP17, MAP2K6 or MAP3K4 gene, thereby treating the subject.

In one embodiment, the step of replacing the variant allele is performed via a CRISPR-Cas9 gene replacement process. Optionally, the step of replacing is performed ex vivo. In a related embodiment, re-introduction to the subject of a cell manipulated ex vivo to perform gene replacement treats the subject.

In certain embodiments, the variant allele of MMP17, MAP2K6 or MAP3K4 that produces elevated expression and/or activity of a gene product of the MMP17, MAP2K6 or MAP3K4 gene comprises a nucleic acid sequence having at least a 50% sequence identity to SEQ ID NOS: 9, 10, 11, 12, 13, 14, 15, 16, 17, 18, 19, 20, 21, 22 or 23.

In certain embodiments, the variant allele of MMP17, MAP2K6 or MAP3K4 that produces elevated expression and/or activity of a gene product of the MMP17, MAP2K6 or MAP3K4 gene comprise nucleic acid sequences set forth as SEQ ID NOS: 9, 10, 11, 12, 13, 14, 15, 16, 17, 18, 19, 20, 21, 22 or 23.

An additional aspect of the disclosure provides a pharmaceutical composition for the treatment of a disease or disorder characterized by aberrant MAP kinase pathway expression or activity, where the pharmaceutical composition includes an agent that modulates the activity of MMP17, MAP2K6 or MAP3K4, or of a gene product thereof.

A further aspect of the disclosure provides a kit for identifying a subject having or at risk of developing Marfan Syndrome or a Marfan-associated condition that includes primers specific for amplification of MMP17, MAP2K6 and/or MAP3K4; a probe oligonucleotide, optionally fluorescently labeled, that specifically detects the presence of a MMP17, MAP2K6 and/or MAP3K4 amplicon, wherein detection of elevated expression of MMP17, MAP2K6 and/or MAP3K4 identifies the subject as having or at risk of developing Marfan Syndrome or a Marfan-associated condition; and instructions for use.

In certain embodiments, the kit further includes a pharmaceutical composition of the instant disclosure.

Another aspect of the disclosure provides a method for identifying and treating a subject having or at risk of developing Marfan Syndrome or a Marfan-associated condition involving: isolating a sample from the subject; assessing the expression level of MMP17, MAP2K6 and/or MAP3K4 in the sample, assessing the level of activity of a gene product of MMP17, MAP2K6 and/or MAP3K4 in the sample, and/or genotyping MMP17, MAP2K6 and/or MAP3K4 in the sample; identifying elevated expression of MMP17, MAP2K6 and/or MAP3K4 in the sample, identifying elevated activity of a gene product of MMP17, MAP2K6 and/or MAP3K4 in the sample, and/or identifying a genotype of MMP17, MAP2K6 and/or MAP3K4 in the sample that causes elevated expression and/or activity of MMP17, MAP2K6 and/or MAP3K4, or of a gene product thereof; and administering a therapy for Marfan Syndrome or a Marfan-associated condition to the subject, thereby treating the subject.

In certain embodiments, a method for treating a subject having or at risk of developing Marfan Syndrome or a Marfan-associated condition comprises administering to the subject an effective amount of an agent that modulates the activity of MAP kinase pathway signaling and/or expression, function or activity of epidermal growth factor receptor (EGFR); thereby treating the subject.

In certain embodiments, the therapy for Marfan Syndrome or a Marfan-associated condition comprises administration of a TGFβ NAb, losartan and/or an inhibitor of MMP17, MAP2K6 and/or MAP3K4, or of a gene product thereof.

DEFINITIONS

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By the terms "conjugated," "linked," "attached," "fused" and "tethered," when used with respect to two or more moieties, means that the moieties or domains are physically associated or connected with one another, either directly or via one or more additional moieties that serve as a linking agent, to form a structure that is sufficiently stable so that the moieties remain physically associated under the conditions in which the structure is used, e.g., physiological conditions. The linkage can be based on genetic fusion according to the methods known in the art or can be performed by, e.g., chemical cross-linking. The compounds and targeting agents may be linked by a flexible linker, such as a polypeptide linker or a synthetic linker. The polypeptide linker can comprise plural, hydrophilic or peptide-bonded amino acids of varying lengths. The term "associated" will be used for the sake of brevity and is meant to include all possible methods of physically associating each compound with one or more desired molecules or agents.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens. The detectable label is associated with a composition of interest by any possible methods of physically associating each compound to a detectable label.

By "disease" is meant any condition or disorder that damages or interferes with the normal function of a cell, tissue, or organ. Examples of diseases include Marfan Syndrome.

As used herein, the term "EGFR inhibitor" is intended to include therapeutic agents that inhibit, downmodulate, suppress or downregulate EGFR signaling activity. The term is intended to include chemical compounds, such as small molecule inhibitors (e.g., small molecule tyrosine kinase inhibitors) and biologic agents, such as antibodies, interfering RNA (shRNA, siRNA), soluble receptors and the like.

By "effective amount" is meant the amount of a required to ameliorate the symptoms of a disease relative to an untreated patient. The effective amount of active compound(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The disclosure provides a number of targets that are useful for the development of highly specific drugs to treat or a disorder characterized by the methods delineated herein. In addition, the methods of the disclosure provide a facile means to identify therapies that are safe for use in subjects. In addition, the methods of the disclosure provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the disclosure, but which does not substantially recognize and bind other molecules in a sample, for example, a biological sample, which naturally includes a polypeptide of the disclosure.

Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) *Methods Enzymol.* 152:399; Kimmel, A. R. (1987) *Methods Enzymol.* 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A: Aortic root size (mm) in BL6 (n=16) and 129 (n=13) wild-type (WT) mice, and BL6 (n=15) and 129 (n=15) Fbn1$^{C1039G/+}$ (MFS) mice at 2 and 6 months of age, and postnatal aortic root growth (mm) from 2 to 6 months; FIG. 1B: Representative parasternal long axis echocardiograms at 6 months of the aortic root (yellow arrow) and ascending aorta (red arrow) in WT and MFS mice on BL6 and 129 strains; FIG. 1C: Survival curve to 10 months for WT and MFS mice on pure BL6 and 129 strains. *<0.05, **<0.01, †<0.001, ††<0.0001, †††<0.00001, NS non-significant.

FIG. 2A: Western blot analysis of the aortic root of 4 WT and 4 MFS mice on BL6 and 129 strains at 10 months of age; FIG. 2B: Aortic root growth (mm) from 2 to 6 months in placebo- (n=12) and losartan-treated (n=9) 129 WT mice, and placebo- (n=1) and losartan-treated (n=8) 129 MFS mice; Aortic root growth from 2 to 4 months in placebo-(n=13) and RDEA119-treated (n=5) 129 WT mice, and placebo- (n=13) and RDEA119-treated (n=10) 129 MFS mice; FIG. 2C: Survival curve up to 8 months of treatment in placebo- and losartan-treated 129 WT and MFS mice; FIG. 2D: Western blot analysis of the aortic root of 3 placebo- and 3 losartan-treated 129 WT and MFS mice at 10 months of age;

FIG. 2E: Western blot analysis of the aortic root of 3 placebo- and 3 RDEA119-treated 129 WT and MFS mice at 4 months of age. Plac: placebo; Los: losartan; RDEA: RDEA119. *<0.05, **<0.01, †<0.001, ††<0.0001, †††<0.00001, NS non-significant.

FIG. 3A: Single QTL genome scan of intercrossed MFS mice that possessed either a 'BL6-like' aortic root size (<2.20 mm; n=35) or a '129-like' aortic root size (>2.70 mm; n=40) at 6 months of age; genome wide significance LOD score of 3.82 is indicated by the red line; 2 loci exceeded this threshold, with individual LOD scores and adjusted p-values indicated; FIG. 3B: Aortic root size (mm) at 6 months of age in F2 generation intercrossed BL6/129 MFS mice, stratified by number of 129 alleles in the 2 regions of interest (average n per group=13); FIG. 3C: Aortic root size (mm) at 6 months of age in MFS mice lacking either one or two functional Mmp17 and Map2k6 alleles (n>10 per group); FIG. 3D: Western blot analysis of the aortic root at 10 months of age in 3 WT mice, 3 pure 129 MFS mice, 3 pure BL6 MFS mice, and 3 MFS mice either retaining (+/+) or lacking (−/−) functional Mmp17 and Map2k6 alleles; FIG. 3E: Western blot analysis of Egfr activation in the aortic root at 10 months of age in 4 pure BL6 and pure 129 WT and MFS mice, as well as 3 MFS mice either retaining (+/+) or lacking (−/−) functional Mmp17 and Map2k6 alleles; FIG. 3F: Aortic root growth (mm) from 2 to 4 months of age in placebo-(n=12) and erlotinib-treated (n=6) 129 WT mice, and placebo- (n=1) and erlotinib-treated (n=1) 129 MFS mice; FIG. 3G: Western blot analysis at 4 months of age in 3 placebo- and 3 erlotinib-treated 129 WT and MFS mice. Chr: Chromosome; M17: Mmp17; M2: Map2k6; Plac: placebo; Erlo: erlotinib. *<0.05, **<0.01, †<0.001, ††<0.0001, NS non-significant.

FIG. 4A: Pedigrees of 5 MFS families recruited for genome wide linkage analysis; yellow indicates MFS patients with mild aortic disease, black indicates MFS patients with severe aortic disease, grey indicates patients with indeterminate data, and white indicates family members who do not have MFS; FIG. 4B: Parametric linkage analysis revealed 1 locus that surpassed a genome wide significance LOD score of 3.3, which is indicated by the red line; FIG. 4C: Quantitative PCR analysis of MAP3K4 mRNA expression from cultured dermal fibroblasts of 2 controls, 2 MFS patients from family B with mild aortic disease and 2 MFS patients from family B with severe aortic disease; all biological samples were run in experimental triplicate and normalized to β-actin; FIG. 4D: Aortic root growth from 2 to 6 months of age in WT mice either retaining (+/+; n=12) or haploinsufficient (+/−n=7) for Map3k4, and MFS mice either retaining (n=8) or haploinsufficient (n=7) for Map3k4; FIG. 4E: Western blot analysis of the aortic root at 10 months of age in 3 WT and 3 MFS mice either retaining or haploinsufficient for Map3k4. M3k4: Map3k4; *<0.05, **<0.01, †<0.001, NS non-significant

FIG. 11 shows the Mmp17 C-terminal DNA and amino acid sequences, illustrating the 9 amino acid truncation in the BL6 mouse strain (SEQ ID NO: 24) relative to the 129 strain (SEQ ID NO: 25). The human MMP17 sequences (SEQ ID NO: 26) are displayed for comparison. The DNA sequence highlighted in red identifies the 129 codon that corresponds to the BL6 stop codon. The amino acid highlighted in red represents the predicted start site of the GPI anchor in each sequence.

DETAILED DESCRIPTION

Figure 1A:
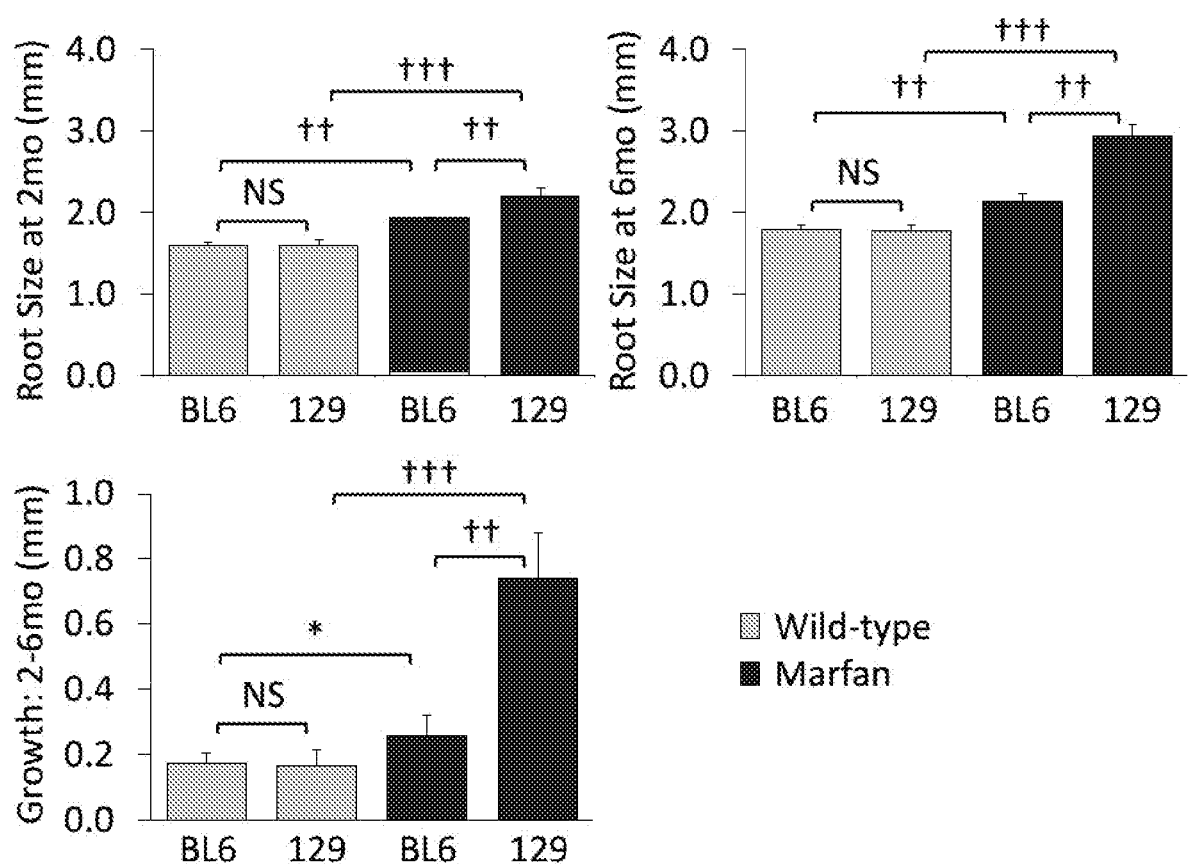
FIGS. 1A-1C show the aortic phenotype of pure C57BL/6J (BL6) and 129S6/SvEvTac (129) mice.

A need exists for methods and compositions for the diagnosis and treatment of Marfan syndrome and associated diseases, disorders and conditions.

The instant disclosure is based, at least in part, upon the discovery that upregulation of expression and/or activity of certain MAP kinase pathway components drives Marfan Syndrome (MFS) development in a mouse model of Marfan Syndrome. Genetic backcrosses were performed between mice of an MFS model and a non-MFS-afflicted strain of mice, thereby identifying genetic loci associated with MFS. In particular, loci that caused elevated expression and/or activity of MMP17, MAP2K6 or MAP3K4, or of gene products thereof, were identified as contributing to MFS and related conditions in such mice. Modulation of MAP kinase pathway signaling, and particularly inhibition and/or gene replacement of MMP17, MAP2K6 and/or MAP3K4, or of gene products thereof, is thereby discovered to be a therapeutic approach for MFS. MFS diagnosis is also aided by this identification of MAP kinase pathway signaling components/loci indicative of development of MFS in a subject.

Marfan Syndrome (MFS)

Marfan syndrome (MFS) is an autosomal dominant connective tissue disorder that includes a predisposition for aortic root aneurysm and aortic rupture. MFS is caused by a deficiency of the microfibrillar constituent protein fibrillin 1 that is imposed by heterozygous mutations in FBN1.

Marfan syndrome (MFS) is a systemic disorder with autosomal dominant inheritance and a prevalence of approximately 1 per 5,000 population (Pyeritz, R. E. & McKusick, V. A. (1979) *N Engl J Med.* 300, 772-777). The syndrome shows no racial preference and both sexes are affected equally. It has been estimated that 25% of cases occur due to spontaneous mutations. While this condition shows high penetrance, marked interfamilial clinical variability is the rule (Pyeritz, R. E. et al. (1979) *Birth Defects Orig Artic Ser.* 15, 155-178). Historic lack of a specific biochemical or genetic marker of disease, coupled with the variability in clinical presentation, has frustrated diagnosis of equivocal cases and has likely contributed to a significant underestimation of the prevalence of disease.

The cardinal features of this disorder involve the ocular, skeletal, and cardiovascular systems. Cardiovascular pathology, including aortic root dilatation, dissection, and rupture, pulmonary artery dilatation, myxomatous valve changes with insufficiency of the mitral and aortic valves, and progressive myocardial dysfunction, is the leading cause of mortality in the MFS. The majority of fatal events associated with untreated MFS occur in early adult life. In a prospective study of 72 patients in 1972, the average age of death was 32 years (Murdoch, J. L. et al. (1972) *N Engl J Med.* 286, 804-808).

Skeletal involvement is evident in nearly all people with MFS. Progressive anterior chest deformity or scoliosis can cause cardiopulmonary dysfunction and commonly require surgical correction. Joint instability can cause physical disability and predispose to premature arthritis. Lung disease most commonly manifests with spontaneous pneumothorax and has been identified in 4-11% of MFS patients (Wood, J. R., et al. (1984) *Thorax.* 39, 780-784; Hall, J. R., et al. (1984) *Ann Thorac Surg.* 37, 500-504).

Many of the features of Marfan syndrome are common in the general population and represent a tremendous public health burden. These include aortic aneurysm (1-2% of the population at large), mitral valve prolapse (~7%), emphysema (11%), scoliosis (0.5%), cataract (30%), arthritis (very common), and myopathy (many common genetic and acquired forms).

Previous work has implicated enhanced TGFβ signaling in MFS disease pathogenesis. In Fbn1$^{C1039G/+}$ mice (hereafter termed MFS mice), a well-validated model of MFS, multiple phenotypic manifestations, including aortic aneurysm, developmental emphysema, mitral valve disease and skeletal muscle myopathy, can be attenuated by administration of TGFβ neutralizing antibody (TGFβ NAb) or the angiotensin-II (Ang-II) type 1 receptor blocker (ARB) losartan, in association with blunted Smad2/3 activation (Habashi et al., Science 312, 117; Neptune et al., *Nature Genetics* 33, 407; Ng et al., Journal Clinical Investigation 114, 1586; Cohn et al., Nature Medicine 13, 204).

It is well-recognized that the severity of aortic disease and other systemic manifestations in patients with MFS is highly variable. While the causes for this are not well understood, there is clearly a strong genetic component, since members of the same family often share similar manifestations and outcomes. Despite this, there is very limited correlation between the type or location of a patient's FBN1 mutation and their disease. This implies that there may be other major modifier genes which determine the penetrance and/or severity of a patient's disease.

A need exists for methods and compositions for the treatment of Marfan syndrome and associated diseases, disorders and conditions, e.g., diseases, disorders and conditions associated with aberrant MAP kinase pathway component expression and/or activity.

MAP Kinase Pathway Signaling

A mitogen-activated protein kinase (MAPK or MAP kinase) is a type of protein kinase that is specific to the amino acids serine, threonine, and tyrosine (i.e., a serine/threonine-specific protein kinase). MAPKs are involved in directing cellular responses to a diverse array of stimuli, such as mitogens, osmotic stress, heat shock and proinflammatory cytokines. They regulate cell functions including proliferation, gene expression, differentiation, mitosis, cell survival, and apoptosis (Pearson G, et al. (April 2001). *Endocrine Reviews*. 22 (2): 153-83).

MAP kinases are found in eukaryotes only, but they are fairly diverse and encountered in all animals, fungi and plants, and even in an array of unicellular eukaryotes.

MAPKs belong to the CMGC (CDK/MAPK/GSK3/CLK) kinase group. The closest relatives of MAPKs are the cyclin-dependent kinases (CDKs; Manning G, et al. (December 2002). *Science*. 298 (5600): 1912-34)).

The first mitogen-activated protein kinase to be discovered was ERK1 (MAPK3) in mammals. Since ERK1 and its close relative ERK2 (MAPK1) are both involved in growth factor signaling, the family was termed "mitogen-activated". With the discovery of other members, even from distant organisms (e.g. plants), it has become increasingly clear that the name is a misnomer, since most MAPKs are actually involved in the response to potentially harmful, abiotic stress stimuli (hyperosmosis, oxidative stress, DNA damage, low osmolarity, infection, etc.). Because plants cannot "flee" from stress, terrestrial plants have the highest number of MAPK genes per organism ever found. Thus the role of mammalian ERK1/2 kinases as regulators of cell proliferation is not a generic, but a highly specialized function.

Most MAPKs have a number of shared characteristics, such as the activation dependent on two phosphorylation events, a three-tiered pathway architecture and similar substrate recognition sites. These are the "classical" MAP kinases. But there are also some ancient outliers from the group as sketched above, that do not have dual phosphorylation sites, only form two-tiered pathways, and lack the features required by other MAPKs for substrate binding. These are usually referred to as "atypical" MAPKs (Coulombe P, Meloche S (August 2007). *Biochimica et Biophysica Acta*. 1773 (8): 1376-87). It is yet unclear if the atypical MAPKs form a single group as opposed to the classical ones.

Mitogen-activated protein kinases are catalytically inactive in their base form. In order to become active, they require (potentially multiple) phosphorylation events in their activation loops. This is conducted by specialized enzymes of the STE protein kinase group.

In the case of classical MAP kinases, the activation loop contains a characteristic TxY (threonine-x-tyrosine) motif (TEY in mammalian ERK1 and ERK2, TDY in ERK5, TPY in JNKs, TGY in p38 kinases) that needs to be phosphorylated on both the threonine and the tyrosine residues in order to lock the kinase domain in a catalytically competent conformation. In vivo and in vitro, phosphorylation of tyrosine precedes phosphorylation of threonine, although phosphorylation of either residue can occur in the absence of the other.

This tandem activation loop phosphorylation (that was proposed to be either distributive or processive, dependent on cellular environment) is performed by members of the Ste7 protein kinase family, also known as MAP2 kinases. MAP2 kinases in turn, are also activated by phosphorylation, by a number of different upstream serine-threonine kinases (MAP3 kinases). Because MAP2 kinases display very little activity on substrates other than their cognate MAPK, classical MAPK pathways form multi-tiered, but relatively linear pathways. These pathways can effectively convey stimuli from the cell membrane (where many MAP3Ks are activated) to the nucleus (where only MAPKs may enter) or to many other subcellular targets.

In comparison to the three-tiered classical MAPK pathways, some atypical MAP kinases appear to have a more ancient, two-tiered system. ERK3 (MAPK6) and ERK4 (MAPK4) were recently shown to be directly phosphorylated and thus activated by PAK kinases (related to other MAP3 kinases; Déléris P, et al. (February 2011). *The Journal of Biological Chemistry*. 286 (8): 6470-8). In contrast to the classical MAP kinases, these atypical MAPKs require only a single residue in their activation loops to be phosphorylated. The details of NLK and ERK7 (MAPK15) activation remain unknown.

Inactivation of MAPKs is performed by a number of phosphatases. A very conserved family of dedicated phosphatases is the so-called MAP kinase phosphatases (MKPs), a subgroup of dual-specificity phosphatases (DUSPs; Theodosiou A, Ashworth A (June 2002). *Genome Biology*. 3 (7): reviews3009.1-reviews3009.10). As their name implies, these enzymes are capable of hydrolyzing the phosphate from both phosphotyrosine and the phosphothreonine residues. Since removal of either phosphate groups will greatly reduce MAPK activity, essentially abolishing signaling, some tyrosine phosphatases are also involved in inactivating MAP kinases (e.g. the phosphatases HePTP, STEP and PTPRR in mammals).

As mentioned above, MAPKs typically form multi-tiered pathways, receiving input several levels above the actual MAP kinase. In contrast to the relatively simple, phosphorylation-dependent activation mechanism of MAPKs and MAP2Ks, MAP3Ks have stunningly complex regulation. Many of the better-known MAP3Ks, such as c-Raf, MEKK4 or MLK3 require multiple steps for their activation. These are typically allosterically-controlled enzymes, tightly locked into an inactive state by multiple mechanisms. The first step en route to their activation consists of relieving their auto-inhibition by a smaller ligand (such as Ras for c-Raf, GADD45 for MEKK4 (Miyake Z, et al. (April 2007). *Molecular and Cellular Biology*. 27 (7): 2765-76) or Cdc42 for MLK3 (Du Y, et al. (December 2005). *The Journal of Biological Chemistry*. 280 (52): 42984-93)). This commonly (but not always) happens at the cell membrane, where most of their activators are bound (note that small G-proteins are constitutively membrane-associated due to prenylation). That step is followed by side-to-side homo- and heterodimerization of their now accessible kinase domains. Recently determined complex structures reveal that the dimers are formed in an orientation that leaves both their substrate-binding regions free (Rajakulendran T, et al. (September 2009). *Nature*. 461 (7263): 542-5). Importantly, this dimerization event also forces the MAP3 kinase domains to adopt a partially active conformation. Full activity is only achieved once these dimers transphosphorylate each other on their activation loops. The latter step can also be achieved or aided by auxiliary protein kinases (MAP4 kinases, members of the Ste20 family). Once a MAP3 kinase is fully active, it may phosphorylate its substrate MAP2 kinases, which in turn will phosphorylate their MAP kinase substrates.

The ERK1/2 pathway of mammals is probably the best-characterized MAPK system. The most important upstream activators of this pathway are the Raf proteins (A-Raf, B-Raf or c-Raf), the key mediators of response to growth factors (EGF, FGF, PDGF, etc.); but other MAP3Ks such as c-Mos and Tpl2/Cot can also play the same role. All these enzymes phosphorylate and thus activate the MKK1 and/or MKK2 kinases, that are highly specific activators for ERK1 and ERK2. The latter phosphorylate a number of substrates important for cell proliferation, cell cycle progression, cell division and differentiation (RSK kinases, Elk-1 transcription factor, etc.).

In contrast to the relatively well-insulated ERK1/2 pathway, mammalian p38 and JNK kinases have most of their activators shared at the MAP3K level (MEKK1, MEKK4, ASK1, TAK1, MLK3, TAOK1, etc.). In addition, some MAP2K enzymes may activate both p38 and JNK (MKK4), while others are more specific for either JNK (MKK7) or p38 (MKK3 and MKK6). Due to these interlocks, there are very few if any stimuli that can elicit JNK activation without simultaneously activating p38 or reversed (Cargnello M, Roux P P (March 2011). *Microbiology and Molecular Biology Reviews.* 75 (1): 50-83). Both JNK and p38 signaling pathways are responsive to stress stimuli, such as cytokines, ultraviolet irradiation, heat shock, and osmotic shock, and are involved in adaptation to stress, apoptosis or cell differentiation. JNKs have a number of dedicated substrates that only they can phosphorylate (c-Jun, NFAT4, etc.), while p38s also have some unique targets (e.g. the MAPKAP kinases MK2 and MK3), ensuring the need for both in order to respond to stressful stimuli.

ERK5 is part of a fairly well-separated pathway in mammals. Its sole specific upstream activator MKK5 is turned on in response to the MAP3 kinases MEKK2 and MEKK3. The specificity of these interactions are provided by the unique architecture of MKK5 and MEKK2/3, both containing N-terminal PB 1 domains, enabling direct hetero-dimerization with each other (Nakamura K, Johnson G L (September 2003). *The Journal of Biological Chemistry.* 278 (39): 36989-92). The PB 1 domain of MKK5 also contributes to the ERK5-MKK5 interaction: it provides a special interface (in addition to the D-motif found in MKK5) through which MKK5 can specifically recognize its substrate ERK5 (Glatz G, et al. (March 2013). *The Journal of Biological Chemistry.* 288 (12): 8596-609). Although the molecular-level details are poorly known, MEKK2 and MEKK3 respond to certain developmental cues to direct endothelial formation and cardiac morphogenesis. While also implicated in brain development, the embryonic lethality of ERK5 inactivation due to cardiac abnormalities underlines its central role in mammalian vasculogenesis (Regan C P, et al. (July 2002). *Proc. Nat'l Acad. Sci. USA.* 99 (14): 9248-53). It is notable, that conditional knockout of ERK5 in adult animals is also lethal, due to the widespread disruption of endothelial barriers (Hayashi M, Lee J D (December 2004). Journal of Molecular Medicine. 82 (12): 800-8). Mutations in the upstream components of the ERK5 pathway (the CCM complex) are thought to underlie cerebral cavernous malformations in humans.

As typical for the CMGC kinase group, the catalytic site of MAP kinases has a very loose consensus sequence for substrates. Like all their relatives, they only require the target serine/threonine amino acids to be followed by a small amino acid, preferably proline ("proline-directed kinases"). But as SP/TP sites are extremely common in all proteins, additional substrate-recognition mechanisms have evolved to ensure signaling fidelity (Garai A, et al. (October 2012). *Science Signaling.* 5 (245): ra74). Unlike their closest relatives, the cyclin-dependent kinases (CDKs), where substrates are recognized by the cyclin subunit, MAPKs associate with their substrates via auxiliary binding regions on their kinase domains. The most important such region consists of the hydrophobic docking groove and the negatively charged CD-region. Together they recognize the so-called MAPK docking or D-motifs (also called kinase interaction motif/KIM). D-motifs essentially consist of one or two positively charged amino acids, followed by alternating hydrophobic residues (mostly leucines), typically upstream of the phosphorylation site by 10-50 amino acids (Remenyi A, et al. (December 2005). *Mol. Cell.* 20 (6): 951-62). Many of the known MAPK substrates contain such D-motifs that can not only bind to, but also provide specific recognition by certain MAPKs. Interestingly, D-motifs are not restricted to substrates: MAP2 kinases also contain such motifs on their N-termini that are absolutely required for MAP2K-MAPK interaction and MAPK activation (Bardwell A J, et al. (May 2009). *The Journal of Biological Chemistry.* 284 (19): 13165-73). Similarly, both dual-specificity MAP kinase phosphatases and MAP-specific tyrosine phosphatases bind to MAP kinases through the same docking site (Goldsmith E J (December 2011). *Science Signaling.* 4 (204): pe47; Huang Z, Zhou B, Zhang Z Y (December 2004). *The Journal of Biological Chemistry.* 279 (50): 52150-9). D-motifs can even be found in certain MAPK pathway regulators and scaffolds (e.g. in the mammalian JIP proteins).

Other, less well characterized substrate-binding sites also exist. One such site (the DEF site) is formed by the activation loop (when in the active conformation) and the MAP kinase-specific insert below it. This site can accommodate peptides with an FxFP consensus sequence, typically downstream of the phosphorylation site (Sheridan D L, et al. (July 2008). *The Journal of Biological Chemistry.* 283 (28): 19511-20). Note that the latter site can only be found in proteins that need to selectively recognize the active MAP kinases, thus they are almost exclusively found in substrates. Different motifs may cooperate with each other, as in the Elk family of transcription factors, that possess both a D-motif and an FxFP motif. The presence of an FxFP motif in the KSR1 scaffold protein also serves to make it an ERK1/2 substrate, providing a negative feedback mechanism to set the correct strength of ERK1/2 activation.

Since the ERK signaling pathway is involved in both physiological and pathological cell proliferation, it is natural that ERK1/2 inhibitors would represent a desirable class of antineoplastic agents. Indeed, many of the proto-oncogenic "driver" mutations are tied to ERK1/2 signaling, such as constitutively active (mutant) receptor tyrosine kinases, Ras or Raf proteins. Although no MKK1/2 or ERK1/2 inhibitors were developed for clinical use, kinase inhibitors that also inhibit Raf kinases (e.g. Sorafenib) are successful antineoplastic agents against various types of cancer (Kim D H, Sim T (March 2012). *Arch. Pharmacol* Res. 35 (4): 605-15; Matsuda Y, Fukumoto M (December 2011). *Medical Molecular Morphology.* 44 (4): 183-9).

MMP17

The MMP17 gene encodes a member of the peptidase M10 family and membrane-type subfamily of matrix metalloproteinases (MMPs). Proteins in this family are involved in the breakdown of extracellular matrix in normal physiological processes, such as embryonic development, reproduction, and tissue remodeling, as well as in disease processes, such as arthritis and metastasis. Members of this subfamily contain a transmembrane domain suggesting that these proteins are expressed at the cell surface rather than secreted. The encoded preproprotein is proteolytically processed to generate the mature protease. This protein is unique among the membrane-type matrix metalloproteinases in that it is anchored to the cell membrane via a glycosylphosphatidylinositol (GPI) anchor. Elevated expression of the encoded protein has been observed in osteoarthritis and multiple human cancers.

An illustrative amino acid sequence (SEQ ID NO: 1) of human Mmp17 is NP_057239.4:

MRRRAARGPGPPPPGPGLSRLPLPLLLLLALGTRGGCAAPAPAPRAE
DLSLGVEWLSRFGYLPPADPTTGQLQTQEELSKAITAMQQFGGLEAT
GILDEATLALMKTPRCSLPDLPVLTQARRRRQAPAPTKWNKRNLSWR
VRTFPRDSPLGHDTVRALMYYALKVWSDIAPLNFHEVAGSAADIQID
FSKADHNDGYPFDGPGGTVAHAFFPGHHHTAGDTHFDDDEAWTFRSS
DAHGMDLFAVAVHEFGHAIGLSHVAAAHSIMRPYYQGPVGDPLRYGL
PYEDKVRVWQLYGVRESVSPTAQPEEPPLLPEPPDNRSSAPPRKDVP
HRCSTHFDAVAQIRGEAFFFKGKYFWRLTRDRHLVSLQPAQMHRFWR
GLPLHLDSVDAVYERTSDHKIVFFKGDRYWVFKDNNVEEGYPRPVSD
FSLPPGGIDAAFSWAHNDRTYFFKDQLYWRYDDHTRHMDPGYPAQSP
LWRGVPSTLDDAMRWSDGASYFFRGQEYWKVLDGELEVAPGYPQSTA
RDWLVCGDSQADGSVAAGVDAAEGPRAPPGQHDQSRSEDGYEVCSCT
SGASSPPGAPGPLVAATMLLLLPPLSPGALWTAAQALTL

The corresponding nucleic acid sequence (SEQ ID NO: 2) encoding human Mmp17 is NM_016155:

agtccggcggggcgccgcggagagcggagggcgccgggctgcggaa
cgcgaagcggagggcgcgggaccctgcacgccgcccgcgggcccatg
tgagcgccatgcggcgccgcgcagcccggggaccccggcccgccgccc
ccagggcccggactctcgcggctgccgctgccgctgctgctgctgct
ggcgctggggacccgcgggggctgcgccgcgcccgcacccgcgccgc
gcgccgaggacctcagcctgggagtggagtggctaagcaggacggtt
acctgccccggctgacccccacaacagggcagctgcagacgcaagag
gagctgtctaaggccatcacagccatgcagcagtaggtggcctggag
gccaccggcatcctggacgaggccaccctggccctgatgaaaacccc
acgctgctccctgccagacctccctgtcctgacccaggctcgcagga
gacgccaggctccagccccaccaagtggaacaagaggaacctgtcg
tggagggtccggacgacccacgggactcaccactggggcacgacacg
gtgcgtgcactcatgtactacgccctcaaggtctggagcgacattgc
gcccctgaacttccacgaggtggcgggcagcgccgccgacatccaga
tcgacactccaaggccgaccataacgacggctacccatcgacggccc
cggcggcaccgtggcccacgccacttccccggccaccaccacaccgc
cggggacacccactttgacgatgacgaggcctggaccaccgctcctc
ggatgcccacgggatggacctgatgcagtggctgtccacgagtaggc
cacgccattgggttaagccatgtggccgctgcacactccatcatgcg
gccgtactaccagggcccggtgggtgaccgctgcgctacgggctcc
cctacgaggacaaggtgcgcgtctggcagctgtacggtgtgcgggag
tctgtgtctcccacggcgcagcccgaggagcctcccctgctgccgga
gcccccagacaaccggtccagcgccccgcccaggaaggacgtgcccc acagatgcagcactcactttgacgcggtggcccagatccggggtgaa
gctttcttcttcaaaggcaagtacttctggcggctgacgcgggaccg
gcacctggtgtccctgcagccggcacagatgcaccgcactggcgggg
cctgccgctgcacctggacagcgtggacgccgtgtacgagcgcacca
gcgaccacaagatcgtcttctttaaaggagacaggtactgggtgttc
aaggacaataacgtagaggaaggatacccgcgcccgtctccgactt
cagcctcccgcctggcggcatcgacgctgccactcctgggcccacaa
tgacaggacttatttattaaggaccagctgtactggcgctacgatga
ccacacgaggcacatggacccggctaccccgcccagagcccctgt
ggaggggtgtcccagcacgctggacgacgccatgcgctggtccgac
ggtgcctcctacttcttccgtggccaggagtactggaaagtgctgga
tggcgagctggaggtggcacccgggtacccacagtccacggcccggg
actggctggtgtgtggagactcacaggccgatggatctgtggctgcg
ggcgtggacgcggcagaggggccccgcgcccctccaggacaacatga
ccagagccgctcggaggacggttacgaggtctgctcatgcacctctg
gggcatcctctccccgggggcccaggcccactggtggctgccacc
atgctgctgctgctgccgccactgtcaccaggcgccctgtggacagc
ggcccaggccctgacgctatgacacacagcgcgagcccatgagagga
cagaggcggtgggacagcctggccacagagggcaaggactgtgccgg
agtccctggggaggtgctggcgcgggatgaggacgggccaccctgg
caccggaaggccagcagagggcactgcccgccagggctgggcaggct
caggtggcaaggacggagctgtccctagtgagggactgtgttgact
gacgagccgaggggtggccgctccagaagggtgcccagtcaggccgc
accgccgccagcctcctccggccctggagggagcatctcgggctggg
ggcccacccctctctgtgccggcgccaccaacccccacccacactgct
gcctggtgctcccgccggcccacagggcctccgtccccaggtcccca
gtggggcagccctccccacagacgagccccccacatggtgccgcggc
acgtccccctgtgacgcgttccagaccaacatgacctctccctgct
ttgtaaaaaaaaaaaaaaaaaaa Known MMP17 inhibitors include those recited in Table 1.

TABLE 1

| MMP17 Inhibitors | | |
| --- | --- | --- |
| Compound | Action | Cas Number |
| Batimastat | Potent, broad spectrum MMP inhibitor | 130370-60-4 |
| GI 254023X | Selective ADAM10 metalloprotease inhibitor | 260264-93-5 |
| GM 6001 | Broad spectrum MMP inhibitor | 142880-36-2 |
| TMI 1 | Adam 17 (TACE) and MMP inhibitor; orally bioavailable | 287403-39-8 |
| WAY 170523 | Potent and selective inhibitor of MMP-13 | 307002-73-9 |

TABLE 2 dbSNP MMP17 Variants

| SNP ID | Chr 12 pos | Sequence Context | Type |
|---|---|---|---|
| rs7302578 | 131,831,385(+) | GAGGT(C/T)GTGGG (SEQ ID NO: 9) | intron-variant |
| rs7312725 | 131,849,044(+) | ggctc(C/T)gccgt (SEQ ID NO: 10) | intron-variant |
| rs7314389 | 131,829,208(+) | TGGCC(C/T)TCAGC (SEQ ID NO: 11) | intron-variant, upstream-variant-2KB |
| rs7484461 | 131,848,633(+) | ccatg(C/G)ctctg (SEQ ID NO: 12) | intron-variant |
| rs7484577 | 131,840,427(+) | TCGGA(C/T)GACTC (SEQ ID NO: 13) | intron-variant |

MAP2K6

Dual specificity mitogen-activated protein kinase kinase 6 also known as MAP kinase kinase 6 (MAPKK 6) or MAPK/ERK kinase 6 is an enzyme that in humans is encoded by the MAP2K6 gene, on chromosome 17 (Han J, et al. (February 1996). *The Journal of Biological Chemistry*. 271 (6): 2886-91).

MAPKK 6 is a member of the dual specificity protein kinase family, which functions as a mitogen-activated protein (MAP) kinase kinase. MAP kinases, also known as extracellular signal-regulated kinases (ERKs), act as an integration point for multiple biochemical signals. This protein phosphorylates and activates p38 MAP kinase in response to inflammatory cytokines or environmental stress. As an essential component of p38 MAP kinase mediated signal transduction pathway, this gene is involved in many cellular processes such as stress-induced cell cycle arrest, transcription activation and apoptosis (Entrez Gene: MAP2K6 mitogen-activated protein kinase kinase 6".).

An illustrative amino acid sequence (SEQ ID NO: 3) of human Map2k6 is NP_002749.2:

```
MSQSKGKKRNPGLKIPKEAFEQPQTSSKACISIGNQNFEVKADDLEP
IMELGRGAYGVVEKMRHVPSGQIMAVKRIRATVNSQEQKRLLMDLDI
SMRTVDCPFTVTFYGALFREGDVWICMELMDTSLDKFYKQVIDKGQT
IPEDILGKIAVSIVKALEHLHSKLSVIHRDVKPSNVLINALGQVKMC
DFGISGYLVDSVAKTIDAGCKPYMAPERINPELNQKGYSVKSDIWSL
GITMIELAILRFPYDSWGTPFQQLKQVVEEPSPQLPADKFSAEFVDF
TSQCLKKNSKERPTYPELMQHPFFTLHESKGTDVASFVKLILGD
```

The corresponding nucleic acid sequence (SEQ ID NO: 4) encoding human Map2k6 is NM_002758.3:

```
agttccaagtttggagcttttagctgccagccctggcccatcatgta
gctgcagcacagccttcctaacgttgcaactgggggaaaaatcact
ttccagtctgttttgcaaggtgtgcatttccatcttgattccctgaa
agtccatctgctgcatcggtcaagagaaactccacttgcatgaagat
tgcacgcctgcagcttgcatctttgttgcaaaactagctacagaaga
gaagcaaggcaaagtcttttgtgctccctcccccatcaaaggaaag
gggaaaatgtctcagtcgaaaggcaagaagcgaaaccctggccttaa
aattccaaaagaagcatttgaacaacctcagaccagttccacaccac
ctcgagatttagactccaaggcttgcatttctattggaaatcagaac
tttgaggtgaaggcagatgacctggagcctataatggaactgggacg
aggtgcgtacggggtggtggagaagatgcggcacgtgcccagcgggc
agatcatggcagtgaagcggatccgagccacagtaaatagccaggaa
cagaaacggctactgatggatttggatatttccatgaggacggtgga
ctgtccattcactgtcaccttttatggcgcactgtttcgggagggtg
atgtgtggatctgcatggagctcatggatacatcactagataaattc
tacaaacaagttattgataaaggccagacaattccagaggacatctt
agggaaaatagcagtttctattgtaaaagcattagaacatttacata
gtaagctgtctgtcattcacagagacgtcaagccttctaatgtactc
atcaatgctctcggtcaagtgaagatgtgcgattttggaatcagtgg
ctacttggtggactctgttgctaaaacaattgatgcaggttgcaaac
catacatggcccctgaaagaataaacccagagctcaaccagaaggga
tacagtgtgaagtctgacatttggagtctgggcatcacgatgattga
gttggccatccttcgatttccctatgattcatggggaactccatttc
agcagctcaaacaggtggtagaggagccatcgccacaactcccagca
gacaagttctctgcagagtttgttgactttacctcacagtgcttaaa
gaagaattccaaagaacggcctacatacccagagctaatgcaacatc
cattttcaccctacatgaatccaaaggaacagatgtggcatctttt
gtaaaactgattcttggagactaaaaagcagtggacttaatcggttg
accctactgtggattggtgggtttcggggtgaagcaagttcactaca
gcatcaatagaaagtcatctttgagataatttaaccctgcctctcag
agggttttctctcccaattttcttttactcccccctcttaagggggc
cttggaatctatagtatagaatgaactgtctagatggatgaattatg
ataaaggcttaggacttcaaaaggtgattaaatatttaatgatgtgt
catatgagtcctcaagcttctcagacttctcttattctttacaaaat
gaatgcattggccctgacaaaaaggtgctacggtagtgatgaaatta
taagtagatttgtagtttgtcccatttattattttaatatttatgtt
taagtgcttggttgaaaagattccattttatacaagaagggagattc
aaaaaaaaaatataaggttgggttagcaatatttataggcttttat
tttttaagttcaattgtgtctgtggtccagaagaaatttatttaatat
gcatctttgagaatattataaaaatatcaaaaaggaaaaaaaaaa
```

Another illustrative amino acid sequence (SEQ ID NO: 5) of human Map2k6 is NP_001317379.1:

```
MELGRGGAYGVVEKMRHVPSGQIMAVKRIRATVNSQEQKRLLMDLDIS
MRTVDCPFTVTFYGALFREGDVWICMELMDTSLDKFYKQVIDKGQTIP
EDILGKIAVSIVKALEHLHSKLSVIHRDVKPSNVLINALGQVKMCDFG
ISGYLVDSVAKTIDAGCKPYMAPERINPELNQKGYSVKSDIWSLGITM
IELAILRFPYDSWGTPFQQLKQVVEEPSPQLPADKFSAEFVDFTSQCL
KKNSKERPTYPELMQHPFFTLHESKGTDVASFVKLILGD
```

The corresponding nucleic acid sequence (SEQ ID NO: 6) encoding human Map2k6 is NM_001330450:

```
ttgctgcaatccgaacttgaggaggggtggagtctgttcagttctgtttctccttgccgaagtgtggtctttggagctaagtgaaga
atgacttctgttaggttttcctctgctggtcttccttgcagcctcgaaaacctcaccagagtcgcctctgctggtctcttactgtgctgctctg
tcagagatgggcaagtaagcgaactgcagagtgttgctgtgtgtgcttgtgatttgtattttatttgatgtaaacgtgaaggcagagtattt
ctaacactgtaattcaactaggttttgtgtctcctggatctattttttttcttgttgttctgaggagctgatatacttggaaatattaggtttaaga
tatgcagatgtccaacttatatacatagtcaagggtttagagtctggagacaggaggctggcaatttcaactaggaggcagtaaattcag
ggcaagaagcgaaaccctggccttaaaattccaaaagaagcatttgaacaacctcagaccagttccacaccacctcgagatttagact
ccaaggcttgcatttctattggaaatcagaactttgaggtgaaggcagatgacctggagcctataatggaactgggacgaggtgcgtac
ggggtggtggagaagatgcggcacgtgcccagcgggcagatcatggcagtgaagcggatccgagccacagtaaatagccaggaa
cagaaacggctactgatggatttggatatttccatgaggacggtggactgtccattcactgtcacctttatggcgcactgtttcgggagg
gtgatgtgtggatctgcatggagctcatggatacatcactagataaattctacaaacaagttattgataaaggccagacaattccagagg
acatcttagggaaaatagcagtttctattgtaaaagcattagaacatttacatagtaagctgtctgtcattcacagagacgtcaagccttcta
atgtactcatcaatgctctcggtcaagtgaagatgtgcgattttggaatcagtggctacttggtggactctgttgctaaaacaattgatgca
ggttgcaaaccatacatggcccctgaaagaataaacccagagctcaaccagaagggatacagtgtgaagtctgacatttggagtctgg
gcatcacgatgattgagttggccatccttcgatttccctatgattcatggggaactccatttcagcagctcaaacaggtggtagaggagc
catcgccacaactcccagcagacaagttctctgcagagtttgttgactttacctcacagtgcttaaagaagaattccaaagaacggccta
catacccagagctaatgcaacatccattttcaccctacatgaatccaaaggaacagatgtggcatcttttgtaaaactgattcttggagac
taaaaagcagtggacttaatcggttgaccctactgtggattggtgggtttcggggtgaagcaagttcactacagcatcaatagaaagtca
tctttgagataatttaaccctgcctctcagagggttttctctcccaattttcttttactccccctcttaagggggccttggaatctatagtatag
aatgaactgtctagatggatgaattatgataaaggcttaggacttcaaaaggtgattaaatatttaatgatgtgtcatatgagtcctcaagct
tctcagacttctcttattcttttacaaaatgaatgcattggccctgacaaaaaggtgctacggtagtgatgaaattataagtagatttgtagttt
gtcccatttattattttaatatttatgtttaagtgcttggttgaaaagattccattttatacaagaagggagattcaaaaaaaaatataaggttg
ggttagcaatatttatagggcttttattttttaagttcaattgtgtctgtggtccagaagaaatttattaatatgcatctttgagaatattataaaa
atatcaaaaggagctcttcttgtgaaatgtctgttccagctgttgtgactgctgccatttttgcaaacatctgcccaatcctgggtgatcac
cacatcttttaggggaagtgacaagatgctctggtcatactcttttcccaactttggaaaacataaaaatcactcatataacagctcaaag
agtaaaacatttggttcttctgacacttgtggtatagtattagtggaaagtgatttgtaatatgattttatatccacctacctattcatctacctgt
gtgtatgtgtgtttgtgtgtctatttggcaattcacaagtcctgccaagtggtttctatgagcatctctgtttggtaaggaggacaattgtc
agttttgagggggacatgtgttaaatcacagaaaaaatggtgccttcttctgcgtttgtccctcctgccatgtgtaagttgtaaggattgc
ctttgtagttaatgtactctttggctttgtttgtttgttttcttcttcagtgaagcagccttactattcatagaagggctagaataggagaaatg
aaaggtagtgagtaattctttgataagatgaggaaataatgggaaaggttgaattaattcctgggcatggactaccagatgaccacaagt
tgcgttgaggccgcatctttcttcagcagcgtgcaatagctggctcctctataggagatgagcttcattgggagttcctagcaagttgact
aaacagcaaaagttcttctcgtgggtaaatatcccacaggttctatgatttgtagctctaggtttcttgatgatcaaggagtgaagtaatt
gacagggaaaatatagacctatgataaataaccaggaagcattgcttttggacaaggaaggacagagggttttgattttaaaaagaaga
aaaaaaacctatttttcttcttggcctcaagttcaatatggagaggattgcttccctgaatcctctcttccttcccctttagattttgaagt
gcaatcatatgttttctctgtttgcattttttcctccttgttcttgacaaggaggagttgctcctgcccagaatgagcgtgacacttccgaaca
cttcttcatattcagttccaagatatatctgcttgattaaacatgagcttcctctgctctgaagctacctctgtcctcatttttattctagccagaa
```

-continued

```
aaggagtatcaccctagtgattatggctgttcactttcccatctatcttcctaaatctggaagttcttctcttggagatcaagagaaaattac aattgtattccttactttattcacccacctatgaaaacaggaagcaataggaaaaaaaatccggttactccattttagcttttggtgaacgat gtagagcaaattgtctctctggtctaggtccgattactcttacctgttttttccactttgagacattctaaacagaatgtgtaacttctcatatgta tgcctctcccatctgtgaacctaggccaaagttgcaaaaacaatcatattaatagtagagtagagaaaaagttagtctatggttctcaacc ctcgtgtacattggaaccatctgggagctgtgaacactgtcgctgccaatgttccagccaccagagatttggatttaactggtgggcct aggaattggtgttttttgttttgttttgtttttttacacaccttcatgtgattctgatgtgaagctgggttcagaacacttatctagtaccttctaaa gagaactgacttaaatttacttcttttgaacatttgcagggagtaacatgccattgcagaaagtaacaaaaacaggtcctatttctttccct gtcctcatcagtggaaatctctttgtcactctgagagaaggcatgtacctgggatactgataggaagtgtagaacacctttttccccagag aagcaatattttgcactgttattaaatatcttacacggtaaagtcaaaagaatgacctgatagcctcacaagactaaattttagagcatggtt ttgttttggaaaactgtgttgtaagtgccaatcaaccaacttttgaaaaaatcaagatacctaaactatatataaatggggagtattctgtac atatagacttatatataaagacatctgtgttcacggatgaccctcaaaatagttaatgccccaccagcatagaccatctgaatatcagccct gtctacacctatcaatgtattacaaaatcagtatagctctacaaaagagatcatgcttatttccccagatgtatttgattttgtatcatataattg tccatgttataattttttgaaaatgtttattaaaatagccatcttttttgatattattggtttaagaggtgtgccaaaaaaagtaatatgcataacttt taagactattaccctatgtttgtacgtatgagtgaatattgccaccagagtagccatcttgagagactacatatttatattcataatgctatta aattattttgccactcctctttcagaaaaggctttagaatccactccctcctctgagatgtgtgtcatcatttgagaattcttacttaggttttgt tgttgtttgttttgcttttttacaaaaatccttagcagatgtttccctctttgatttacctgccttgtttatcagattttgcacaaagttgtgtttgaca atttctagaagttaaatcttccctcagagctggagttttagcatcattgactctttgtaaaacgccatgtcatgggctctgaagataaatttcaa atgaagatttccacaccccgccccaccacccctgcccaaagtgcatgattattttaaccagagtcattcttccaccagaataagtgtaa tctcccaaaatgactactttgaaggagatagaaccccccataaaggtatatgtttgttgataaaatatcaggtcatcacggattttgcaagtg aaagtcacctatcttctatgattgaaggtcctgatgtgggggaataatctattttttctaaagactgtgtttggtcacactgatttaatcagaac aaatgggttaaataagcagcttttatcacagttaagccatctgaaatggaaacgagtatgtatgggcatggcttgaaattgtttgtattttac agttcttgtatatccttcaagcctaacaaaaaattgtatgtgccagagattcctaaactttctgtgttcagggtgccattagttgtcttggtact tttttcatggtgccccaggtcaaaatatatacttaatagttcagtgttttaagtaattaggtcccaacagcttaataatagcagtttgcacagt gtcctgcatatatcactatatttcccttaaaaatttccagcattggctgagcatggtgactcacgcctgtaatcccagcactttgggaggct gaggcaggtggatcacctcaggtcaggaatttgagaccagcctgactaacatgatgaaacccgtctctactaaaaatacaaaattagc tgggcatggtggcacatgcctgtaatcccagctactcaggaggctgaggcaggagaattgcttgaacccgggaggcggaggttgca gtgagccgacatcgtgtcagtgcactccagcctgggcaacaagagcaaaacttcatctcaaaaaaaaaaaaaaaaatgtacaacatc ttgcttagcctgtgtgtgttctgtggtaccttggaatagctcagtacataatttggggaccacagatatctattatgccaatgtttgcactgtct gctgttggtgaccctcaaaatgaaattcttggccactcaactctecacattatttcactctttgttttgttattattagtattcttcttgcttgccatt ggctaattcatttttttaactgcaaccctactcttctttgctgttcatcagccctgcaatgccgtagtgtcttagtctagaaaaatgcaatactca aaagccccagcattggaggaggctggtgctaagatggacagggttcctgatttctctcattgaacttgatttagtgtcttgggaattataat ctcaaaggaggcagagaggggttaatgttgcataatttatcactaaaatgtctttgttgaccaaggggctttattaattatgctcagagaaa caattctgtttctcttaaaagtgtctaacaaaacacttttttctttggcctgaaaggacaatggatacctagttcctaatttcctacccaaatgc tgttttggctgtgttactccctctgccctcgaagctaagatttatatatttacaaaatttattggagctggtagtcagatctagtaaaatggatt aaatgtcaattgtgctggattttgccttaacatctatctatgacttgaagagggatttgttggctcaaaggatcttctgcttttaatgaattag caagtgaaaaggtatttgaataaatgtcaacttcataggacttttttttttttaacttttcaaatggaaggtgcagttttcaattaggcctctga aaatttacatagtcagatgaaaaatgccagagtaaaatctaggaagaaggagctaccagacccgatagaatagaaagaaagctatttt attctcggaggtctatgttcctcttgtgtttgagtgcctctagcactgttaaatgtgctgacagctaaagatgctctttgggtttttttttttggctt taatttgggtactatggattcttttgggaatttgttgaaagctaggacctttccccaggaaaatttacattgtatatgaagcacataatttttgc aaactttttttggttgttgttgggagggggttgcagtttatatactccacggggttagtagctctgttctgtagaatattgactgtgacatccta
```

-continued

```
gaccacggttggcaaacttttctgtataggaccagatagtaaatattttggctttgtgtgttataccatctctgtcacagttactcagctctg
ctgttgtatcatgaaagcatctatacgcaatacacaaatgaatgagcctggtggctgtgttccaataaaactttatttacaaaccaagcaat
gggccaaatttggcccacaggccatggtttgccaacaccagtcttagagcattaaatataaaactctgattaactagatatgtagagttctt
ccattttagtgactattgagctcagctgctgttgaggcagattaggaagatggacataggaaactggattcagaaaggatgaggactgtt
tagtcccatgaaagttgcttgttaatgtcctcaggtaagtatgaattgttctggaagctgatagaacaattttcttcagatcaaactgaagta
cttacttttccattctatgcaatcaccaacataatttacttcaatttggaaataaatgtcacagttctcttagttgttaactgtatccttggctta
ggttatttgcatttctttctttcttctgtagtgtggtttatacacaaggagaatcacgaacccagacactagtcaatctctctattccctgactt
gtactgagattggggaatttgggaggtcagacttacctcaaacgtagaagaaggcagatagagttcttaaccttttcaacttagccacct
caattatttgttcacattttaaggaagtaggaaagagtagtttgaagtcacaaaatttgttctcaggtgttcttaaagctccctgttctcactgc
gacagaagactcaggcctactcattttgtgctgtcccacaaaagtgagaggagtacttctctttttttaaatcatcagtaaatttcaattttaa
ggggcctatgcaaaatgcctcctttctgatgtgattttcttgggttgctggccctagttgaatttatgggccctgaagcctctagtggaaatc
ttgtcttccctatagaacgagaacagctatgtaatttgcttcaccttctgttaggacttgcaccctctttgccatacagaatgctataaaaag
gacagtctgccagtgaccgaagctttctcattttttttcttccagaacaatagcacacatcttggttaaagctatagtctccttattattcaga
aatattcttttcctgctgcaccattaggcaaacatacattatgcttagaatgatacttggaaactccttaacagggcatattgaagtatttgat
ccagcaacttacctaaaagaatgtttgctcttcacctagggaaataaaacctgaatttcagagccttcaaaatgaaattatccttccaggg
gaagcacattgccaccaaatacatcactcactacctgttcctggtgactacatagaagatgtgttatttttctgaggtttagaaagtcactgt
ttacagctatgcaaatattgtactattacagattttctaatgaagtagtttgaaatcaaggctttagtggaaggtaatcttttcagttctgacc
cagatttcttttcaagcaaaactcctctgaaagcctctttgctatagaggtgatgaaggcacttgctagcctaagcagaaacataaagta
aaaaattttgtagtagggaattttgttggtaagaaatcagtatcatcttgtaacacaaacacgtgttaatagaacttaaaaatactcagccta
attccttgggactttcagtatcttgacatcacttgtattatcatttgaacttggacattgagccctttattttgggagtttacagttaaattttgga
agaattgtgttgtatttctttcttagatgttgtcagtatgaacagaattttttgtgaacagttaatcttgatgtgctccatagctttctccagttta
cacttttgcatttctgagattcagggtcttttcaaggaaggaggctaatgtttaaggcctggaggctgaattcagggagcgtattggcaa
gtttaggcacttacttgtgtcttaatgtgggaaacagaactttctaagtaatctctggagtttgtagcttagaccaggccttcaaaagtctttt
ctgttttcctttgctacaatttgcttgttatttctctgccggtcacagatgacctggactgactgaatgcttttgtggtaaggaactgatctggc
cattttcatataacaaaaatcaaagtcaacaattttgtatcaggctgcctaaatgaaccctattgtttccagttcttaaaaatttaagggctatc
taagaaaagtttaagcaaaaccctcattccaaacatgcgaccttataataagaacttcctttaaagatgagcagcaaggttgggtatctga
tttcactaagtaatattctattgtggtcagaaatgggtaatttgcatcatttggtcactatcaatatttgtgttggagtctgcaagatatttcaac
aaagtaagccaaaccactatcttaggggattgttgctggactttggaatataaggctgaacagtgatgtgaagtcatgtttgggggctgg
aagaagtgataaatgcaaaggttggtgctaaattaggaacccctttgaaggagcaagctgattaaaaaaaaaagctggcagacaagtat
atcttttaattatttgcagtgttgctatattatagagatgatttcctatgggaaaacccatcaaaaagccaaacctttattgttatttttccttaaa
aatactgagctataagaagattcagagagtggcattaatttgggcatcagaacattttcttttgtatccctagtgttattgatttgaaagagtt
accttttcagacagatggctgaacaaaagtaaatgattaacgggaaatttgatggttgagaaaaaggaacgatatgcctaaagcattttg
agaatataccccctcatccatcagccacctctgggtaaagaaacacaaataccaaagcctgagctccttaaccttttgttccagagggca
gacattttaagaaaggtgaatgttagagaaggttacctgatgagcaagcttctttcccataattcagagaactgtgaatgtacttagaaat
acactacaggtcttcaccagatgaactagattttataattttaaaatataatactgaaagctagtttgaagtttcagaagccatgaattatgg
ggaaggagtagttttttatttttattttattttctgatctcaagttgtttgtcctgttgtatgttcaatacttggggagataagagcgaggtacagc
tgtggttttcagaccatattcagtggtgcccctgagggtctcttgtgaacagaagggaaaagagtgtgatgaaggtgaactctgcctat
ctgaacctctgtcaacctccagtcagaatatctggctctagtattgttccttttaactggaagtctctgtggccattaaaaacttgggaacgt
tggattaaatgaccactttaggactttaaacagtctcaaatatgggaaattttatagccaaccacggctgtgagtccctggcttttgccgta
ctgagtatgctcacagagataggagataggtggccagaagacagggtcatttaattttaattgagcataaatcattttgaaagaaaat
gcaaggaattgttgtatgacagccatgcattatagatccttacatgcgacattttcctaaagtggttgagaatgacctgatctttgttcaccg
```

-continued

```
tctcagtgacaaggcgtggagtgactgggctcttcatatgcagtggaattttttgcatctctaggtttgcagaggcaggagttaccgttttttg ttcattgacctatcagaaaaaagcaaatcctttggacaatgttgacacagacaggggtacggtctgagactcaagctaacagagctacc ccttgctgccttttgcaaaggtgttgtaggtggagaagggtaatggaaacctggtacagcctttagaagttggaagctatggtggtgtatc tgtcatgaactgcacacaagggaatgcttaaacaccagctgagtcatatcaggtgccttgtacacacacataaagagtctggtgaattct gacagtgttctgtttgccactagagcaaatttaatagctggggtttcacagcaactgttttagaaaactatatgtgccaaaaatttacattgg gcagcagtttatagtgttcttggccaatctgcataaaagccacttgaggaggtttgattaagaaaattgtgtttatctcctgtattacctctgt gtttgatttattctttagtctcaaatttattttctgagtggactgattttctatatgaactgaaatgatgtttaatagaataataggtattttagag gaaaagtattttttttgtgtaatttgcttacacaactaggacatacttcctatgatactgaatcatcaaattgagtcatttaaagctgaaagaggt gttaggaatgtagtttcacattatttaaatacatgaacagttttctatatattttgtgaaaatcttgatgagacactagaatttctttatggaattg aactttacaagaattttaataaaagaggtggatttcttcagctttctttgtgcttcagtttcatagctgaaaatgctgcttccgtttattaatatgg actttgtaaggaaacacaacaacacgttttcttaccttctgtaaattttgtgatagacacatgttatttgtatatatgattgattgtttgcctgttg caccctaaagttattttcaaaccatgtttattgcaaagagagcctttgggcaagtggaaaatgccctgatgctagaatgaggtagttccat aagctagttaggagcttgctacctcttcttggtacctgaaatattctgaaaggatatcggagaggtcctatgcaccoctgtctttcaaaacc cacctccagcacttcaaagtagtgtctctggagagtttaaaataaaagaatgaatgctattcagtggattccctcattgaggctcccatcttt cctgccaggtgcagcttttctggttggaatcatctcttctttacggattgccgcattgtctctttgtgaatgaggcaggctgaactgtagag catgaaactcattagaagtttataaagtaaagacctgtaaagcatgtgggtggaatgtttccatgctcttgaggtgaatattaaatttaaatt ctggcctttgggaactctttgcttgtgagctgaagaaggaaagaaggagttgggggtgtatatctaactgtgttttctatatggaaatatat gagcatcaagtgataacttcaataaggcctcaggattgtatttaaaatacctgttttgtgggacagcatgcctttgttttctttgcctgttggct ttggtggctccaaacatttcattttaggctagctttcctgtcacccaggttgtgtgcatttttttttcatttgaactattgtttatcattattaatga tgttatctccaaatcccaaagccaaggaaatagccagtatgcaggacttgcagtagatataagcattggtgttaacataggttaagttttgt tagtgttcccagaaatatactgaattgagggataatgtagctttaaagaaattatgtttcttttttaacatttggagaagccacctgtcctgggt ccctattcttgagaaattcatcttttcatgcaaataacattgatgggggacaagactggatgattgacttctatcagtcagtagacaaggaa gtataataattgccaaaggtgagggtaattttgccttacaagtatgtaggtcattctgtggtgggatttcccatcacatctagtaaaaaacaa ccttttcatttccctcctttctaatccaagatcatattttaaaaagtaggtttctgatgtgccatgaaatatttctgtgaatctgtgttttttgacca aggaaacagctgagatattaaaccatgtggttgttccacggttcatctggctaccgttctgggtcccctctgaccacctcaaaaagaaaa tgaaattgggagattaaatcaagcttgacctcctcttttaatgaggaactttcacgttgacttcctatctcaggatattcttcagtttcatactg ctgaggagaaaggaacaagctgcagacactgtaactggtctccagatgtgtgtatatgcgtgtaaaacttcacaccgtgtgtgttgtgtt caatgttgtgtcaatctacaaactgactcaaacaacagtttaacgatagagaagacagtgataatggcaaaaaaaacacccaaccacct ttttccgtcaaagtgcttgctatggctttcatagctgggacaagtaacattaagtattcaggagcaaagtgttcttgaaagaaaatggtgtgt tgatctcataagaaaatgtacaaccaataaaagacatttaaaaagaaaaaaaaaaaaaaaa
```

Known MAP2K6 inhibitors include those recited in Table 3.

TABLE 3

MAP2K6 Inhibitors

| Compound | Action | Mechanism of Action |
|---|---|---|
| WX-554 | inhibitor | MEK inhibitor |

TABLE 4 dbSNP MAP2K6 Variants

| SNP ID | Chr 17 pos | Sequence Context | Type |
|---|---|---|---|
| rs707247 | 69,430,471(-) | TTCTT(A/T)CAGGC (SEQ ID NO: 14) | intron-variant |
| rs707248 | 69,416,490(-) | CTAAA(G/T)GCCAT (SEQ ID NO: 15) | intron-variant |
| rs731606 | 69,430,375(-) | TTCCA(A/T)TTGGC (SEQ ID NO: 16) | intron-variant |
| rs732322 | 69,422,847(-) | tggcc(C/T)aggag (SEQ ID NO: 17) | intron-variant |
| rs739559 | 69,494,089(-) | CCCTT(A/G)TTATT (SEQ ID NO: 18) | intron-variant |

MAP3K4

Mitogen-activated protein kinase kinase kinase 4 is an enzyme that in humans is encoded by the MAP3K4 gene (Takekawa M, et al. (October 1997). *EMBO J.* 16 (16): 4973-82; Entrez Gene: MAP3K4 mitogen-activated protein kinase kinase kinase 4").

The central core of each mitogen-activated protein kinase (MAPK) pathway is a conserved cascade of 3 protein kinases: an activated MAPK kinase kinase (MAPKKK) phosphorylates and activates a specific MAPK kinase (MAPKK), which then activates a specific MAPK. While the ERK MAPKs are activated by mitogenic stimulation, the CSBP2 (p38a) and JNK MAPKs are activated by environmental stresses such as osmotic shock, UV irradiation, wound stress, and inflammatory factors. This gene encodes a MAPKKK, the MEKK4 protein, also called MTK1. This protein contains a protein kinase catalytic domain at the C terminus. The N-terminal nonkinase domain may contain a regulatory domain. Expression of MEKK4 in mammalian cells activated the CSBP2 (p38a) and JNK MAPK pathways, but not the ERK pathway. In vitro kinase studies indicated that recombinant MEKK4 can specifically phosphorylate and activate PRKMK6 (MKK6) and SERK1 (MKK4), MAPKKs that activate CSBP2 (p38a) and JNK, respectively but cannot phosphorylate PRKMK1 (MKK1), an MAPKK that activates ERKs. MEKK4 is a major mediator of environmental stresses that activate the p38 MAPK pathway, and a minor mediator of the JNK pathway. Two alternatively spliced transcripts encoding distinct isoforms have been described (Entrez Gene: MAP3K4 mitogen-activated protein kinase kinase kinase 4").

An illustrative amino acid sequence (SEQ ID NO: 7) of human Map3k4 is NP_005913.2:

MREAAAALVPPPAFAVTPAAAMEEPPPPPPPPPPPEPETESEPECCL

AARQEGTLGDSACKSPESDLEDFSDETNTENLYGTSPPSTPRQMKRMS

TKHQRNNVGRPASRSNLKEKMNAPNQPPHKDTGKTVENVEEYSYKQEK

KIRAALRTTERDHKKNVQCSFMLDSVGGSLPKKSIPDVDLNKPYLSLG

CSNAKLPVSVPMPIARPARQTSRTDCPADRLKFFETLRLLLKLTSVSK

KKDREQRGQENTSGFWLNRSNELIWLELQAWHAGRTINDQDFFLYTAR

QAIPDIINEILTFKVDYGSFAFVRDRAGFNGTSVEGQCKATPGTKIVG

YSTHHEHLQRQRVSPEQVKRIMELLEYIEALYPSLQALQKDYEKYAAK

DFQDRVQALCLWLNITKDLNQKLRIMGTVLGIKNLSDIGWPVFEIPSP

RPSKGNEPEYEGDDTEGELKELESSTDESEEEQISDPRVPEIRQPIDN

SFDIQSRDCISKKLERLESEDDSLGWGAPDWSTEAGFSRHCLTSIYRP

FVDKALKQMGLRKLILRLHKLMDGSLQRARIALVKNDRPVEFSEFPDP

MWGSDYVQLSRTPPSSEEKCSAVSWEELKAMDLPSFEPAFLVLCRVLL

NVIHECLKLRLEQRPAGEPSLLSIKQLVRECKEVLKGGLLMKQYYQFM

LQEVLEDLEKPDCNIDAFEEDLHKMLMVYPDYMRSWIQMLQQLPQASH

SLKNLLEEEWNFTKEITHYIRGGEAQAGKLFCDIAGMLLKSTGSFLEF

GLQESCAEFWTSADDSSASDEIRRSVIEISRALKELFHEARERASKAL

GFAKMLRKDLEIAAEPRLSAPVRDLLDVLKSKQYVKVQIPGLENLQMF

VPDTLAEEKSIILQLLNAAAGKDCSKDSDDVLIDAYLLLTKHGDRARD

SEDSWGTWEAQPVKVVPQVETVDTLRSMQVDNLLLVVMQSAHLTIQRK

AFQQSIEGLMTLCQEQTSSQPVIAKALQQLKNDALELCNRISNAIDRV

DHMFTSEFDAEVDESESVTLQQYYREAMIQGYNFGFEYHKEVVRLMSG

EFRQKIGDKYISFARKWMNYVLTKCESGRGTRPRWATQGFDFLQAIEP

AFISALPEDDFLSLQALMNECIGHVIGKPHSPVTGLYLAIHRNSPRPM

KVPRCHSDPPNPHLIIPTPEGFSTRSMPSDARSHGSPAAAAAAAAAAV

AASRPSPSGGDSVLPKSISSAHDTRGSSVPENDRLASIAAELQFRSLS

RHSSPTEERDEPAYPRGDSSGSTRRSWELRTLISQSKDTASKLGPIEA

IQKSVRLFEEKRYREMRRKNIIGQVCDTPKSYDNVMHVGLRKVTFKWQ

RGNKIGEGQYGKVYTCISVDTGELMAMKEIRFQPNDHKTIKETADELK

IFEGIKHPNLVRYFGVELHREEMYIFMEYCDEGTLEEVSRLGLQEHVI

RLYSKQITIAINVLHEHGIVHRDIKGANIFLTSSGLIKLGDFGCSVKL

KNNAQTMPGEVNSTLGTAAYMAPEVITRAKGEGHGRAADIWSLGCVVI

EMVTGKRPWHEYEHNFQIMYKVGMGHKPPIPERLSPEGKDFLSHCLES

DPKMRWTASQLLDHSFVKVCTDEE

The corresponding nucleic acid sequence (SEQ ID NO: 8) NM_005922 encoding human Map3k4 is:

```
gatctgggaggcttgtccctcgccgcccaccgtagccccggcgctcggccggtcgccgtttccaagatggccgcggcgcgca cggctcctgcggcggggtagaggcggaggcggagtcgagtcactcccgcacttcgggggctccggtgccccgcgccaggctgcag
```

-continued

```
cttactgcccgccgcggccatgcggggctccgtgcacggatgagagaagccgctgccgcgctggtccctcctcccgcctttgccgtc acgcctgccgccgccatggaggagccgccgccaccgccgccgccaccaccgccaccggaacccgagaccgagtcagaac ccgagtgctgcttggcggcgaggcaagagggcacattgggagattcagcttgcaagagtcctgaatctgatctagaagacttctccga tgaaacaaatacagagaatctttatggtacctctcccccagcacacctcgacagatgaaacgcatgtcaaccaaacatcagaggaat aatgtggggaggccagccagtcggtctaatttgaaagaaaaaatgaatgcaccaaatcagcctccacataaagacactggaaaaaca gtggagaatgtggaagaatacagctataagcaggagaaaaagatccgagcagctcttagaacaacagagcgtgatcataaaaaaat gtacagtgctcattcatgttagactcagtgggtggatctttgccaaaaaatcaattccagatgtggatctcaataagccttacctcagcct tggctgtagcaatgctaagcttccagtatctgtgcccatgcctatagccagacctgcacgccagacttctaggactgactgtccagcag atcgtttaaagttttttgaaactttacgacttttgctaaagcttacctcagtctcaaagaaaaaagacagggagcaaagaggacaagaaaa tacgtctggtttctggcttaaccgatctaacgaactgatctggttagagctacaagcctggcatgcaggacggacaattaacgaccagg acttcttttatatacagcccgtcaagccatcccagatattattaatgaaatccttactttcaaagtcgactatgggagcttcgcctttgttaga gatagagctggttttaatggtacttcagtagaagggcagtgcaaagccactcctggaacaaagattgtaggttactcaacacatcatgag catctccaacgccagagggtctcatttgagcaggtaaaacgataatggagctgctagagtacatagaagcacttttatccatcattgca ggctcttcagaaggactatgaaaaatatgctgcaaaagacttccaggacagggtgcaggcactctgtttgtggttaaacatcacaaaag acttaaatcagaaattaaggattatgggcactgttttgggcatcaagaatttatcagacattggctggccagtgtttgaaatcccttcccctc gaccatccaaaggtaatgagccggagtatgagggtgatgacacagaaggagaattaaaggagttggaaagtagtacggatgagagt gaagaagaacaaatctctgatcctagggtaccggaaatcagacagcccatagataacagcttcgacatccagtcgcgggactgcatat ccaagaagcttgagaggctcgaatctgaggatgattctcttggctggggagcaccagactggagcacagaagcaggctttagtagac attgtctgacttctatttatagaccatttgtagacaaagcactgaagcagatgggttaagaaagttaattttaagacttcacaagctaatgg atggttccttgcaaagggcacgtatagcattggtaaagaacgatcgtccagtggagttttctgaatttccagatcccatgtggggttcaga ttatgtgcagttgtcaaggacaccaccttcatctgaggagaaatgcagtgctgtgtcgtgggaggagctgaaggccatggatttaccttc attcgaacctgccttcctagttctctgccgagtccttctgaatgtcatacatgagtgtctgaagttaagattggagcagagacctgctgga gaaccatctctcttgagtattaagcagctggtgagagagtgtaaggaggtcctgaagggcggcctgctgatgaagcagtactaccagtt catgctgcaggaggttctggaggacttggagaagcccgactgcaacattgacgcttttgaagaggatctacataaaatgcttatggtgta ttttgattacatgagaagctggatccaaatgctacagcaattacctcaagcatcgcatagtttaaaaaatctgttagaagaagaatggaatt tcaccaaagaaataactcattacatacggggaggagaagcacaggccgggaagcttttctgtgacattgcaggaatgctgctgaaatc tacaggaagttttttagaatttggcttacaggagagctgtgctgaattttggactagtgcggatgacagcagtgcttccgacgaaatcagg aggtctgttatagagatcagtcgagccctgaaggagctcttccatgaagccagagaaagggcttccaaagcacttggatttgctaaaat gttgagaaaggacctggaaatagcagcagaattcaggcttcagcccagttagagacctcctggatgttctgaaatcaaaacagtatg tcaaggtgcaaattcctgggttagaaaacttgcaaatgtttgttccagacactcttgctgaggagaagagtattatttttgcagttactcaatg cagctgcaggaaaggactgttcaaaagattcagatgacgtactcatcgatgcctatctgcttctgaccaagcacggtgatcgagcccgt gattcagaggacagctggggcacctgggaggcacagcctgtcaaagtcgtgcctcaggtggagactgttgacaccctgagaagcat gcaggtggataatcttttactagttgtcatgcagtctgcgcatctcacaattcagagaaaagctttccagcagtccattgagggacttatga ctctgtgccaggagcagacatccagtcagccggtcatcgccaaagctttgcagcagctgaagaatgatgcattggagctatgcaacag gataagcaatgccattgaccgcgtggaccacatgttcacatcagaatttgatgctgaggttgatgaatctgaatctgtcaccttgcaacag tactaccgagaagcaatgattcaggggtacaattttggatttgagtatcataaagaagttgttcgtttgatgtctggggagtttagacagaa gataggagacaaatatataagctttgcccggaagtggatgaattatgtcctgactaaatgtgagagtggtagaggtacaagacccaggt gggcgactcaaggatttgattttctacaagcaattgaacctgcctttatttcagctttaccagaagatgacttcttgagtttacaagccttgat gaatgaatgcattggccatgtcataggaaaaccacacagtcctgttacaggtttgtaccttgccattcatcggaacagcccccgtcctat gaaggtacctcgatgccatagtgaccctcctaacccacacctcattatccccactccagagggattcagcactcggagcatgccttccg acgcgcggagccatggcagccctgctgctgctgctgctgctgctgctgctgttgctgccagtcggcccagcccctctggtggtga
```

-continued ctctgtgctgcccaaatccatcagcagtgccatgataccaggggttccagcgttcctgaaaatgatcgattggcttccatagctgctga attgcagtttaggtccctgagtcgtcactcaagcccacggaggagcgagatgaaccagcatatccaagaggagattcaagtgggtc cacaagaagaagttgggaacttcggacactaatcagccagagtaaagatactgcttctaaactaggacccatagaagctatccagaag tcagtccgattgtttgaagaaaagaggtaccgagaaatgaggagaaagaatatcattggtcaagtttgtgatacgcctaagtcctatgat aatgttatgcacgttggcttgaggaaggtgaccttcaaatggcaaagaggaaacaaaattggagaaggccagtatgggaaggtgtac acctgcatcagcgtcgacaccggggagctgatggccatgaaagagattcgatttcaacctaatgaccataagactatcaaggaaactg cagacgaattgaaaatattcgaaggcatcaaacaccccaatctggttcggtattttggtgtggagctccatagaagaaatgtacatctt catggagtactgcgatgaggggactttagaagaggtgtcaaggctgggacttcaggaacatgtgattaggctgtattcaaagcagatc accattgcgatcaacgtcctccatgagcatggcatagtccaccgtgacattaaaggtgccaatatcttccttacctcatctggattaatcaa actgggagattttggatgttcagtaaagctcaaaaacaatgcccagaccatgcctggtgaagtgaacagcaccctggggacagcagc atacatggcacctgaagtcatcactcgtgccaaaggagagggccatgggcgtgcggccgacatctggagtctggggtgtgttgtcata gagatggtgactggcaagaggccttggcatgagtatgagcacaactttcaaattatgtataaagtggggatgggacataagccaccaa tccctgaaagattaagccctgaaggaaaggacttcctttctcactgccttgagagtgacccaaagatgagatggaccgccagccagct cctcgaccattcgtttgtcaaggtttgcacagatgaagaatgaagcctagtagaatatggacttggaaaattctcttaatcactactgtatgt aatatttacataaagactgtgctgagaagcagtataagcctttttaaccttccaagactgaagactgcacaggtgacaagcgtcacttctc ctgctgctcctgtttgtctgatgtggcaaaaggccctctggagggctggtggccacgaggttaaagaagctgcatgttaagtgccattac tactgtacacggaccatcgcctctgtctcctccgtgtctcgcgcgactgagaaccgtgacatcagcgtagtgttttgacctttctaggttca aaagaagttgtagtgttatcaggcgtcccataccttgtttttaatctcctgtttgttgagtgcactgactgtgaaacctttacctttttttgttgttg ttggcaagctgcaggtttgtaatgcaaaaggctgattactgaaatttaagaaaaaggttcttttttcaataaatggtttattttaggaaagctc aaaaaaaaaaaaaaaaaa

TABLE 5 dbSNP MAP3K4 Variants

| SNP ID | Chr 06 pos | Sequence Context | Type |
|---|---|---|---|
| rs1000277 | 161,105,793(−) | ACTAA(C/T)CAAAT (SEQ ID NO: 19) | intron-variant |
| rs1001756 | 161,105,475(+) | aaatg(A/G)cgagg (SEQ ID NO: 20) | intron-variant |
| rs1001808 | 161,057,414(+) | GAGCT(A/G)TAGAT (SEQ ID NO: 21) | intron-variant |
| rs1001809 | 161,057,478(+) | gtttc(C/G)aaacc (SEQ ID NO: 22) | intron-variant |
| rs10080366 | 161,019,422(+) | tcttt(C/T)tattt (SEQ ID NO: 23) | intron-variant |

Agents of the Disclosure

The disclosure provides agents to modulate the expression or activity of a MAP kinase pathway component, e.g., MMP17, MAP2K6 and/or MAP3K4, or a gene product thereof. In one embodiment, the agent is an inhibitor or antagonist of a MAP kinase pathway component, e.g., MMP17, MAP2K6 and/or MAP3K4, or a gene product thereof, that selectively blocks MAP kinase pathway signaling. In a particular embodiment, the agent is an inhibitor of MMP17, MAP2K6 and/or MAP3K4, or a gene product thereof. Non-limiting illustrative examples include small molecules (e.g., of Tables 1 and 3), antibodies, antisense and/or siRNA molecules directed to inhibit MMP17, MAP2K6 and/or MAP3K4, or a gene product thereof.

Agents useful in the methods of the disclosure can be nucleic acid molecules, e.g., antisense, ribozyme, or RNA interference technology, e.g., siRNA molecules corresponding to a portion of the nucleotide sequence encoding a component member of the MAP kinase pathway (e.g., a nucleic acid encoding Mmp17, Map2k6 and/or Map3k4).

Antisense polynucleotides may act by directly blocking translation by hybridizing to mRNA transcripts or degrading such transcripts of a gene. The antisense molecule may be recombinantly made using at least one functional portion of a gene in the antisense orientation as a region downstream of a promoter in an expression vector. Chemically modified bases or linkages may be used to stabilize the antisense polynucleotide by reducing degradation or increasing half-life in the body (e.g., methyl phosphonates, phosphorothioate, peptide nucleic acids). The sequence of the antisense molecule may be complementary to the translation initiation site (e.g., between −10 and +10 of the target's nucleotide sequence).

Ribozymes catalyze specific cleavage of an RNA transcript or genome. The mechanism of action involves sequence-specific hybridization to complementary cellular or viral RNA, followed by endonucleolytic cleavage. Inhibition may or may not be dependent on ribonuclease H activity. The ribozyme includes one or more sequences complementary to the target RNA as well as catalytic sequences responsible for RNA cleavage (e.g., hammerhead, hairpin, axehead motifs). For example, potential ribozyme cleavage sites within a subject RNA are initially identified by scanning the subject RNA for ribozyme cleavage sites which include the following trinucleotide sequences: GUA, GUU and GUC. Once identified, an oligonucleotide of between about 15 and about 20 ribonucleotides corresponding to the region of the subject RNA containing the cleavage site can be evaluated for predicted structural features, such as secondary structure, that can render candidate oligonucleotide sequences unsuitable. The suitability of candidate sequences can then be evaluated by their ability to hybridize and cleave target RNA. The ribozyme may be recombinantly produced or chemically synthesized.

siRNA refers to double-stranded RNA of at least 20-25 basepairs which mediates RNA interference (RNAi). Duplex siRNA corresponding to a target RNA may be formed by separate transcription of the strands, coupled transcription from a pair of promoters with opposing polarities, or annealing of a single RNA strand having an at least partially self-complementary sequence. Alternatively, duplexed oligoribonucleotides of at least about 21 to about 23 basepairs may be chemically synthesized (e.g., a duplex of 21 ribonucleotides with 3' overhangs of two ribonucleotides) with some substitutions by modified bases being tolerated. Mismatches in the center of the siRNA sequence, however, abolishes interference. The region targeted by RNA interference should be transcribed, preferably as a coding region of the gene. Interference appears to be dependent on cellular factors (e.g., ribonuclease III) that cleave target RNA at sites 21 to 23 bases apart; the position of the cleavage site appears to be defined by the 5' end of the guide siRNA rather than its 3' end. Priming by a small amount of siRNA may trigger interference after amplification by an RNA-dependent RNA polymerase.

CRISPR-Cas

In certain aspects inhibition of MAP kinase components can be achieved by administration of inhibitory nucleic acids (e.g., dsRNAs, siRNAs, antisense oligonucleotides, etc.). It is also contemplated that CRISPR-Cas (e.g., CRISPR-Cas9) methods can be used to excise and replace MAP kinase pathway component alleles identified to carry a deleterious mutation and/or variant that predisposes/contributes to MFS. Such variant alleles include the variant alleles identified in mice, for at least MMP17 and MAP2K6 herein, and further including similar human alleles of these genes, as well as of MAP3K4. Such methods can be performed upon the cells of a subject in vivo or ex vivo. Use of any combination of the above and/or other known MAP kinase component modulators is also contemplated.

The CRISPR-Cas system is known in the art. Non-limiting aspects of this system are described in U.S. Pat. No. 8,697,359, issued Apr. 15, 2014, the entire content of which is incorporated herein by reference.

Non-limiting examples of Cas proteins include Cas1, Cas1B, Cas2, Cas3, Cas4, Cas5, Cas6, Cas7, Cas8, Cas9 (also known as Csn1 and Csx12), Cas 10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of S. pyogenes Cas9 protein may be found in the SwissProt database under accession number Q99ZW2. In some embodiments, the unmodified CRISPR enzyme has DNA cleavage activity, such as Cas9. In some embodiments, the CRISPR enzyme is Cas9, and may be Cas9 from S. pyogenes or S. pneumoniae. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP (available at soap.genomics.org.cn; Ruiqiang Li, Yingrui Li, Karsten Kristiansen, Jun Wang; SOAP: short oligonucleotide alignment program, Bioinformatics, Volume 24, Issue 5, 1 Mar. 2008, Pages 713-714), and Maq (available at maq.sourceforge.net; Heng Li, Jue Ruan, and Richard Durbin. Genome Res. 2008. 18: 1851-1858). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

EGFR Inhibitors

In certain embodiments, a method for treating a subject having or at risk of developing Marfan Syndrome or a Marfan-associated condition comprises administering to the subject an effective amount of an agent that modulates the activity of MAP kinase pathway signaling and/or expression, function or activity of epidermal growth factor receptor (EGFR); thereby treating the subject. In certain embodiments, the agent that modulates the activity of MAP kinase pathway signaling is an inhibitor of the MAP kinase pathway. In certain embodiments, the agent that modulates the activity of MAP kinase pathway signaling is an inhibitor of MMP17, MAP2K6 or MAP3K4, or of a gene product thereof. In certain embodiments, the inhibitor of MMP17, MAP2K6 or MAP3K4, or of a gene product thereof, is an antisense agent or a double-stranded nucleic acid, optionally a siRNA or shRNA specific for MMP17, MAP2K6 or MAP3K4. In certain embodiments, the inhibitor of MMP17, MAP2K6 or MAP3K4, or of a gene product thereof, is specific for a nucleic acid molecule set forth as SEQ ID NO: 2, SEQ ID NO: 4, SEQ ID NO: 6 or SEQ ID NO: 8. In other embodiments, the agent that modulates the activity of MAP kinase pathway signaling comprise Batimastat, GI 254023X, GM 6001, TMI 1, WAY 170523, WX-554 or combinations thereof. Any combination of inhibitors can be used, for example, an siRNA and a compound, e.g. GI 254023X, and/or an antibody.

In certain embodiments, the agent that modulates expression, function or activity of epidermal growth factor receptor (EGFR) is an EGFR inhibitor comprising: an antibody, interfering RNAs microRNAs, shRNA, small molecule or combinations thereof.

In certain embodiments, the EGFR inhibitor comprises: gefitinib, erlotinib, lapatinib, Brigatinib (AP26113), Afatinib (BIBW2992), Neratinib (HKI-272), AZD3759, AZ5104, CL-387785 (EKI-785), Canertinib (CI-1033), Poziotinib (HM781-36B), Osimertinib (AZD-9291), PD168393, CNX-2006, Rociletinib (CO-1686, AVL-301), WZ4002, Pelitinib (EKB-569), AC480 (BMS-599626), TAK-285, CUDC-101, AEE788 (NVP-AEE788), CP-724714, Dacomitinib (PF299804, PF299), AG-490 (Tyrphostin B42), AST-1306, OSI-420, WHI-P154, WZ3146, WZ8040, AZD8931 (Sapitinib), PKI-166, PD158780, AG 1478, PD153035 HCl, Icotinib, Varlitinib, AZD-9291, AEE788 (NVP-AEE 788), AG-1478 (NSC 693255), AG-490, Anlotinib, ARRY-380, BIBX 1382, BMS-690514, cetuximab, panitumumab, zalutumumab, nimotuzumab, matuzumab or mAb 806. An anti-EGFR antibody comprises cetuximab, matuzumab, panitumumab, nimotuzumab or mAb 806 and a small molecule EGFR inhibitor comprises gefitinib, lapatinib, canertinib, erlotinib HCL, pelitinib, PKI-166, PD158780, or AG 1478. In certain embodiments, combinations of agents, e.g. antibody or small molecules, can be administered as part of the therapy. In other embodiments, an inhibitor of transforming growth factor β (TGFβ) is also administered.

In certain embodiments, a pharmaceutical composition comprises a therapeutically effective amount of at least one agent that modulates expression, function or activity of MMP17, MAP2K6, MAP3K4, epidermal growth factor receptor (EGFR), or combinations thereof.

An exemplary anti-EGFR antibody is cetuximab (ERBITUX™). Cetuximab is commercially available from ImClone Systems Incorporated. Other examples of anti-EGFR antibodies include matuzumab (EMD72000), panitumumab (VECTIBIX™; Amgen); nimotuzumab (THERACIM™) and mAb 806. An exemplary small molecule inhibitor of the EGFR signaling pathway is gefitinib (IRESSA™), which is commercially available from AstraZeneca and Teva. Other examples of small molecule inhibitors of the EGFR signaling pathway include erlotinib HCL (OSI-774; TARCEVA™, OSI Pharma); lapatinib (TYKERB™, GlaxoSmithKline); canertinib (canertinib dihydrochloride, Pfizer); pelitinib (Pfizer); PKI-166 (Novartis); PD158780; and AG 1478 (4-(3-Chloroanillino)-6,7-dimethoxyquinazoline).

The EGFR inhibitor may be an EGFR tyrosine kinase inhibitor, or may alternatively target the extracellular domain of the EGFR target. In certain embodiments, the EGFR inhibitor is a tyrosine kinase inhibitor such as Erlotinib, Gefitinib, or Lapatinib, or a molecule that targets the EGFR extracellular domain such as Cetuximab or Panitumumab.

In certain embodiments, the EGFR inhibitor is an anti-EGFR antibody, preferably a monoclonal antibody, such as Cetuximab or Panitumumab.

Cetuximab and Panitumumab are currently the clinically mostly used anti-EGFR monoclonal antibodies. However, further anti-EGFR monoclonal antibodies are in development, such as Nimotuzumab (TheraCIM-h-R3), Matuzumab (EMD 72000), Zalutumumab (HuMax-EGFr), Nimotuzumab and Sym 004. Similarly, Erlotinib, Gefitinib, Lapatinib and Regorafenib are currently the clinically mostly used tyrosine kinase EGFR inhibitors. However, further tyrosine kinase EGFR inhibitors are in development, such as Canertinib (CI-1033), Neratinib (HKI-272), Afatinib (BIBW2992), Dacomitinib (PF299804, PF-00299804), TAK-285, AST-1306, ARRY334543, AG-1478 (Tyrphostin AG-1478), AV-412, OSI-420 (DesmethylErlotinib), AZD8931, AEE788 (NVP-AEE788), Pelitinib (EKB-569), CUDC-101, AG 490, PD153035 HCL, XL647, Ruxolitinib, and BMS-599626 (AC480). The method according to the invention may also be used to predict response to these tyrosine kinase EGFR inhibitors or any other tyrosine kinase EGFR inhibitors that might be further developed, in particular if the patient is suffering from of lung cancer (in particular non-small cell lung cancer, NSCLC), pancreatic cancer, or head and neck cancer (in particular squamous cell carcinoma of the head and neck (SCCHN)).

TGFβ Inhibitors

Transforming growth factor beta (TGFβ) has emerged as a candidate mediator of disease pathology and a key therapeutic target in MFS (Massagu, J., et al. Cell 103, 295-309 (2000)). The TGFβ family of cytokines influences a diverse repertoire of cellular processes including cell proliferation, survival and synthetic activity. The TGFβ ligand isoforms bind to a cell surface complex of type 1 and 2 TGFβ receptor subunits (TI3RI and TI3RII respectively). These in turn phosphorylate the canonical cytoplasmic receptor-activated SMAD (R-SMADs) proteins, SMAD2 or SMAD3. TGFβ receptors can also initiate activation of noncanonical cascades including the mitogen activated protein kinases (MAPKs), extracellular signal-regulated kinase (ERK1/2), Jun N-terminal kinase (JNK1/2) and p38. There is a clear signature for increased TGFβ signaling in patients and mice with MFS, as evidenced by the accumulation of activated SMAD2/3, ERK1/2, and p38 (pSMAD2/3, pERK1/2, and pp38, respectively) in diseased tissues (Neptune, E. R. et al. Nature Genetics 33, 407-11 (2003); Ng, C. M. et al. J. Clin. Invest. 114, 1586-92 (2004); Cohn, R. D. et al. Nature Medicine 13, 204-10 (2007); Carta, L. et al. J. Biol. Chem. 27, 5630-6 (2009)). Furthermore, therapies that associate with increased TGFβ activation in MFS mice, such as calcium channel blockers, exacerbate aortic disease (Doyle, J. J. et al. eLife 4:e08648 (2015)), while those that attenuate TGFβ signaling and related pathways, such as TGFβ neutralizing antibody (NAb), the angiotensin-II (Ang-II) type 1 receptor blocker (ARB) losartan, or the inhibitor of ERK1/2 activation RDEA119, can suppress aortic disease in MFS mice (Habashi, J. P. et al. *Science* 312, 117-21 (2006); Holm, T. M. et al. *Science* 15, 358-61 (2011); Habashi, J. P. et al. *Science* 15, 361-5 (2011)).

The major classes of TGFβ inhibitors include ligand traps, antisense oligonucleotides (ASO), small molecule receptor kinase inhibitors and peptide aptamers. Ligand traps include anti-ligand neutralizing antibodies and soluble decoy receptor proteins that incorporate the ectodomains from either TGFβ receptor II (TI3RII) or TGFβ receptor III (TβRIII)/betaglycan protein. Neutralizing antibodies have been raised against individual ligands or may be designed to block all three human isomers TGFβ1, -2 and -3. ASO can also be used to reduce the bioavailability of active TGFβ ligands by blocking de novo synthesis of TGFβ. ASOs are single-stranded polynucleotide molecules, usually 13-25 nucleotides in length, that hybridize to complementary RNA, inhibiting mRNA function, and preventing protein synthesis through accelerated mRNA degradation by RNase H or steric blockade. Another therapeutic strategy is to block TGFβ receptor I (TβRI) activity through the use of small molecule receptor kinase inhibitors that act via ATP-competitive inhibition of the catalytic domain of the serine-threonine kinase of the TβRI (ALK5-Receptor). Lastly, targeting intracellular TGFβ signaling molecules, such as Smads, is possible with the use of peptide aptamers. Aptamers are small peptide, DNA or RNA molecules containing a target-binding and a scaffolding domain that stabilize and interfere with the function of the target.

Accordingly, in some embodiments, an inhibitor of TGFβ or TGFβ signaling is administered as part of a therapeutic regimen. TGFβ signaling controls proliferation, cellular differentiation, and other functions in a variety of cell types, and can play a role in cell cycle control, regulation of the immune system, and development in certain cell types. Inhibition of TGFβ signaling may include inhibition of any TGFβ signaling pathway and/or member of the TGFβ superfamily including ligands such as TGFβ1, TGFβ2, TGFβ3, inhibins, activin, anti-mullerian hormone, bone morphogenetic protein, decapentaplegic and Vg-1; receptors such as TGFβ type I receptor, TGFβ type II receptor, ALK1, ALK2, ALK3, ALK4, ALK5, ALK6, ALK7 and ALK8; and downstream effectors such as R-SMAD and other SMAD proteins (e.g., SMAD1, SMAD2, SMAD3, SMAD4, SMAD5).

In some embodiments, the activity of one or more TGFβ receptors is inhibited. In some embodiments, one or more TGFβ receptor-ligand interactions are inhibited. In some embodiments, a TGFβ type I receptor is inhibited. A TGFβ type I receptor may include one or more of ALK1, ALK2, ALK3, ALK4, ALK5, ALK6, ALK7 and ALK8. In some embodiments, the TGFβ receptor is ALK5.

A TGFβ inhibitor (e.g., a TGFβ signaling inhibitor) may be an ALK5 inhibitor, in some embodiments. An ALK5 inhibitor may bind to ALK5 or one or more ALK5 ligands or both. An ALK5 inhibitor may bind to ALK5 or one or more downstream SMAD proteins or both. An ALK5 inhibitor may disrupt one or more ALK5-ligand interactions or may disrupt one or more ALK5-SMAD interactions. In some embodiments, an ALK5 inhibitor blocks phosphorylation of SMAD2. ALK5 inhibitors may include one or more small molecule ALK5 inhibitors. In some embodiments, an ALK5 inhibitor is an ATP analog.

A TGFβ inhibitor of the present invention interacts with a TGFβ receptor, inhibits the signaling of the receptor, interacts with a TGFβ protein, and/or inhibits the transcription and/or translation of the gene encoding TGFβ-1, -2, and/or -3. The TGFβ inhibitor of the present invention inhibits TGFβ1, TGFβ2, and/or TGFβ3; in case an inhibitor inhibits all three TGFβ isotypes, the inhibitor is a pan-specific inhibitor. Examples of TGFβ inhibitors include: A) a small molecule inhibitor of TGFβ receptor type I kinase (ALK5; an inhibitor is an ALK5 inhibitor), B) a neutralizing anti-TGFβ-1, -2, -3 antibody or TGFβ binding fragments thereof, C) a neutralizing anti-TGFβ receptor type I, type II or type III antibody or TGFβ receptors binding fragments thereof, D) an antisense oligonucleotide specific for mRNA encoding TGFβ1, -2, and -3 isotypes or other components of TGFβ signaling assembly optionally comprising a modified nucleoside such as 2'-O, 4'-C-methylene linked bicyclic ribonucleotides, known as locked nucleic acids LNA (e.g., oxy-LNA, amino-LNA, thio-LNA), phosphorodiamidate morpholino oligomers (PMO), phosphorothioate (PS), 2'-O-methyl (2'-Ome), 2'-fluoro (2'-fluoro (2'-F), or 2'-methoxyethyl (2'-MOE) derivatives, E) an antisense RNA molecule specific for TGFβ2-mRNA like belagenpumatucel-L and/or TGFβ-mRNA or TGFβ-mRNA or other components of mRNA encoding TGFβ signaling assembly, F) a silencing RNA molecule (siRNA) specific for mRNA encoding TGFβ1, -2, and/or -3 isotypes or other components of TGFβ signaling assembly, G) a short hairpin RNA (shRNA) specific for mRNA encoding TGFβ1, -2, and/or -3 isotypes or other components of TGFβ signaling assembly, H) a miRNA molecule specific for mRNA encoding TGFβ1, -2, and/or -3 isotypes or other components of TGFβ signaling assembly, I) an aptamer and/or spiegelmer molecule specific for TGFβ1, -2, and/or -3 isotypes or other components of the TGFβ signaling assembly, and/or J) a ribozyme molecule specific for mRNA encoding TGFβ1, -2, and/or -3 isotypes or other components of the TGFβ signaling assembly.

ASOs are single-stranded polynucleotide molecules comprising 13-25 nucleotides, preferably 15-20 nucleotides, more preferred 15, 16, 17, 18, 19, 20, 21, 22 or 23 nucleotides, that hybridize to complementary RNA, inhibiting mRNA function, and preventing protein synthesis for example through accelerated mRNA degradation by RNase H or steric blockade.

In certain embodiments, a TGFβ inhibitor binding to TGFβ receptor type I, such as a non-peptide, small molecule inhibitor of ALK-5 kinase from dihydropyrolopyrazole derivatives (e.g., LY2157299, LY21109761, LY580276, LY550410, GW788388), pyrazole derivatives (e.g., LY364947, HTS-466284, SM305, SB525334, A-83-01), quinazoline derivatives (e.g., SD-208), or imidazole derivatives (e.g., SM16, SB431542, or SB505124). SD-208 for example is a small molecule inhibitor of type I kinase of TGFβ receptor with $IC_{50}=49$ nM, which inhibits TGFβ signal transduction in a dose-dependent fashion, as for example measured by p-SMAD2 western blot analysis.

A human pan-anti-TGFβ antibody binding to and neutralizing all three isotypes of TGFβ (e.g., TGFβ1, 2, 3) like GC-1008, a neutralizing high-affinity antibody or antigen-binding immunoglobulin single variable domain or polypeptide thereof, that neutralize mature human TGFβ1 (like CAT 192), or hTGFβ2 (like CAT 152), and neutralizing anti-TGFβ receptor type II antibody (like D10) or an antibody fragment thereof which binds and neutralizes human TGFβ receptor type II, a fusion protein comprising a TGFβ type II receptor fusion protein, a small molecule or peptide consisting of, for example, 11-50 amino acid residues blocking assembly of the TGFβ signaling complex extra- and intracellularly.

Pharmaceutical Compositions of the Invention

The agents described herein can be formulated into pharmaceutical compositions for the treatment of the diseases, disorders and conditions disclosed herein. The language "pharmaceutical composition" includes preparations suitable for administration to mammals, e.g., humans. When the compounds used in the methods of the present disclosure are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (13HT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present disclosure include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this disclosure.

Pharmaceutical compositions of this disclosure suitable for parenteral administration comprise one or more compounds of the disclosure in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue, The preparations of the present disclosure may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form, and/or the pharmaceutical compositions of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound that is the lowest dose effective to produce a therapeutic effect. Such an effective dose will generally depend upon the factors described above. Generally, intravenous and subcutaneous doses of the compounds of this disclosure for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a disease, disorder or condition set forth herein.

If desired, the effective daily dose of the active compound may be administered as two, three, four, five, six or more sub-doses administered separately at appropriate intervals throughout the day, optionally, in unit dosage forms.

While it is possible for a compound of the present disclosure to be administered alone, it is preferable to administer the compound as a pharmaceutical composition.

Certain aspects of the disclosure involve administration of nucleic acid agents. Nucleic acid agents can be effectively delivered to a subject as stabilized agents, with such stability often provided via lipid nanoparticle (LNP) encasement of active nucleic acid agents and/or modification of therapeutic nucleic acid agents with one or more stabilizing modifications, including, e.g., 2'-O-alkyl modifications (including 2'-O-methyl), 2'-F modifications, backbone modifications, locked nucleic acid (LNA) configurations, GalNAc modifications, cholesterol conjugates, etc. Such modifications are known in the art and can be readily employed by the skilled artisan for delivery of the nucleic acid agents of the instant disclosure.

Methods of Treatment

As used herein, the term "Marfan syndrome or associated diseases, disorders and conditions" is intended to mean Marfan syndrome or any one of the multitude of diseases disorders or conditions that is caused or associated with the biochemical events that cause Marfan syndrome, e.g., the aberrant expression or activity of a MAP kinase pathway component, e.g., MMP17, MAP2K6 and/or MAP3K4, or a gene product thereof. Exemplary conditions include aneurysm, an aortic aneurysm, valve disease, emphysema, myopathy, scoliosis, or eye disease. Exemplary eye diseases include cataracts, myopia, glaucoma, and retinal detachment. Moreover, Marfan syndrome or associated diseases, disorders and conditions include diseases and disorders that related to muscle growth, maintenance, or regeneration, e.g., muscular dystrophies such as Duchenne muscular dystrophy. Further, the disease or disorder can be a lung disease or disorder, e.g., emphysema, pneumothorax, and COPD.

The term "treated," "treating" or "treatment" includes the diminishment or alleviation of at least one symptom associated or caused by Marfan syndrome, or an associated disease, disorder or condition. For example, treatment can be diminishment of one or several symptoms of a disease or disorder or complete eradication of the disease or disorder, e.g., Marfan syndrome.

The term "subject" is intended to include organisms, e.g., prokaryotes and eukaryotes, which are capable of suffering from or afflicted with Marfan syndrome, or a disease, disorder or condition related thereto. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from a Marfan syndrome, or a disease, disorder or condition related thereto.

The agents and pharmaceutical compositions of the disclosure can be administered to a subject to treat or prevent diseases, disorders and conditions associated with aberrant expression or activity of a MAP kinase pathway component, e.g., MMP17, MAP2K6 and/or MAP3K4, or a gene product thereof. In one embodiment, the agents and pharmaceutical compositions are used to treat or prevent Marfan syndrome or diseases or disorders associated with Marfan syndrome.

In one embodiment, the agents or pharmaceutical compositions are administered in an effective amount using a dosing schedule determined by a medical provider to treat or prevent a disease or disorder set forth herein. The agents or pharmaceutical compositions can be administered in a variety of methods, as described herein and known to one of skill in the art.

In one aspect, the disclosure provides a method for preventing in a subject, a disease or condition associated with an aberrant expression or activity of a MAP kinase pathway component, e.g., MMP17, MAP2K6 and/or MAP3K4, or a gene product thereof, by administering to the subject an agent which modulates expression or activity of a MAP kinase pathway component, e.g., MMP17, MAP2K6 and/or MAP3K4, or a gene product thereof. Subjects at risk for a disease which is caused or contributed to by aberrant expression or activity of a MAP kinase pathway component, e.g., MMP17, MAP2K6 and/or MAP3K4, or a gene product thereof, can be identified by, for example, any or a combination of diagnostic or prognostic assays as described herein. Administration of a prophylactic agent can occur prior to the manifestation of symptoms characteristic of the aberrancy of expression or activity of a MAP kinase pathway component, e.g., MMP17, MAP2K6 and/or MAP3K4, or a gene product thereof, such that a disease or disorder is prevented or, alternatively, delayed in its progression.

Another aspect of the disclosure pertains to methods of modulating expression or activity of a MAP kinase pathway component, e.g., MMP17, MAP2K6 and/or MAP3K4, or a gene product thereof, for therapeutic purposes. Accordingly, in an exemplary embodiment, the modulatory method of the disclosure involves contacting a cell with an agent that modulates one or more of the activities of a component of a MAP kinase signaling pathway, e.g., MMP17, MAP2K6 and/or MAP3K4, or a gene product thereof. An agent that modulates expression or activity of a MAP kinase pathway component, e.g., MMP17, MAP2K6 and/or MAP3K4, or a gene product thereof can be an agent as described herein, such as a nucleic acid, a polypeptide, or a small molecule. In one embodiment, the agent inhibits one or more activities of a MAP kinase pathway component, e.g., MMP17, MAP2K6 and/or MAP3K4, or a gene product thereof, and/or inhibits one or more components of the MAP kinase pathway. Examples of such inhibitory agents include antisense MMP17, MAP2K6 and/or MAP3K4 nucleic acid molecules, anti-Mmp17, -Map2k6 and/or -Map3k4 antibodies, and small molecule inhibitors of Mmp17, Map2k6 and/or Map3k4. These modulatory methods can be performed in vitro (e.g., by culturing the cell with the agent) or, alternatively, in vivo (e.g., by administering the agent to a subject). As such, the present disclosure provides methods of treating an individual afflicted with a disease or disorder characterized by aberrant MAP kinase pathway signaling, e.g., Marfan syndrome or an associated disease or disorder. In one embodiment, the method involves administering an agent, or combination of agents that modulates MAP kinase pathway signaling.

The disclosure further provides kits comprising agents or pharmaceutical compositions of the disclosure and instructions for use. In one embodiment, the kits of the disclosure are for the treatment of diseases and disorders characterized by aberrant MAP kinase pathway signaling. In a related embodiment, the MAP kinase pathway signaling associated disease or disorder is Marfan syndrome or a disease or disorder related to Marfan syndrome.

EXAMPLES

It should be appreciated that the invention should not be construed to be limited to the examples that are now described; rather, the invention should be construed to include any and all applications provided herein and all equivalent variations within the skill of the ordinary artisan.

Example 1: Involvement of MAP Kinase Pathway Components Map3k4, Map2k6 and Mmp17 in Marfan Syndrome It has been shown that the C57BL/6 and Sv129 mouse backgrounds exhibit strain-specific modulatory effects on TGFβ deficiency phenotypes, and this may relate to their influence on downstream TGFβ signaling (Bourdeau, et al. American Journal Pathology 158, 2011; Warshamhabashiana et al. *Am J Resp Cell Mol Biol* 27, 705). With this in mind, it was examined whether the Sv129 background could exacerbate a MFS mouse model phenotype. MFS model mice from a pure C57BL/6J (hereafter termed BL6) background were backcrossed for greater than 10 generations onto a 129S6/SvEvTac (hereafter termed 129) background.

129 MFS mice exhibited a highly significant increase in aortic root size, post-natal aortic root growth and premature lethality from dissection, compared with BL6 MFS counterparts, in association with increased activation of both Smad2/3 and Erk1/2 cascades. All aortic parameters in 129 MFS mice were fully rescued by both losartan and RDEA119. 129/MFS mice also showed worse lung emphysema and spine kyphosis, with significant correlation between aortic root size and these phenotypes, indicating deleterious systemic genetic modification in 129 MFS mice. Wild type (WT) mice on the two background strains showed no difference in any parameter, indicating MFS disease-specific modification.

To map potential modifier loci, a large seven generational pedigree of intercrossed BL6 MFS and 129 MFS mice was generated. The resulting offspring were then classified as either BL6-like, 129-like or indeterminate, based on aortic size and shape at 6 months of age. Genome mapping of forty BL6-like and forty 129-like MFS mice revealed 2 QTLs on chromosomes 5 and 11 that strongly linked with severe aortic phenotype (LOD=4.76 and 4.78, respectively) and reached genome wide significance (p=0.008 for both), with evidence of epistasis between the loci (MfLOD=12.8; p=0.0006).

Causative genetic variation was searched for in these QTL regions using the mouse genome project, and one likely causal variant was identified in each locus, that was predicted to be both functionally deleterious and mechanistically linked to Mapk signaling. On chromosome 5, a missense point mutation in Mmp17 (rs29636438; p.X579W) was predicted to alter the C-terminal region, modify attachment of the GPI anchor, and affect its cell surface expression, causing greater activation of Mapk signaling in 129 MFS mice. On chromosome 11, a missense point mutation in Map2k6 (rs51129320; p.G76E) was predicted to cause greater activation of Mapk signaling in 129 MFS mice. Haploinsufficiency for Map2k6 and Mmp17 rescued aortic root growth in 129 MFS mice by approximately 50%, while knockout of these two genes reduced aortic root growth in 129 MFS mice to a rate indistinguishable from that of their BL6 MFS counterparts.

Genetic modifiers of disease progression in MFS patients were then investigated. Five exceptional families were identified to possess defined and typical FBN1 mutations, that showed discrete intrafamilial variation in the penetrance of vascular disease. Genome-wide linkage in these five families identified a major modifier locus for vascular disease in MFS, encompassing a 5.5 Mb linkage interval on chromosome 6 (LOD=4.0). While the protective haplotype varied between families, all patients with mild disease (20/20) shared a 3.9 Mb familial haplotype that was only observed in 2/18 severely affected family members (p<0.0001). Interestingly, this region includes MAP3K4, which lies directly upstream of MAP2K6 in the Mapk signaling cascade. Furthermore, haploinsufficiency for Map3k4 led to a full rescue of aortic root growth in MFS mice, to a rate indistinguishable from that of WT littermates.

Thus, a common pathway of genetic modification in MFS has herein been identified, which provides a rationale for exploration of therapies that target genes of this pathway/ these pathways, particularly including MMP17, MAP2K6 and MAP3K4. Given that a number of MFS-related conditions also appear to be driven by increased TGFβ signaling (Gallo et al. *J. Clin*. Investigation 124, 448; Doyle et al. *Nature Genetics* 44, 1249; Lindsay et al., *Nature Genetics* 44, 922), these pathways are likely also to hold broader clinical relevance. While losartan has been previously described as providing some degree of rescue of aortic root growth in patients with MFS (Lacro, et al., *New England Journal of Medicine* 371, 2061), there is still significant room for additional pharmacological interventions that can ameliorate the potentially devastating cardiovascular, skeletal and ocular consequences of the disease. Whilst surgical intervention exists for many complications, these often involve major procedures that have significant morbidity and/or mortality associated with them. Furthermore, they often require ongoing additional treatment (e.g., lifelong use of anticoagulation after aortic root replacement) which too possess risk for significant complications. The instant disclosure therefore seeks to provide a MFS therapy possessing the ability to prevent these deleterious outcomes from ever occurring, thereby negating the need for major surgical intervention.

Example 2: Materials and Methods

Mice:

All mice were cared for under strict compliance with the Animal Care and Use Committee of the Johns Hopkins University School of Medicine. The Fbn1$^{C1039G/+}$ line was initially maintained in a pure C57BL/6 background (backcrossed for greater than 9 generations), allowing for valid comparisons, prior to backcrosses with Sv29 mice, performed as described above. In order to further accommodate the potential for temporal- or background-specified variation, all comparisons were made between contemporary littermates when possible. Mice were sacrificed with an inhalation overdose of halothane (Sigma-Aldrich, St. Louis). Mice underwent immediate laparotomy, descending abdominal aortic transection, and PBS (pH 7.4) was infused through the right and left ventricles to flush out the blood. Mice that were analyzed for aortic histology had latex injected under low pressure into the left ventricular apex until it was visible in the descending abdominal aorta. Mice were fixed for 24 hours in 10% buffered formalin, after which the heart, aorta and lungs were removed and stored in 70% ethanol.

Echocardiography:

Nair hair removal cream was used on all mice the day prior to echocardiograms. All echocardiograms were performed on awake, unsedated mice using the Visualsonics Vevo 660 V1.3.6 imaging system and a 30 MHz transducer. Mice were imaged at baseline, and at six months, when also sacrificed. The aorta was imaged using a parasternal long axis view. Three separate measurements of the maximal internal dimension at the sinus of Valsalva and proximal ascending aorta were made from distinct captured images and averaged. All imaging and measurements were performed by a cardiologist who was blinded to genotype.

Histological and Morphometric Analysis:

Latex-infused ascending aortas were transected just above the level of the aortic valve, and 2-3 mm transverse sections were mounted in 4% agar prior to paraffin fixation. Five micrometer aortic sections underwent Verhoeff-van Giesen (VVG) staining and were imaged at 40× magnification, using a Nikon Eclipse E400 microscope. Wall thickness of the aortic media was measured by a single blinded observer at 16 different locations around the most proximal ascending aortic ring and averaged. Wall architecture of 4 representative sections for each mouse was assessed by the same 3 blinded observers and graded on an arbitrary scale of 1 (indicating no breaks in the elastic fiber) to 5 (indicating diffuse fragmentation), and the results were averaged. Elastic fiber content was quantified in four separate representative images of each section of the most proximal ascending aorta by a single blinded observer, using NIS Elements Advanced Research (Nikon, Japan). The aortic media and the elastic fibers were individually outlined and their areas calculated. The respective areas were averaged from all the images of a given aortic section and the ratio of elastic fiber content to total aortic media was determined. Aortic root size was measured by echocardiography at six months (baseline before treatment).

Example 3: Identification of Major Genetic Modifiers of Aortic Aneurysm in Marfan Syndrome Marfan syndrome (MFS) is an inherited connective tissue disorder caused by heterozygous mutations in the FBN1 gene. The major cause of mortality is aortic aneurysm, dissection and/or rupture.

Materials and Methods

Mouse Lines:

Mice were cared for under compliance with the Animal Care and Use Committee of the Johns Hopkins University School of Medicine. Fbn1$^{C1039G/+}$ mice on a pure C57BL/6J background were already onsite. Mice on a pure 129S6/SvEvTac background were obtained from Taconic Biosciences (Rensselaer County, N.Y., USA). The Fbn1$^{C1039G/+}$ mice on a pure C57BL/6J background were bred into a pure 129S6/SvEvTac background and backcrossed for >10 generations. Mice haploinsufficient or knockout for Mmp17 (B6.129P2-Mmp17$^{tm1D}$g$^{en}$/J; #005824), Map2k6 (B6.129S1-Map2k6$^{tm1Flv}$/J; #008382) and Map3k4 (B6.129S6-Map3k4$^{tm1Flv}$/J; #008375) were obtained from the Jackson Laboratory (Bar Harbor, Me., USA), and bred to Fbn1C1039G/+ mice. Animals were checked daily for death and all mice found dead were immediately autopsied to assess for evidence of aortic dissection. Mice that were sacrificed were done so using a lethal dose of ketamine and acepromazine (1 ml of 10 mg/ml acepromazine in 10 mls of 100 mg/ml ketamine; MWI Vet, ID, USA). At the time of sacrifice, mice underwent immediate laparotomy and descending abdominal aortic transection. Phosphate buffered saline (PBS) was infused through the right and left ventricles to flush out the blood.

Mouse Drug Treatments:

Losartan was dissolved in drinking water and filtered to reach a concentration of 0.6 g/L, giving an estimated daily dose of 60 mg/kg/day, as described previously (Habashi, J. P. et al. *Science* 312, 117-21 (2006)). Mice were started on losartan at 2 months of age and continued for 8 months. Placebo-treated animals received regular drinking water.

RDEA119 was reconstituted in 10% 2-hydroxypropyl-beta-cyclodextrin (Sigma-Aldrich, Mo., USA) dissolved in PBS, and administered twice daily by oral gavage at a dose of 25 mg/kg, as described previously (Holm, T. M. et al. *Science* 15, 358-61 (2011)). Treatment was initiated at 2 months of age and continued for 2 months. 10% 2-hydroxypropyl-beta-cyclodextrin dissolved in PBS was administered as a control. Erlotinib was reconstituted in 1% methylcellulose (Sigma-Aldrich) dissolved in PBS, and administered daily by oral gavage at a dose of 50 mg/kg. Treatment was initiated at 2 months of age and continued for 2 months. 1% methylcellulose dissolved in PBS was administered as a control.

Mouse echocardiography: Nair hair removal cream was used on all mice the day prior to echocardiography. All echocardiograms were performed on awake, unsedated mice using the VisualSonics Vevo 2100 imaging system and a 30 MHz transducer (Fujifilm VisualSonics, ON, Canada). The aorta was imaged using a parasternal, long-axis view. Three separate measurements of the maximal internal dimension at the sinus of Valsalva and proximal ascending aorta were made from distinct captured images and averaged. All imaging and measurements were performed blinded to genotype and treatment arm.

Mouse Blood Pressure Analysis:

Blood pressures were analyzed by taking 20 tail cuff blood pressures per day over 5 days in each mouse to habituate the mice to the tail cuff blood pressure system (BP-2000, Visitech Systems, USA), and the blood pressures obtained on the last day were averaged.

Mouse Aorta Western Blot Analysis:

Mice that were sacrificed for Western Blot analysis had their proximal ascending aortas immediately dissected, flash frozen in liquid nitrogen and stored at −80° C. until further processing. Protein was extracted using the reagents and protocol from a Total Protein Extraction Kit containing protease inhibitor and Protein Phosphatase Inhibitor Cocktail (Millipore, Mass., USA). Aortas were homogenized using a pellet pestle motor (Kimble-Kontes, N.J., USA) as per the extraction kit protocol. Samples were then stored once more at −80° C. until Western blot analysis was performed. Aortic tissue homogenates were dissolved in sample buffer, run on a NuPAGE Novex 4-12% Bis-Tris Gel (Invitrogen, Calif., USA), and transferred to nitrocellulose membranes using the iBlot transfer system (Invitrogen). Membranes were washed in PBS and blocked for 1 hour at room temperature with 5% instant non-fat dry milk dissolved in PBS containing 1% Tween-20 (Sigma-Aldrich; PBS-T). Equal protein loading of samples was determined by a protein assay (Bio-Rad, Calif., USA) and confirmed by probing with an antibody against β-Actin (Sigma-Aldrich #A5316). Membranes were probed overnight at 40 centigrade with primary antibodies against pSmad2 (Cell Signaling, Mass., USA #3108), pSmad3 (Cell Signaling #9250), pErk1/2 (Cell Signaling #4370), pMek1 (Cell Signaling #9154), pp38 (Cell Signaling #4511), pJnk1/2 (Santa Cruz #6254), pPkcj3 (Cell Signaling #9371), and pEgfr (Cell Signaling #3777), dissolved in PBS-T containing 5% milk. Blots were then washed in PBS-T and probed with HRP-conjugated anti-rabbit or anti-mouse secondary antibodies (GE Healthcare, UK #NA934) dissolved in PBS-T containing 5% milk for 1 hour at room temperature. Blots were then washed in PBS-T, developed using SuperSignal West Femto HRP substrate (Pierce Scientific, Ill., USA), exposed to BioMax Scientific Imaging Film (Sigma), and quantified using ImageJ analysis software (NIH, Md., USA).

Mouse Lung Tissue Collection and Analysis:

Mice that were sacrificed for lung histology had their trachea intubated with a 20-gauge blunt needle; 0.5% agar was infused under low and constant pressure using direct manometry to inflate the lungs. The trachea was then tied-off using an 8-0 Vicryl suture and the needle was removed. Samples were fixed for 24 hours in 10% buffered formalin and then stored in 70% ethanol. Individual lobes of the lungs were mounted in 4% agar and fixed in paraffin. Five micrometer lung sections underwent hematoxylin and eosin staining and were imaged at 10× magnification, using a Nikon Eclipse E400 microscope. Five fields were analyzed for each lobe of each lung by a single blinded observer, and a mean linear intercept was calculated as described previously (Neptune, E. R. et al. *Nature Genetics* 33, 407-11 (2003)).

Mouse skeletal X-ray analysis: Mice undergoing spine X-ray were anesthetized using a combination of ketamine and xylazine (1 ml of 100 mg/ml ketamine and 100 µl of 100 mg/ml xylazine in 10 mls of PBS; MWI Vet). They were placed in the left lateral decubitus position on a radiolucent platform with adjacent scale bar and imaged at 1× magnification using a Faxitron MX20 (Faxitron, Ariz., USA). The output electronic file was processed using ImageJ analysis software (NIH). Spine kyphosis was quantified using a modified kyphosis index (Laws, N., Hoey, A. *J. Appl. Physiol.* 97, 1970-7 (1985)). In brief, a line was drawn from the anterior superior iliac spine to the point of maximal lordosis of the cervical spine. A line was then drawn perpendicular from this line to the anterior aspect of the vertebral body at the point of maximal thoracic kyphosis.

Mouse whole genome analysis: SNPs were selected from the Illumina mouse medium density linkage panel array that were divergent between the C57BL/6J and 129S6/SvEvTac background strains. Genotyping was performed using an Illumina mouse medium density linkage panel, and was run using standard GoldenGate chemistry on an iScan microarray scanner (Illumina, Calif., USA). Genotypes were called using Illumina GenomeStudio software (GenomeStudio 2011.1, Genotyping Module 1.9.4 and Gentrain version 1.0). The average physical coverage was 2.9 Mb, the maximum gap was 22.4 Mb and there were 10 gaps >12 Mb. The genotype quality score cut-off for a "no call" genotype was 0.25. Only SNPs of sufficient quality were used for downstream analysis. R/qtl software (rqtl.org; Broman K. W., Sen S. (2009) Introduction. In: A Guide to QTL Mapping with R/qtl. Statistics for Biology and Health. Springer, New York, N.Y.) was utilized to calculate LOD scores for the whole-genome SNP analysis. All of the animals for which there was both genotype and phenotype data were included in the analysis; mice were only included if they were either BL6 or 129 throughout the whole ROI on a given chromosome. First, the "scanone" function was used to perform a single-QTL genome scan utilizing a nonparametric model and 1000 permutations. The results were expressed as a LOD score and p-value. The "scanone" function calculated the genome-wide LOD significance threshold for this dataset as 3.82. Next, the "scantwo" function was used to perform a two-dimensional genome scan with a two-QTL model utilizing a binary model. The recommended significance threshold for a mouse intercross using this function was a MfLOD >9.1. Since the "scantwo" function does not compute a p-value, we performed ANOVA plus a post-hoc linear trend test of the raw continuous data to generate a p-value for the 129 allele dose-response graph.

Families with Marfan Syndrome:

The 5 families were recruited from the Connective Tissue Clinic at Johns Hopkins Hospital and Ghent University Hospital. The diagnosis of MFS was made in accordance with the revised Ghent nosology (Loeys, B. L., et al. Revised Ghent criteria for the diagnosis of Marfan syndrome (MFS) and related conditions. *J. Med. Genet.* 47, 476-485 (2010)). Echocardiograms were performed and interpreted as previously described (Brooke B. S., et al. *N. Engl. J. Med.* 358, 2787-95 (2008)). Aortic root aneurysm was defined by a maximal aortic root Z score >2.0. All blood samples and skin biopsies were collected in compliance with the Institutional Review Board after informed consent was obtained. DNA was extracted from 5 mL whole blood using a DNeasy blood and tissue kit (Qiagen, Calif., USA). For the purposes of genome wide linkage analysis, individuals harboring an FBN1 mutation were classified as affected; they were assigned a severe status if they had an aortic root Z score >3.0, a history of aortic root dissection or a history of aortic root surgery; they were assigned a mild status if they had an aortic root Z-score <2.0 or had reached age 60 years without prior aortic root dissection or aortic root surgery; those with a Z score 2.0-3.0 were classed as indeterminate. Individuals without an FBN1 mutation were classified as unaffected.

Human Whole Genome Analysis:

The DNA was digested, amplified, and hybridized to either a Genome-Wide Human SNP Nsp/Sty Array 5.0 or 6.0 according to the manufacturer's recommended protocol (Affymetrix, Calif., USA). The arrays were then scanned using a GeneChip Scanner 3000 7G (Affymetrix). The genomic location of each marker was determined from the Affymetrix Genetic Map (Affymetrix). SNPs were selected that were present on both the Affymetrix 5.0 and 6.0 Array using PLINK. Allele frequencies for this SNP set were calculated using PLINK. Tests for Hardy-Weinberg equilibrium (HWE) and Mendelian errors were calculated for autosomal SNPs using Pedstats. Tests for HWE were calculated for sex chromosome SNPs using PLINK, and Mendelian errors using Pedstats. Subsequently, the following quality control filters were applied using PLINK; <1% missing data, minor allele frequency (MAF)>0.2, no Mendelian errors and HWE p>0.05. Statistically unlikely genotypes were then filtered using the error-checking algorithm in MERLIN/MinX. As a last step, SNPs that were in complete linkage disequilibrium with a proximate SNP ($r^2=1$) were excluded using PLINK to produce a list of SNPs of outstanding quality. Prior to genome wide linkage analysis, the dataset was simplified whilst maintaining uniform coverage across the genome by only including every $10^{th}$ consecutive SNP. Parametric linkage analysis was performed following the maximized maximum LOD score (MMLS) procedure with the restricted set of SNPs using MERLIN/MinX. The analysis was performed twice, once under a dominant model and once under a recessive model, considering a low sporadic rate (0.0002), an arbitrary penetrance (0.50 and 0.80 for one and two alleles respectively), and arbitrary gene frequencies (0.01 for the dominant model and 0.1 for the recessive model). The limits of the regions of interest were defined by the closest neighboring upstream and downstream SNP markers with LOD scores >1 levels below the peak identified by parametric linkage analysis. Haplotypes were established for all genotyped individuals across the regions of interest. Since the mode of inheritance and the penetrance of the modifier region were uncertain, the segregation of haplotypes between individuals classified as affected with mild disease was examined first. Next individuals classified as affected with severe disease were incorporated into this analysis. The NCBI mapviewer (cbi.nlm.nih.gov/projects/mapview; Wolfsberg, T. G. 2010. Using the NCBI Map Viewer to Browse Genomic Sequence Data. *Current Protocols in Bioinformatics.* 29:1.5:1.5.1-1.5.25.) was used to identify candidate genes contained within haplotypes of interest.

Human DNA Sequencing Analysis:

Candidate genes were cycle sequenced across all exons, exon/intron boundaries and potential non-coding functional variants from the ENCODE dataset (defined as SNPs in regions associated with DNase hypersensitivity, transcription factor occupancy, histone modification and a MAF<0.15) in 2 individuals with mild disease and 2 individuals with severe disease from each family. Firstly, targeted segments of DNA were amplified by PCR using a DNA Engine Dyad thermal cycler (Bio-Rad). Next, the samples were purified using QIAquick PCR purification kit (Qiagen). Finally, cycle sequencing was performed using BigDye Terminator v3.1 kit and an ABI 3730xl DNA Analyzer/sequencing machine in accordance with the manufacturer's instructions (Life Technologies, Calif., USA).

Human Dermal Fibroblast Quantitative RT-PCR Expression Analysis:

Primary human dermal fibroblasts were derived from forearm skin biopsies from 2 control individuals, 2 patients in family B with severe aortic disease and 2 patients from family B with mild aortic disease. Cells were incubated in T-75 flasks at 37° C. with 95% air and 5% CO2 whilst submerged in Dulbecco's modified eagle medium (Gibco, Life Technologies) containing 10% fetal bovine serum (Sigma-Aldrich), antibiotics and antimycotic (Gibco). Media was replaced every 3 days. Cells were passaged at 95-100% confluence. Cells were collected using TRIzol (Life Technologies) and immediately stored at −80° C. RNA was extracted using a miRNeasy mini kit according to the manufacturer's instructions (Qiagen). Quantitative RT-PCR was performed using a RNA-to-CT 1-step Kit and an ABI 7900HT Fast Real-Time PCR System in accordance with the manufacturer's instructions (Life Technologies). The following pre-validated probes were used for analysis: Hs01060665 (β-ACTIN) and Hs00245958_m1 (MAP3K4) (Life Technologies).

Statistical Analysis:

All quantitative data are shown as bar graphs produced using Excel (Microsoft, Wash., USA). Mean±2 standard errors of the mean (SEM) are displayed. Statistical analyses were performed using two-tailed t tests. A p-value <0.05 was considered statistically significant for all tests.

Results

Figure 1B:
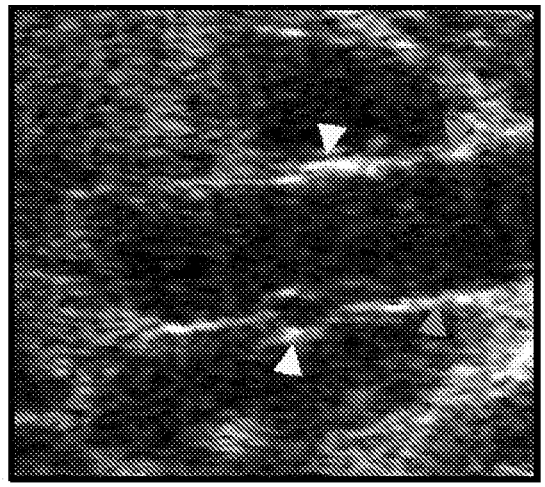
Figure 1B:
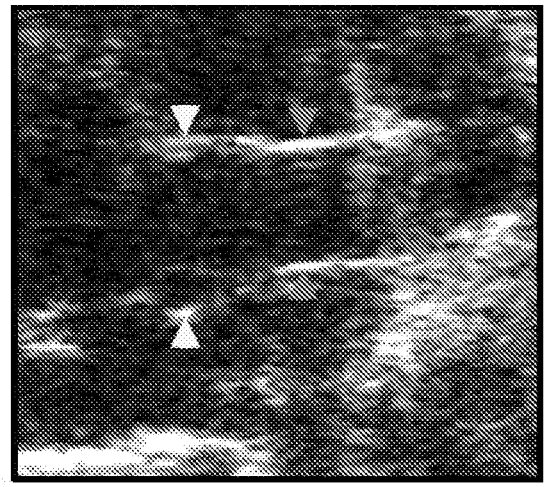
Figure 1B:
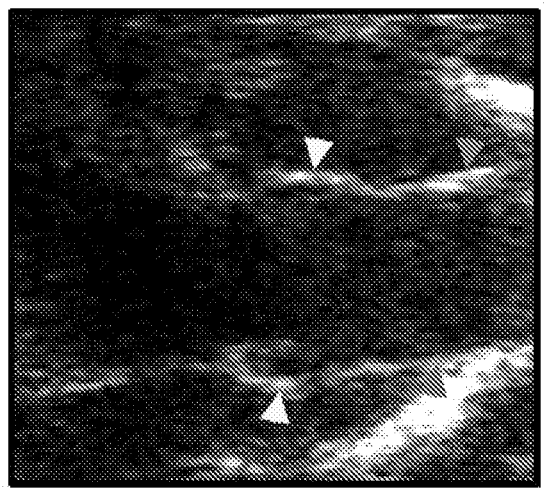
Figure 1B:
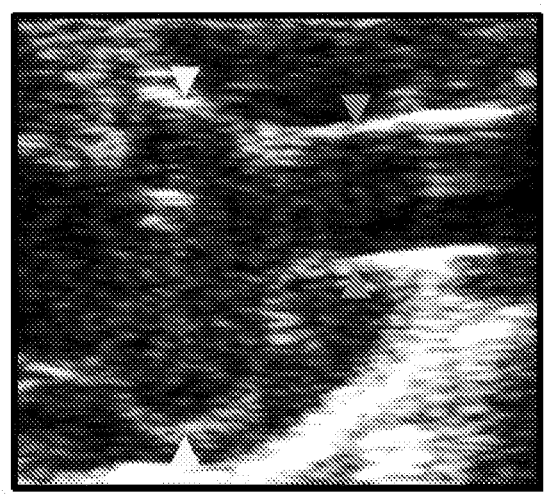
Figure 5:
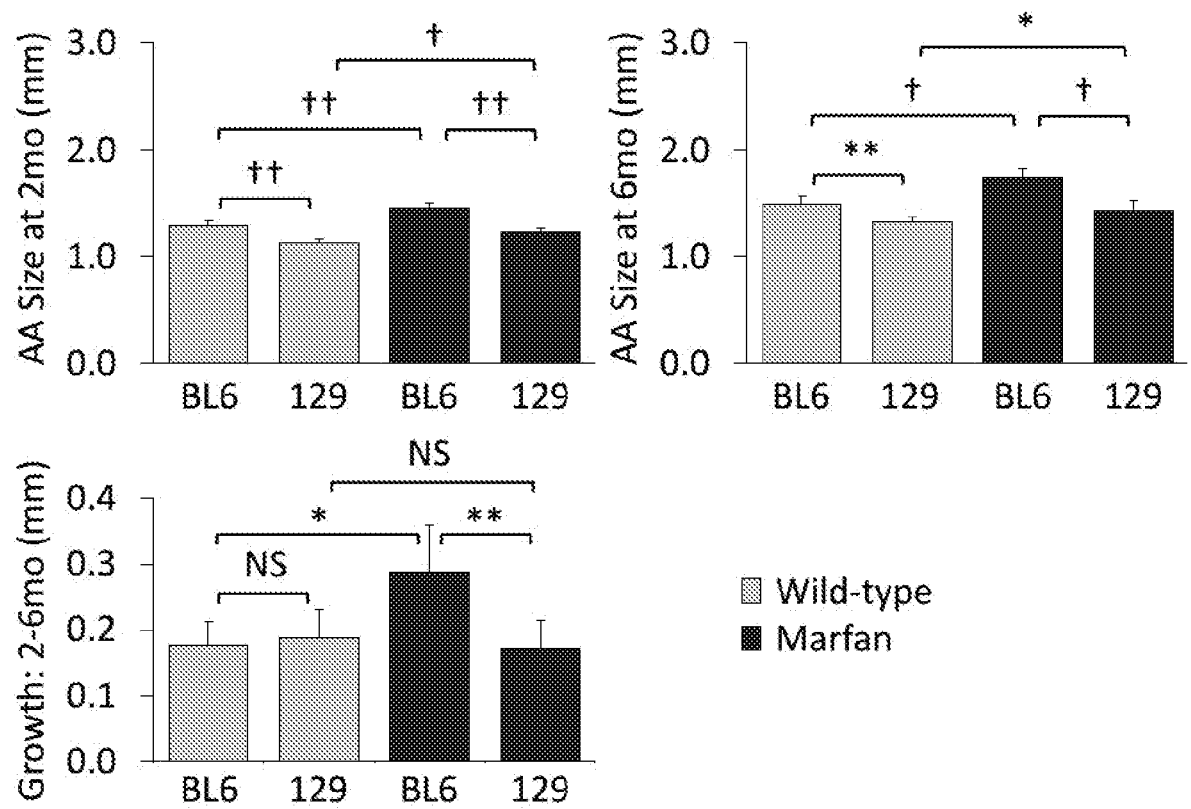
FIG. 5 shows the ascending aortic size (mm) in BL6 (n=16) and 129 (n=13) WT mice, and BL6 (n=15) and 129 (n=15) MFS mice at 2 and 6 months of age, and postnatal growth (mm) from 2 to 6 months. AA: Ascending aorta; *<0.05, **<0.01, †<0.001, ††<0.0001, NS non-significant.

Mice were characterized as heterozygous for a disease-causing Fbn1 allele ($Fbn1^{C1039G/+}$) on a pure C57BL/6J mouse background (hereafter termed BL6 MFS mice). These mice have been shown to recapitulate multiple manifestations of the disease, including aortic root aneurysm, developmental lung emphysema, and skeletal deformity (Neptune, E. R. et al. *Nature Genetics* 33, 407-11 (2003); Habashi, J. P. et al. *Science* 312, 117-21 (2006); Judge, D. P. et al. *J. Clin. Invest.* 114, 172-81 (2004)), although the severity of the manifestations is on the milder end of the human phenotypic spectrum. In the present study, these $Fbn1^{C1039G/+}$ mice were backcrossed greater than 10 generations onto a 129S6/SvEvTac background (hereafter termed 129 MFS mice), to assess the impact of mouse strain on MFS disease phenotype. Aortic root size at 2 and 6 months of age, and post-natal aortic root growth from 2 to 6 months, were greater in 129 MFS mice, compared to their BL6 MFS counterparts (FIGS. 1A, 1B yellow arrows). This strain-dependent modification of aortic size was absent in wild-type (WT) littermates, showing it to be a MFS disease-specific effect. Furthermore, the 129 strain did not exacerbate growth of the more distal ascending aorta in MFS mice (FIGS. 5, 1B red arrows), indicating that this strain-specific exacerbation only occurs at sites of underlying disease predisposition, as opposed to a more generalized loss of arterial homeostasis.

Figure 1C:
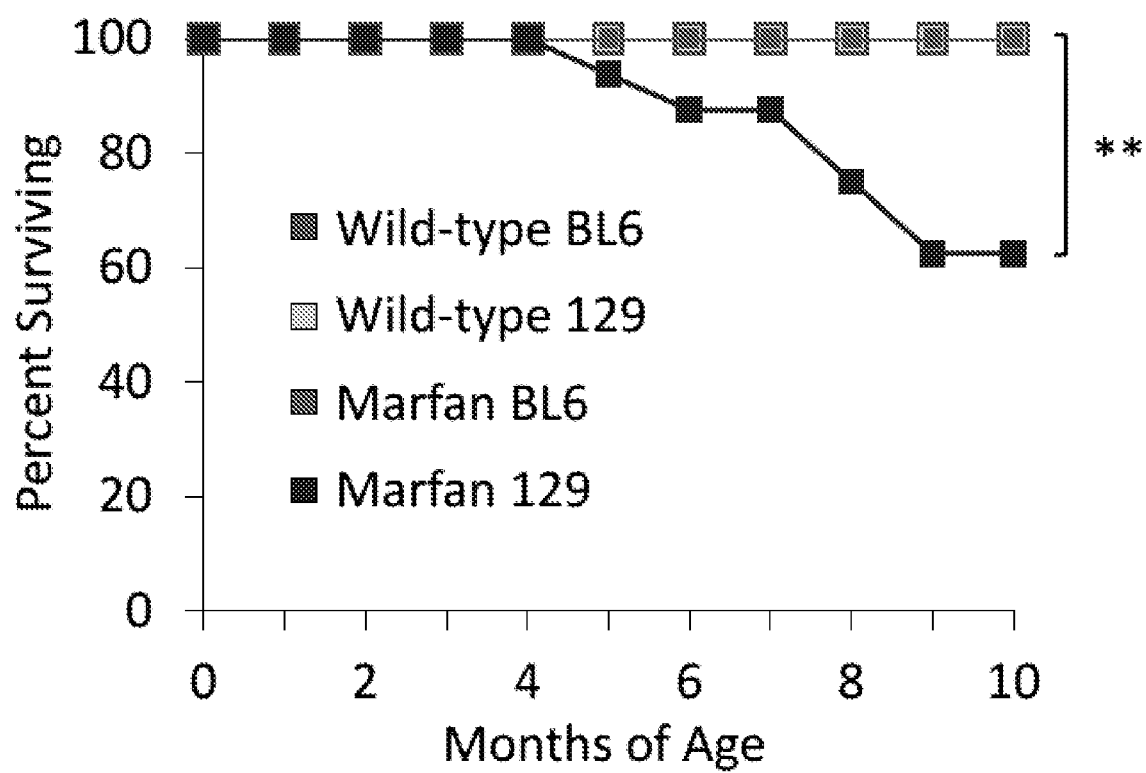
Figure 6:
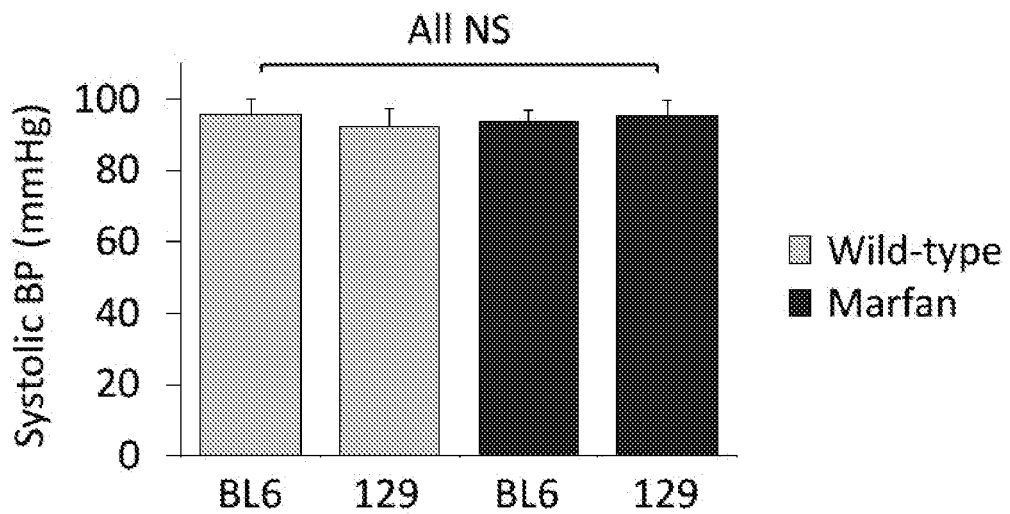
FIG. 6 shows the systolic blood pressure (BP) at 6 months of age in WT and MFS mice on pure BL6 and 129 strains (n=5 per group). NS: non-significant.
Figure 7:
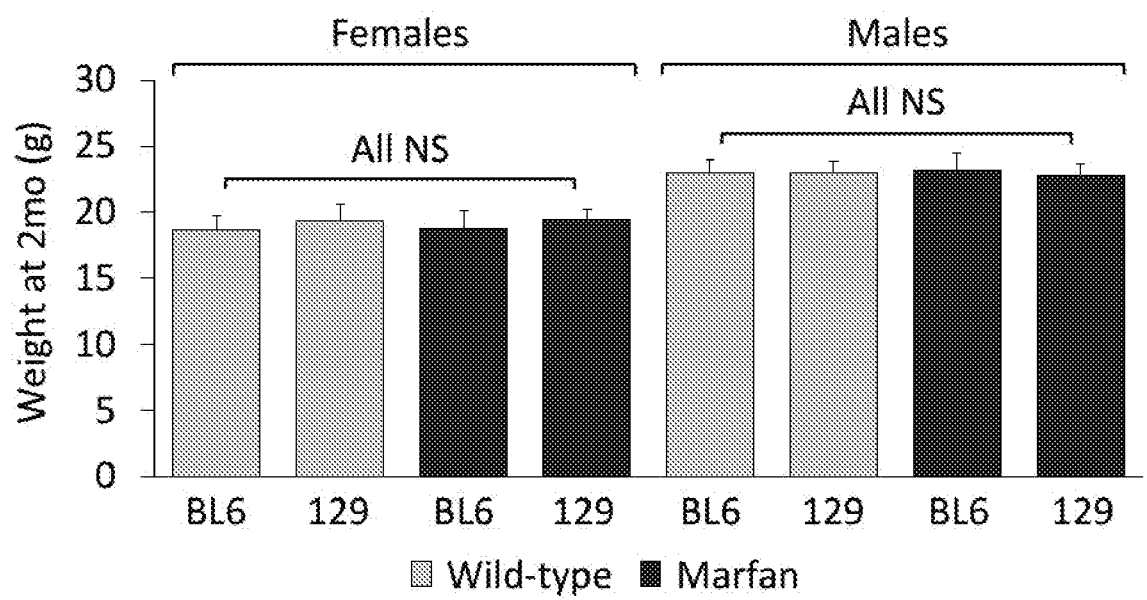
FIG. 7 shows the weight (in grams) at 2 months of age in female and male WT and MFS mice on pure BL6 and 129 strains (n>10 per group). NS non-significant.
Figure 8:
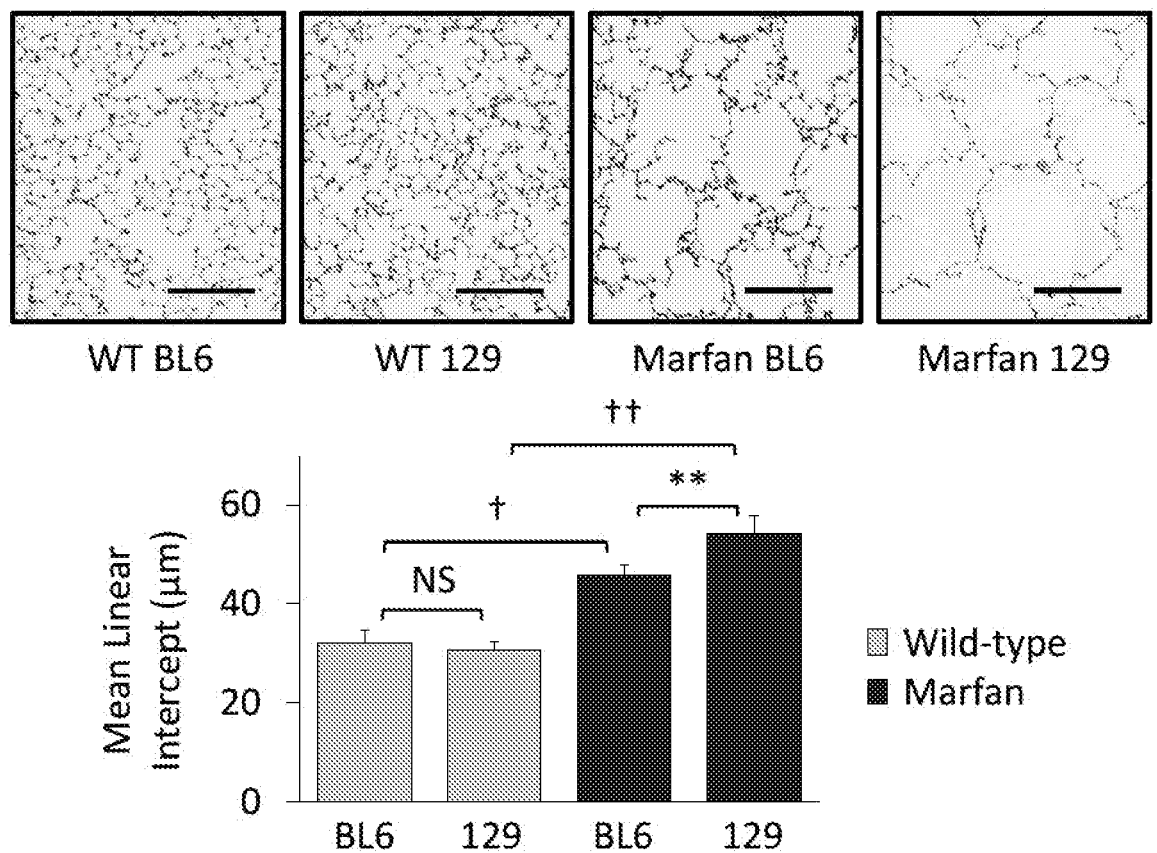
FIG. 8 shows representative sections of lung alveoli, and mean linear intercept (MLI; μm) in 10-month old WT and MFS mice on pure BL6 and 129 strains (n=5 per group). Line: 50 μm. **<0.01, †<0.001, ††<0.0001, NS non-significant.
Figure 9:
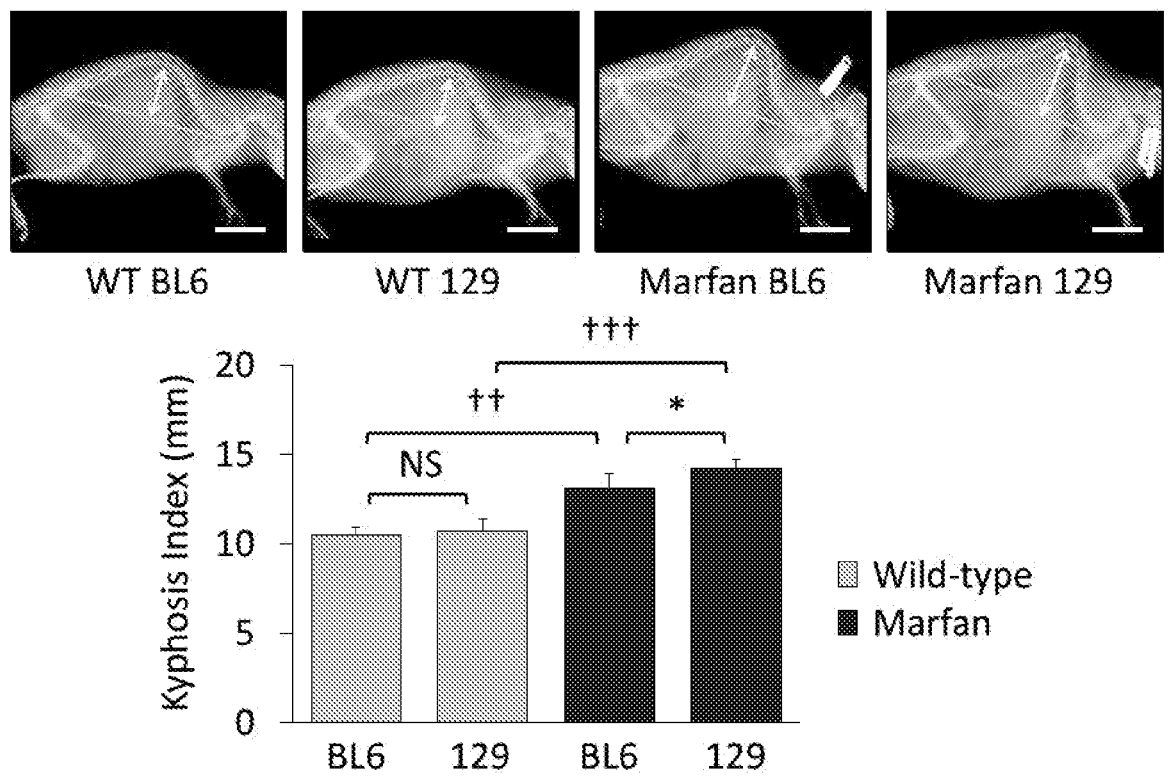
FIG. 9 shows representative spine x-rays and mean modified kyphosis index (length of yellow arrow; mm) in 10-month old WT and MFS mice on pure BL6 and 129 strains (n=10 per group). Line: 10 mm. *<0.05, ††<0.0001, †††<0.00001, NS non-significant.

Compared to BL6 MFS mice, 129 MFS animals died prematurely secondary to aortic dissection and/or rupture (FIG. 1C). This was independent of hemodynamic status, weight or gender (FIGS. 6, 7). Compared to BL6 MFS animals, 129 MFS mice also had worse lung disease as measured by mean linear intercept (MLI; FIG. 8; Neptune, E. R. et al. *Nature Genetics* 33, 407-11 (2003)), and worse spine kyphosis as measured by a modified kyphosis index (KI; FIG. 9; Laws, N., Hoey, A. *J. Appl. Physiol.* 97, 1970-7 (1985)). Of note, in 129 MFS mice there was an individual correlation between aortic root size and both lung MLI ($r^2$=0.75, p=0.012) and spine KI ($r^2$=0.30, p=0.013).

Figure 2A:
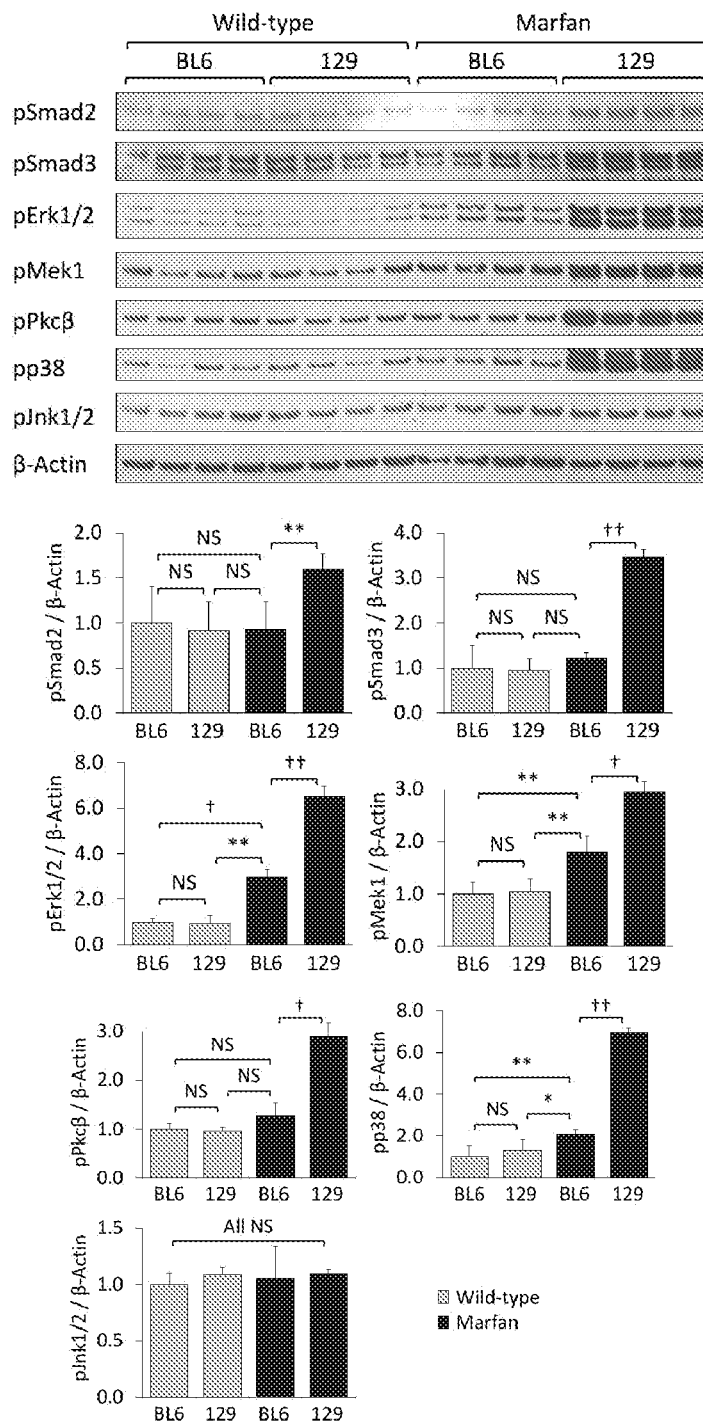
FIGS. 2A-2E show the molecular mechanisms driving aortic disease in MFS mice.
Figure 2B:
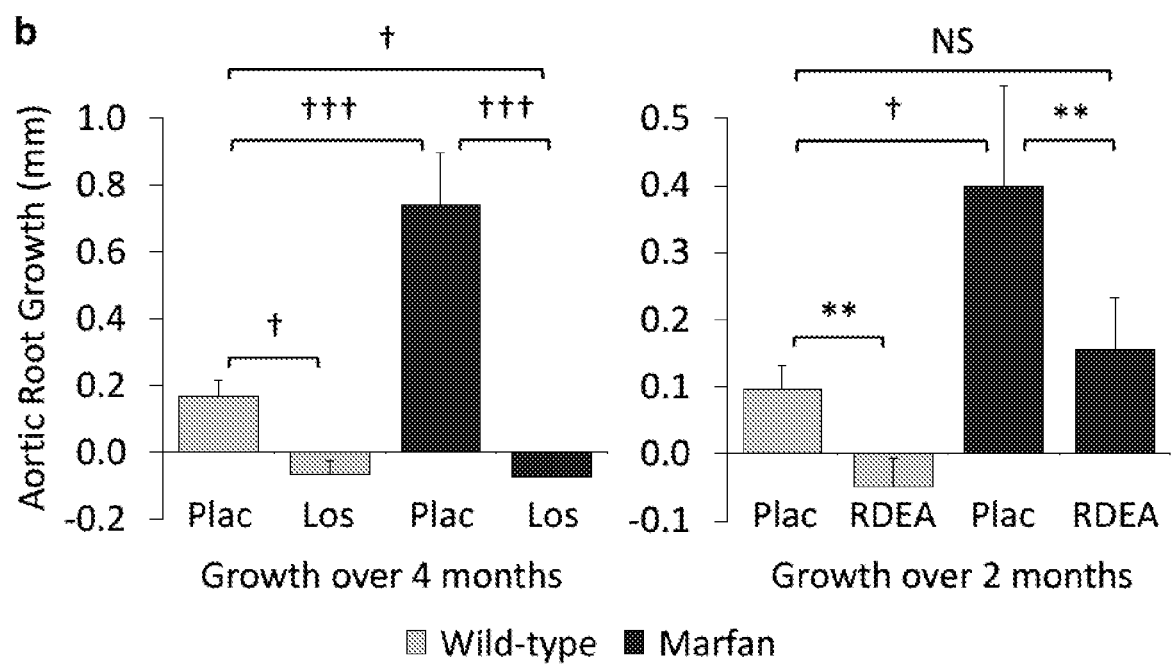
Figure 2C:
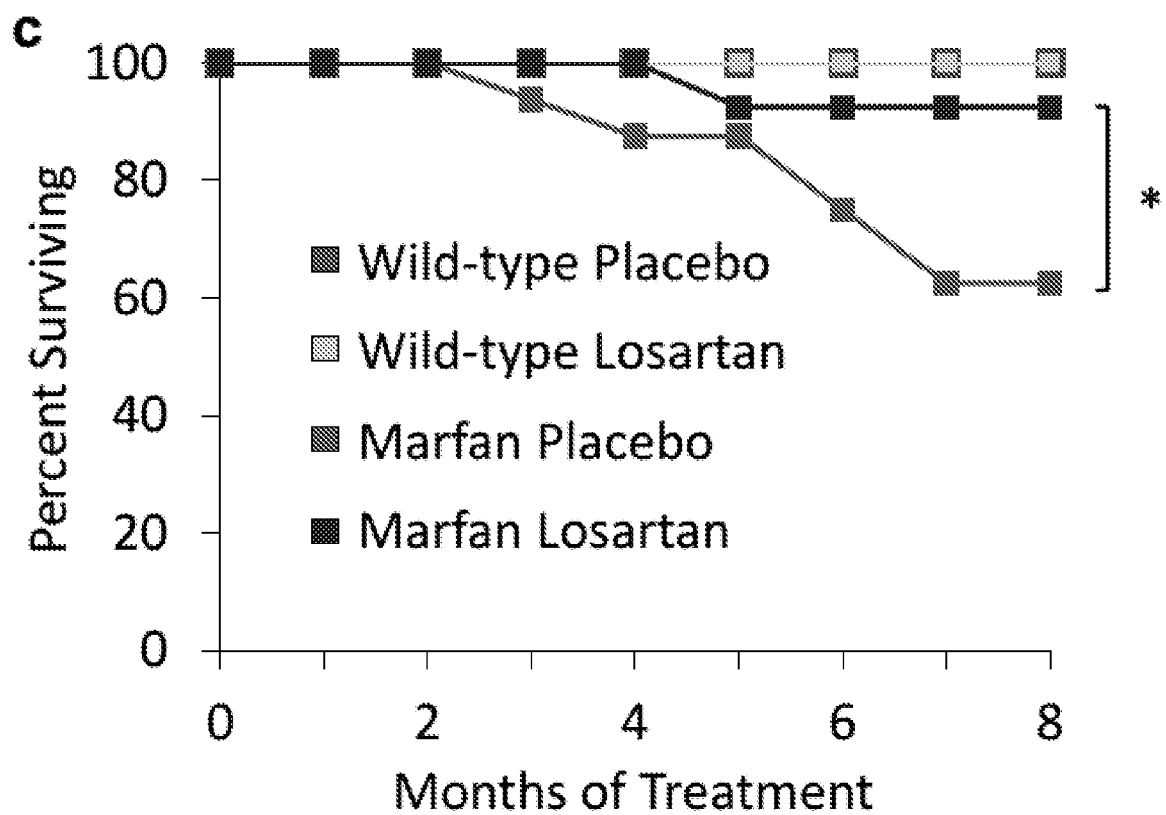
Figure 2D:
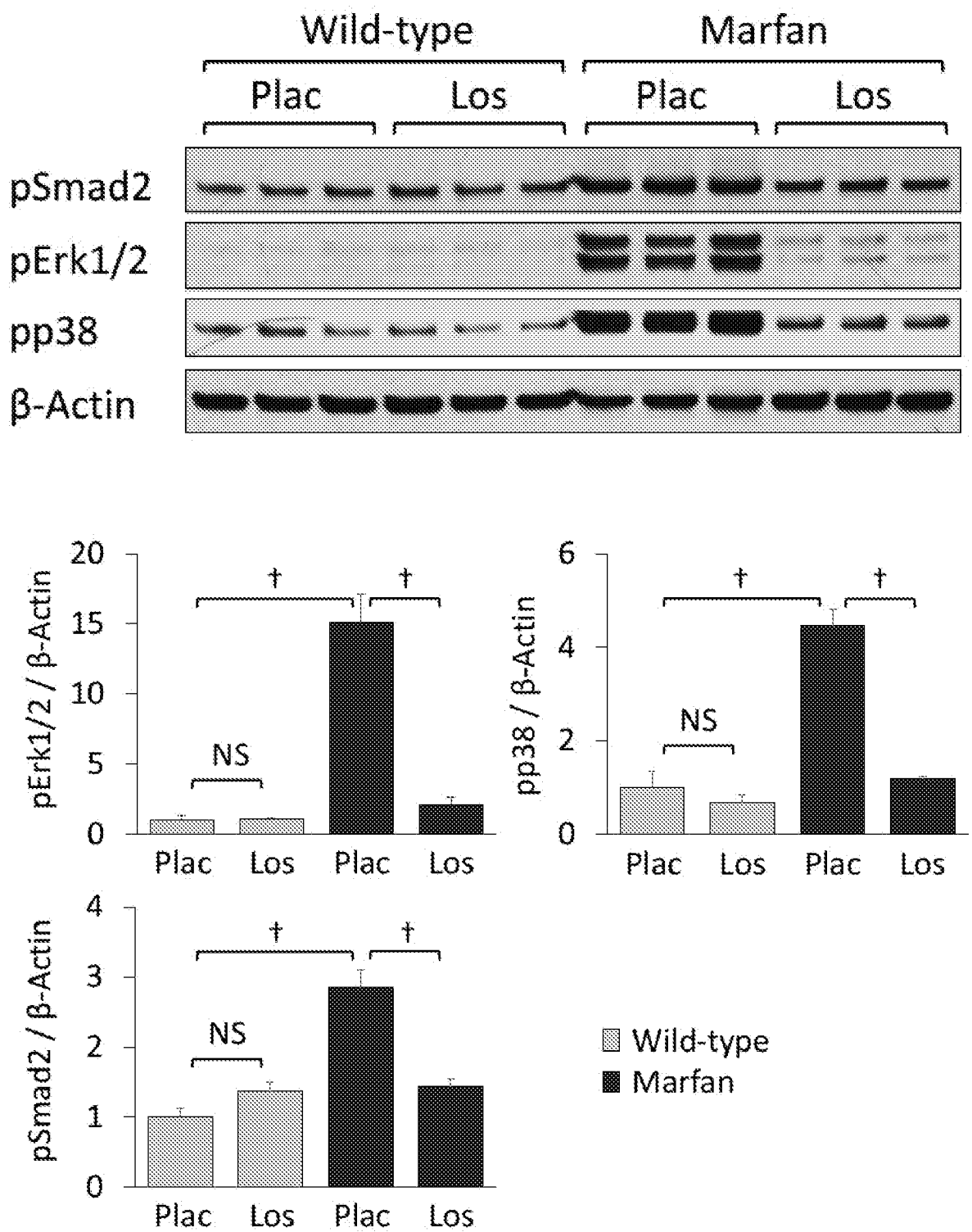
Figure 2E:
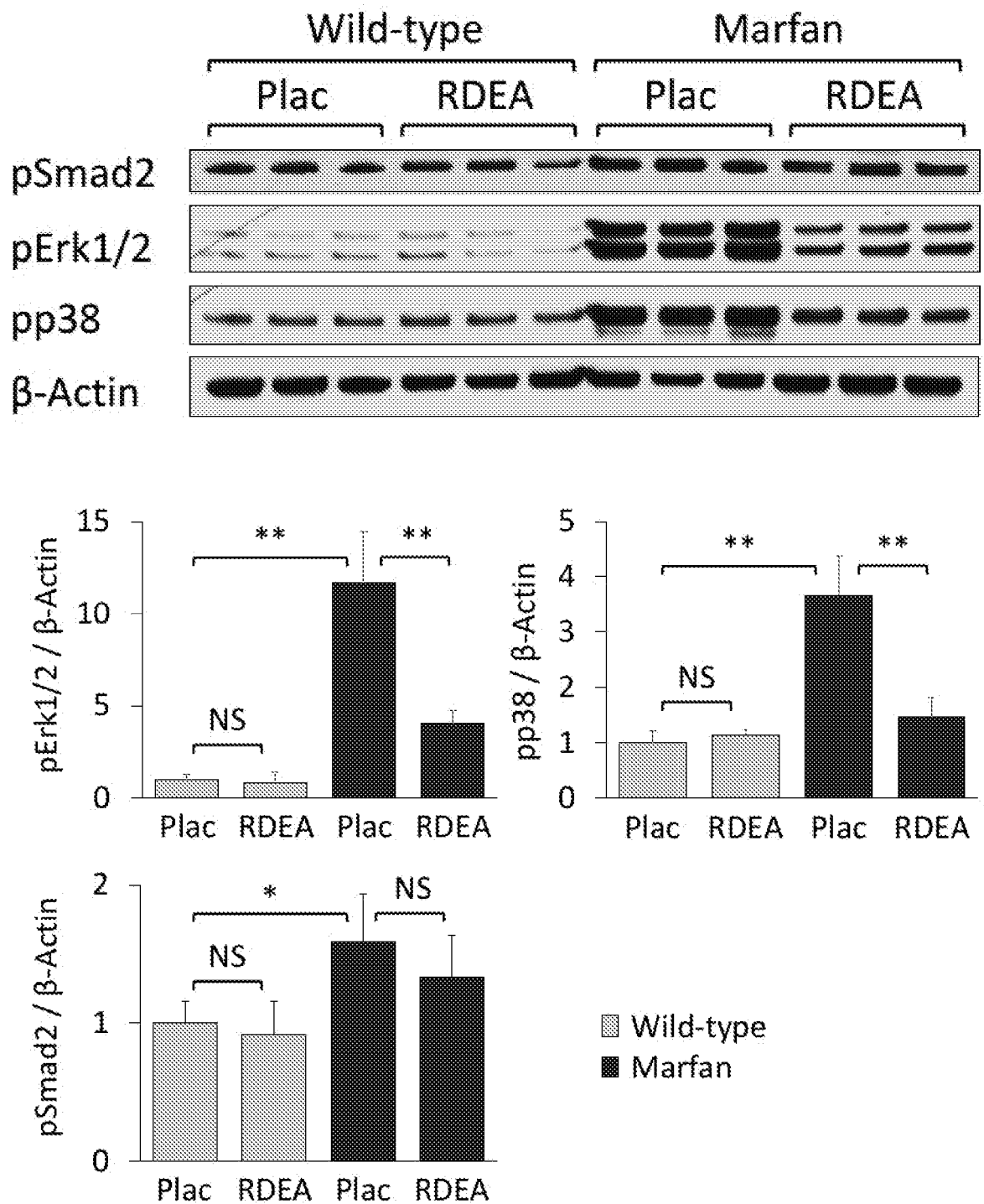

To assess the mechanism driving disease exacerbation, Western blot analysis was performed on the aortic root of 10-month old animals. Compared to BL6 MFS mice, 129 MFS animals showed greatly enhanced activation of pathways previously shown to be operative in MFS mice, including Smad2/3, Erk1/2 and its upstream activator Mek1, p38, and PKCI3 (FIG. 2A). Jnk1/2 activation remained unaffected, suggesting selective, rather than global modulation of MAPK signaling. There were no differences in activation of any of these pathways in WT animals on the two backgrounds, indicating MFS disease-specific modification. Treatment of 129 MFS mice with either the ARB losartan or the inhibitor of Erk1/2 activation RDEA119, reduced aortic root growth to a rate equal to that of WT animals (FIG. 2B). Furthermore, losartan ameliorated premature lethality in 129 MFS mice (FIG. 2C). This correlated with a reduction in both canonical (Smad2) and noncanonical (Erk1/2, p38) TGFβ signaling cascades in losartan-treated 129 MFS mice (FIG. 2D), and a selective reduction in noncanonical (Erk1/2, p38) cascades in RDEA119-treated 129 MFS animals (FIG. 2E). Taken together, these data illustrate that the 129 strain exacerbates signaling cascades known to be upregulated in BL6 MFS mice, and therapies targeting these pathways are highly efficacious even against the more severe disease seen in 129 MFS animals.

Figure 3A:
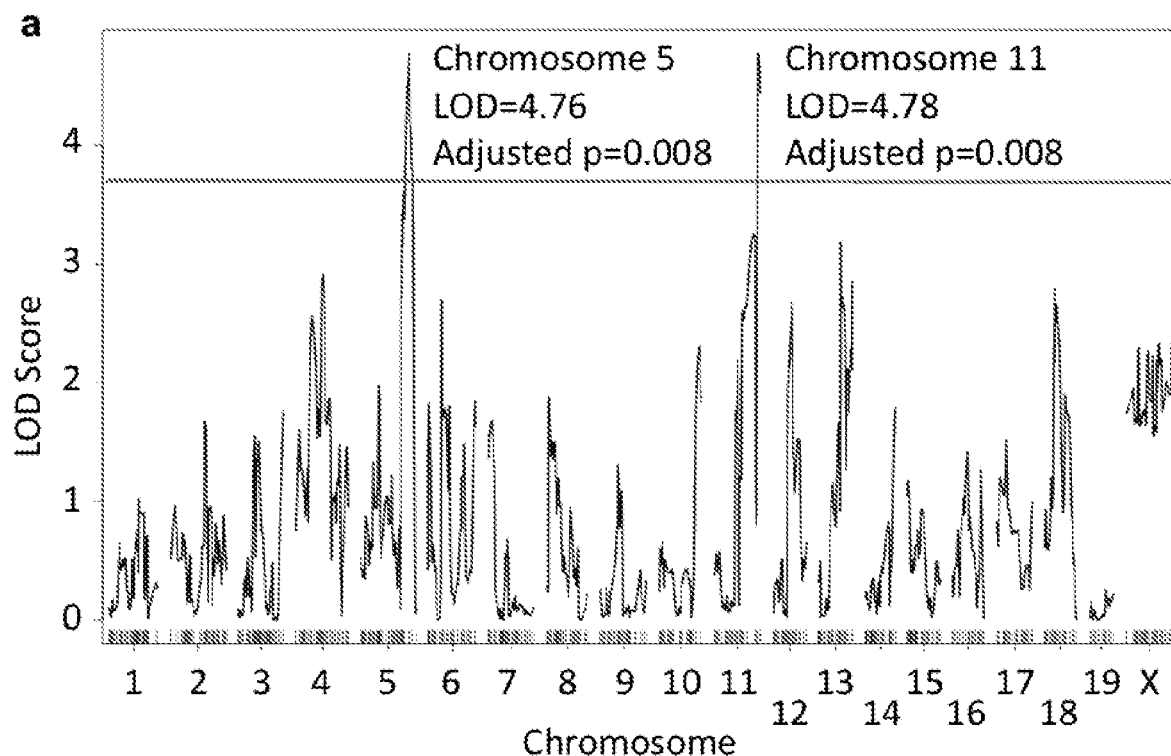
FIGS. 3A-3G show the mapping modifier loci of aortic aneurysm in MFS mice.
Figure 3B:
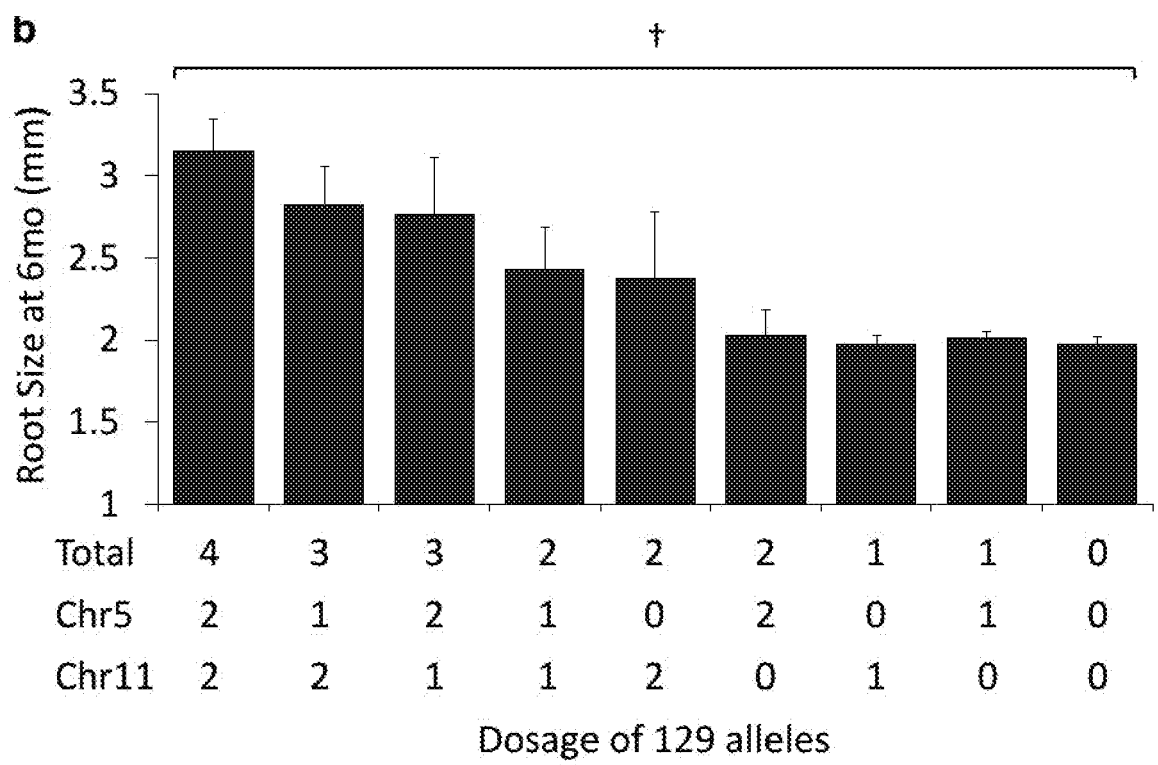
Figure 10:
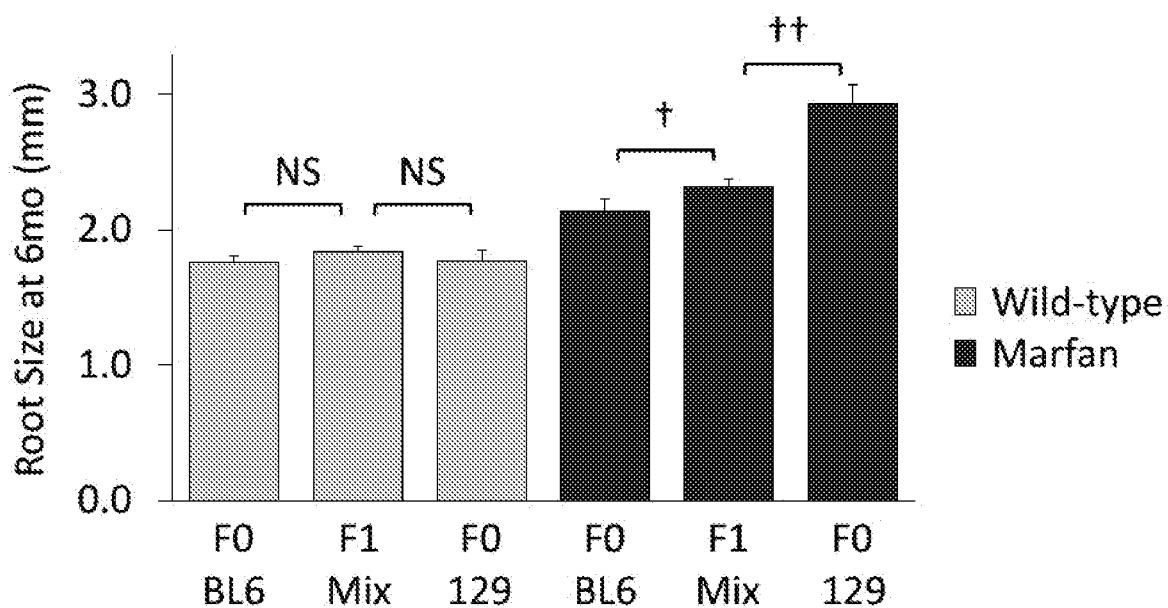
FIG. 10 shows the aortic root size (mm) at 6 months of age in WT and MFS mice on pure (F0 generation) BL6 and 129 strains (n as per FIG. 1A), and F1 generation intercrossed WT (n=20) and MFS (n=21) mice. †<0.001, ††<0.0001, NS non-significant.

To identify modifier loci for the MFS aortic phenotype, MFS mice were interbred on the 2 pure strains to generate MFS animals on a mixed genetic background. The F1 generation MFS mice displayed an aortic root size that was intermediate between the 2 parental strains (FIG. 10). Mice from the F1 and later generations were interbred to produce a 7-generation pedigree that contained circa 300 MFS mice possessing a range of aortic aneurysm severity. Genome-wide linkage analysis was performed on 35 MFS mice with mild aortic aneurysm (root size <2.20 mm at 6 months), and 40 MFS mice with severe aortic aneurysm (root size >2.70 mm at 6 months). Two loci were identified that strongly linked with aortic severity on chromosomes 5 and 11, both of which exceeded the LOD score threshold of 3.82 to achieve genome wide significance (FIG. 3A), with evidence of epistasis between the loci (MfLOD=12.8). The regions of interest (ROI) were defined as those flanked by individual markers that surpassed genome wide significance; these included 14.7 Mb on chromosome 5 (128,433,315-143,149,098 bp) and 8.9 Mb on chromosome 11 (106,799,515-115,722,120 bp). When 129 allele dose at these ROI was plotted against aortic root size at 6 months of age in the F2 generation interbred mice, there was a clear dose-response, with more 129 alleles (0 to 4) correlating with increased aortic size (p=0.0006; FIG. 3B).

Table 6 shows candidate functional variants that differed between the BL6 and 129 strains within the regions of interest on chromosomes 5 and 11 identified using the mouse genome project online repository that were disfavored by PROVEAN.

TABLE 6

| Chr | Gene | Residue | Score | Prediction |
|---|---|---|---|---|
| 5 | Mmp17 | p.X579W | 9aa deletion | Stop-Loss |
| 5 | Tfr2 | p.G42V | −3 | Disfavored |
| 5 | Zkscan | p.R246W | −3 | Disfavored |
| 5 | Fzd10 | p.S389R | −1 | Disfavored |
| 5 | Rimbp2 | p.D1062H | −1 | Disfavored |
| 11 | Map2k6 | p.G76E | — | Disfavored |
| 11 | Bptf | p.R2360C | −3 | Disfavored |
| 11 | Helz | p.L1498P | −3 | Disfavored |
| 11 | Sdk2 | p.L1501P | −3 | Disfavored |
| 11 | Ccdc46 | p.E507G | −2 | Disfavored |
| 11 | Grin2c | p.P1098H | −2 | Disfavored |
| 11 | SIc9a3r1 | p.P182S | −1 | Disfavored |
| 11 | Grin2c | p.P970L | −1 | Disfavored |

Candidate functional variants were sort within both loci that differed between the 2 strains using the mouse genome project online repository (Table 6). Only 1 variant at each locus was predicted to be both functional and located in a gene likely to influence TGF3/MAPK signaling. On chromosome 11, a missense point mutation was identified in Map2k6, a known member of the MAPK signaling cascade, which was predicted to significantly alter protein function (rs51129320; n.11:110490856-110490856G>A; c.G227A; p.G76E; PROVEAN score -3.66). On chromosome 5, the BL6 strain encodes a premature termination codon in Mmp17 relative to the 129 strain (rs29636438; n.5: 129606538-129606538G>A; c.A1737G; p.X579W), which creates a truncated protein that is missing the terminal 9 amino acids (FIG. 11). This hydrophobic sequence at the C-terminus is critical to the protein's ability to anchor to the extracellular side of the cell membrane via a GPI anchor. Loss of the terminal 9 amino acids in BL6 mice was predicted to significantly alter the hydrophobicity profile of the C-terminal segment, reducing the efficiency of GPI attachment and decreasing the amount of functional protein at the cell surface compared to the 129 strain (Galian C., et al. *J. Biol. Chem.* 287, 16399-409 (2012); Yan W., et al. *J. Mol. Biol.* 275, 25-33 (1998)). Given that both Map2k6 and Mmp17 are expressed in the vasculature and are reported to be positive effectors of TGF3/MAPK signaling (Paye, A., et al. *Cancer Res.* 74, 6758-70 (2014); Han, J., et al. *J. Biol. Chem.* 271, 2886-91 (1996)), it was hypothesized that both variants would likely induce a loss of function on the BL6 background.

Figure 3C:
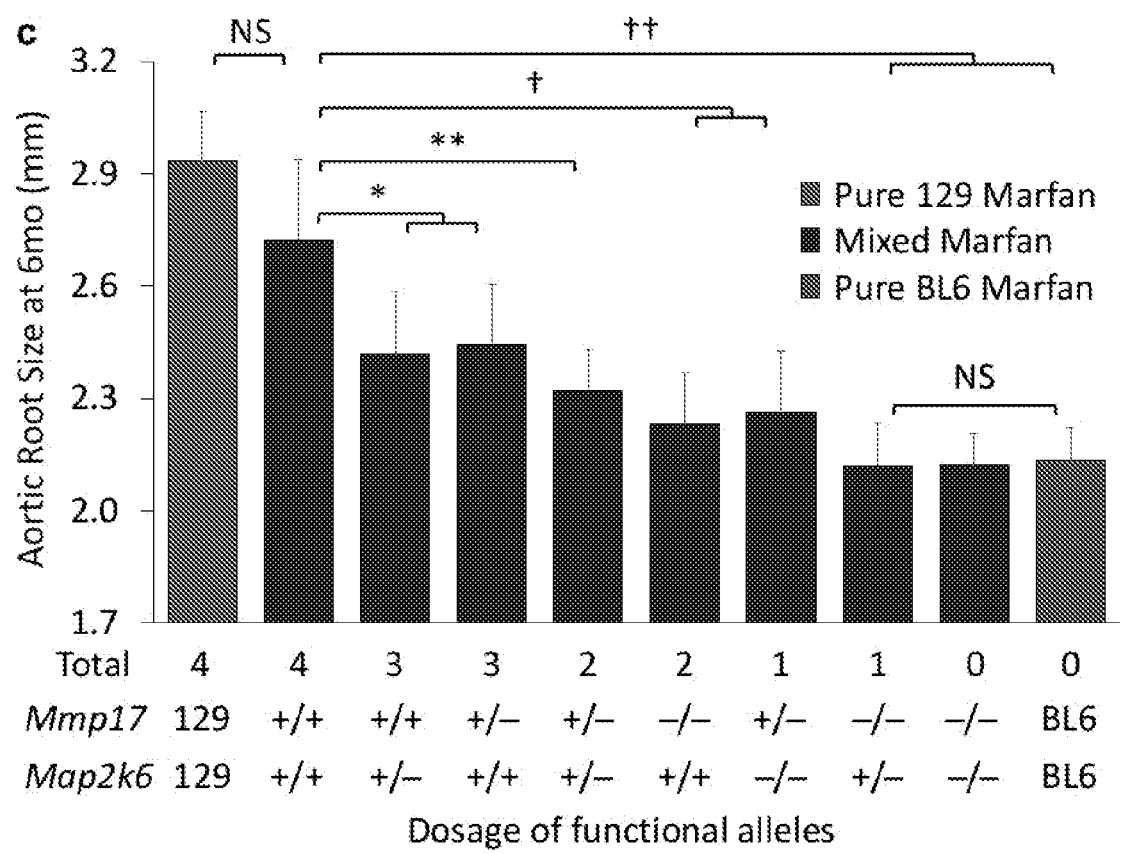
Figure 3D:
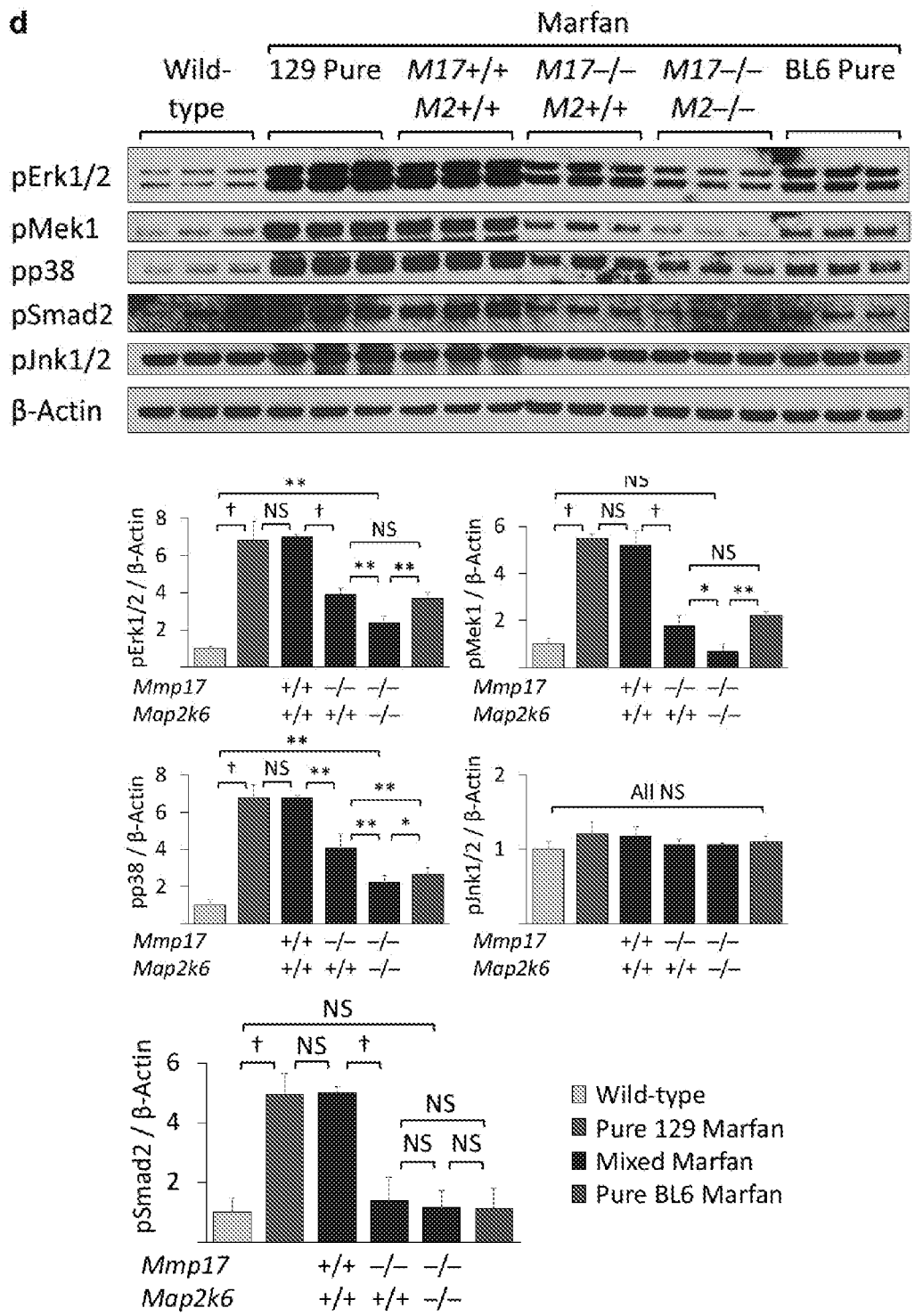

Mmp17 and Map2k6 knockout mice (Mmp17$^{-/-}$ and Map2k6$^{-/-}$) were obtained from Jackson laboratories on a mixed BL6/129 background. These were crossed to 129 MFS mice to generate MFS animals with predominant but variable 129 strain content that were haploinsufficient or fully deficient for one or both genes. Mice deficient in both genes were born at expected Mendelian ratios and survived to adulthood without apparent deleterious consequence. MFS mice possessing the 129 sequence at the two genes of interest fully recapitulated both the aortic root size and biochemical signaling seen in pure 129 MFS mice (FIGS. 3C, 3D). Furthermore, aortic root size at 6 months was dependent on the number of functional Mmp17 and Map2k6 alleles, with MFS mice lacking both genes having an aortic size that was indistinguishable from that of pure BL6 MFS animals (FIG. 3C). Western blot analysis of the aortic root in 10-month old MFS mice showed that knockout of both Mmp17 and Map2k6 led to attenuation of canonical and noncanonical signaling cascades to values at or below those of BL6 MFS mice (FIG. 3D). Selective knockout of Mmp17 led to an intermediate suppression of these signaling cascades, indicating that the two genes act in an additive manner.

Figure 3E:
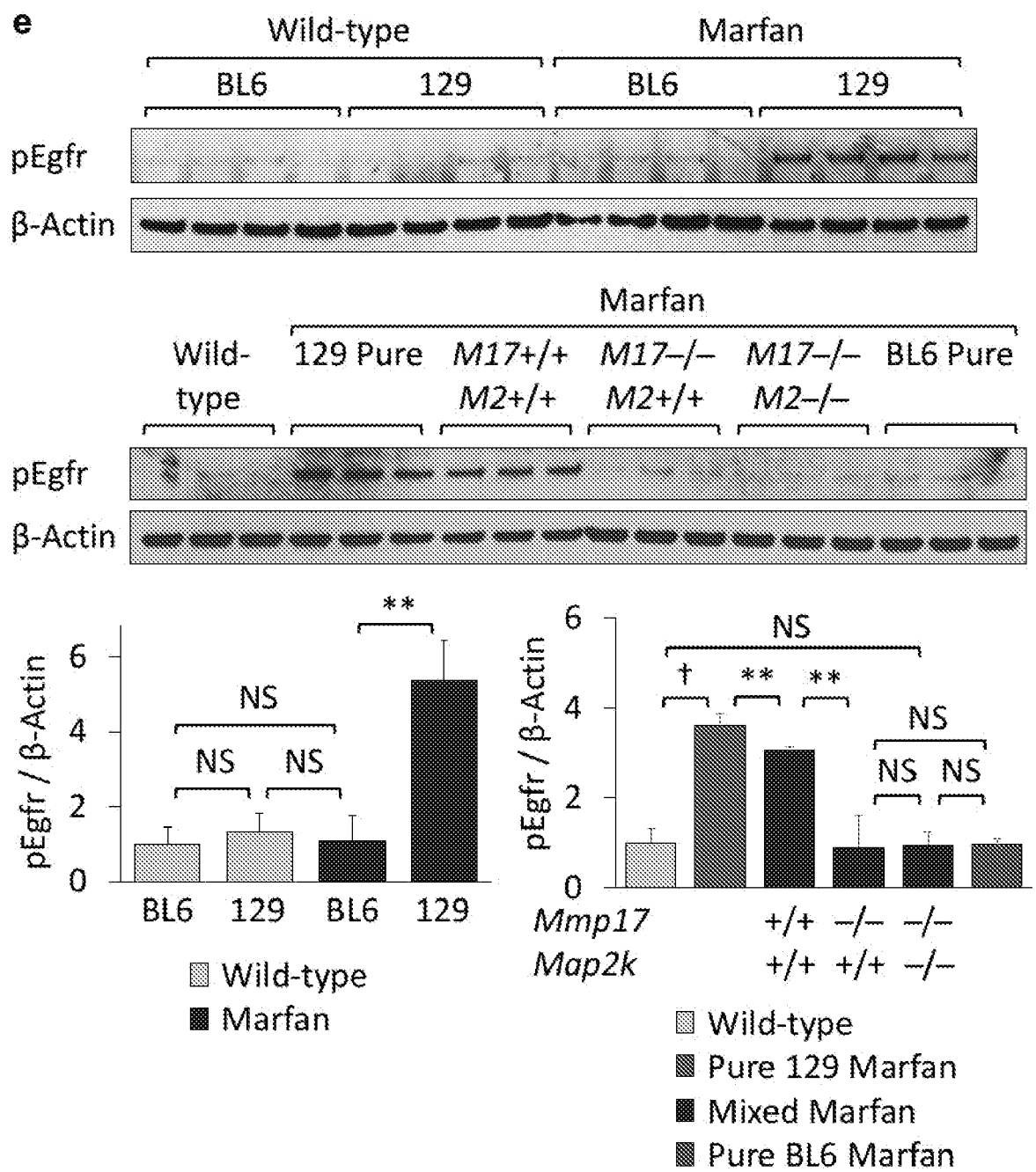
Figure 3F:
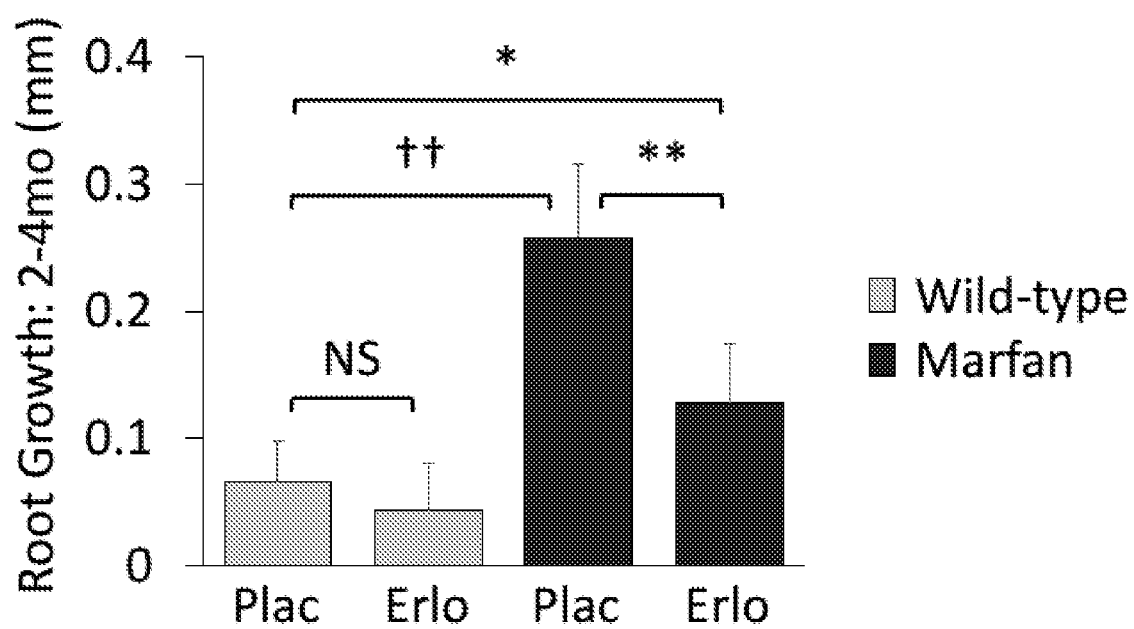
Figure 3G:
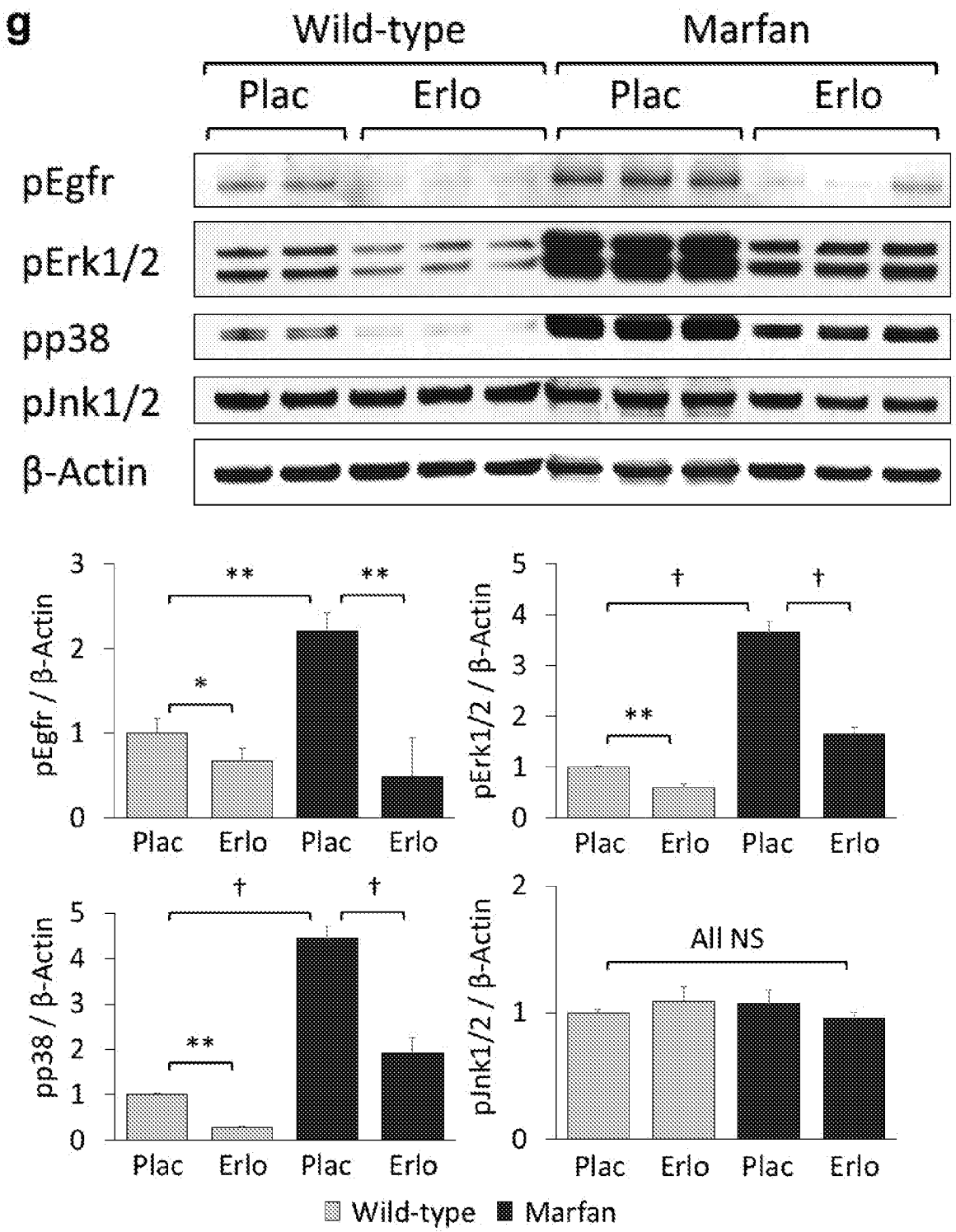

Consistent with prior work showing that Mmp17 can potentiate MAPK signaling by enhancing EGFR activation independent of catalytic activity (Galian C., et al. *J. Biol. Chem.* 287, 16399-409 (2012)), it was found that increased Egfr phosphorylation in the aortic root of 129 MFS mice relative to BL6 MFS animals, which was fully normalized by Mmp17 knockout, was independent of Map2k6 status (FIG. 3E). Furthermore, treatment with the EGFR inhibitor erlotinib abrogated aortic root growth in 129 MFS mice (FIG. 3F), in association with reduced activation of Egfr, Erk1/2, and p38 (FIG. 3G). Hence EGFR inhibition may represent a novel, clinically-available, therapeutic strategy that can help ameliorate aortic growth in MFS.

Figure 4A:
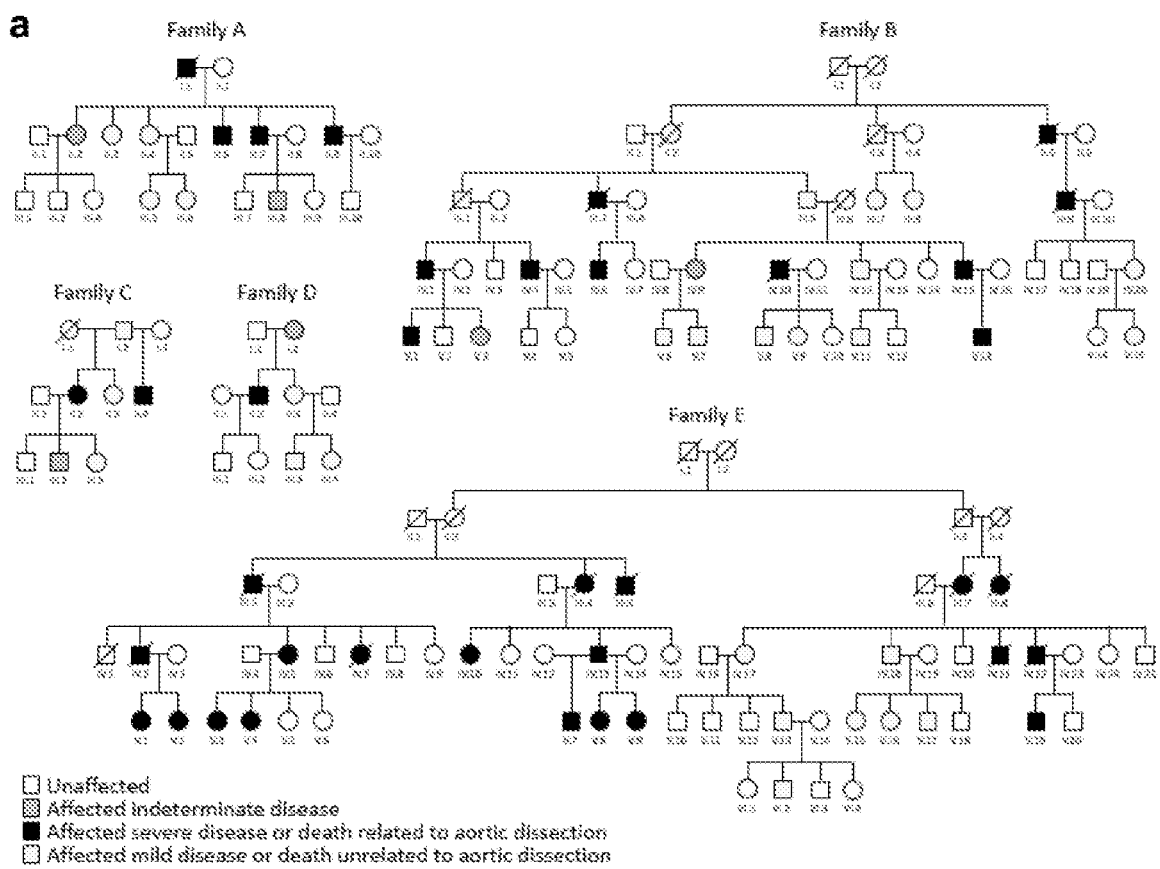
FIGS. 4A-4E show the identification of a modifier locus for aortic aneurysm in MFS patients.
Figure 4B:
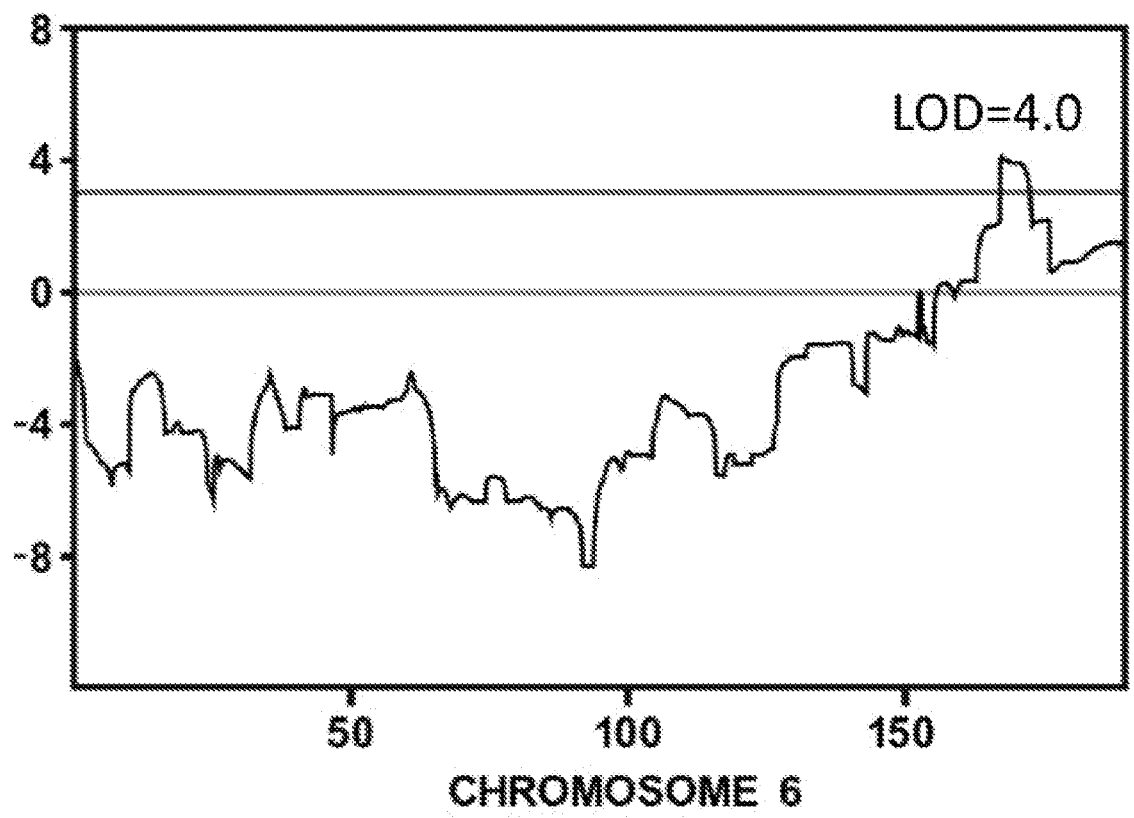
Figure 4C:
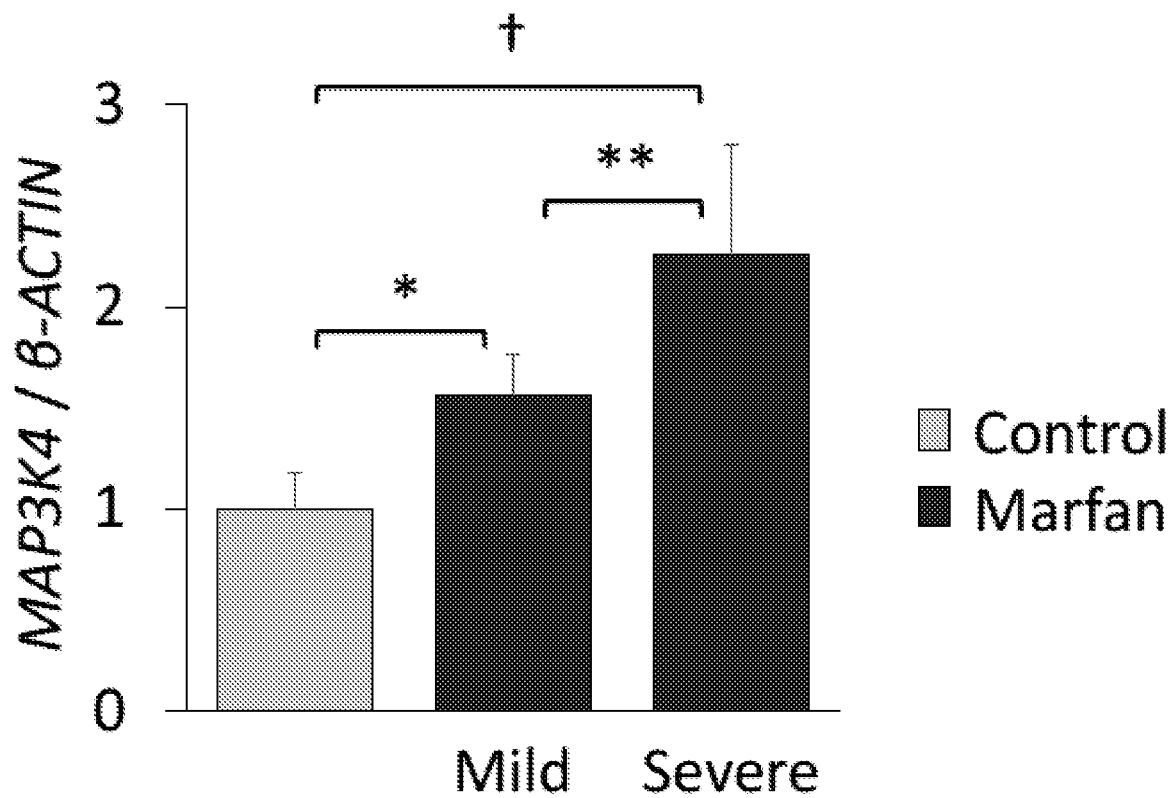

In parallel, 5 MFS families were recruited that showed discrete intrafamilial variation in the severity of vascular disease among age- and gender-matched FBN1 mutation carriers (FIG. 4A). Parametric linkage analysis was performed to identify variation conferring a mild aortic disease phenotype. This revealed a single locus harboring protective genetic variation on chromosome 6 that exceeded the genome-wide significance LOD score of 4.0 (FIG. 4B). While there was no common haplotype across families, all 5 families showed a positive LOD score in this region, with all 20 individuals classified as having mild disease sharing a 3.9 Mb familial haplotype between markers rs676017 and rs6455736. The association between the presence of the protective haplotype and disease status (mild aortic disease 20/20; severe aortic disease 1/18) was statistically significant ($p<0.0001$). Of the 32 genes in this region, MAP3K4 represented the outstanding candidate, based upon the fact that it lies directly upstream and is a direct activator of MAP2K6, one of the two modifier genes identified in MFS mice.

Figure 4D:
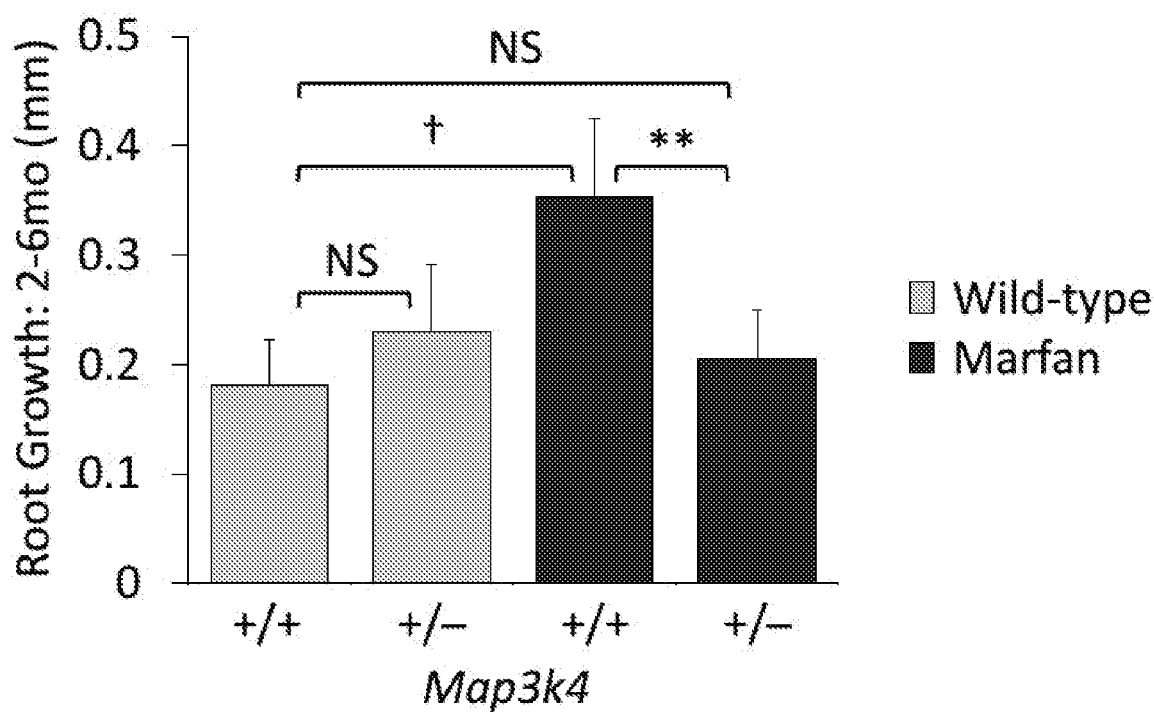
Figure 4E:
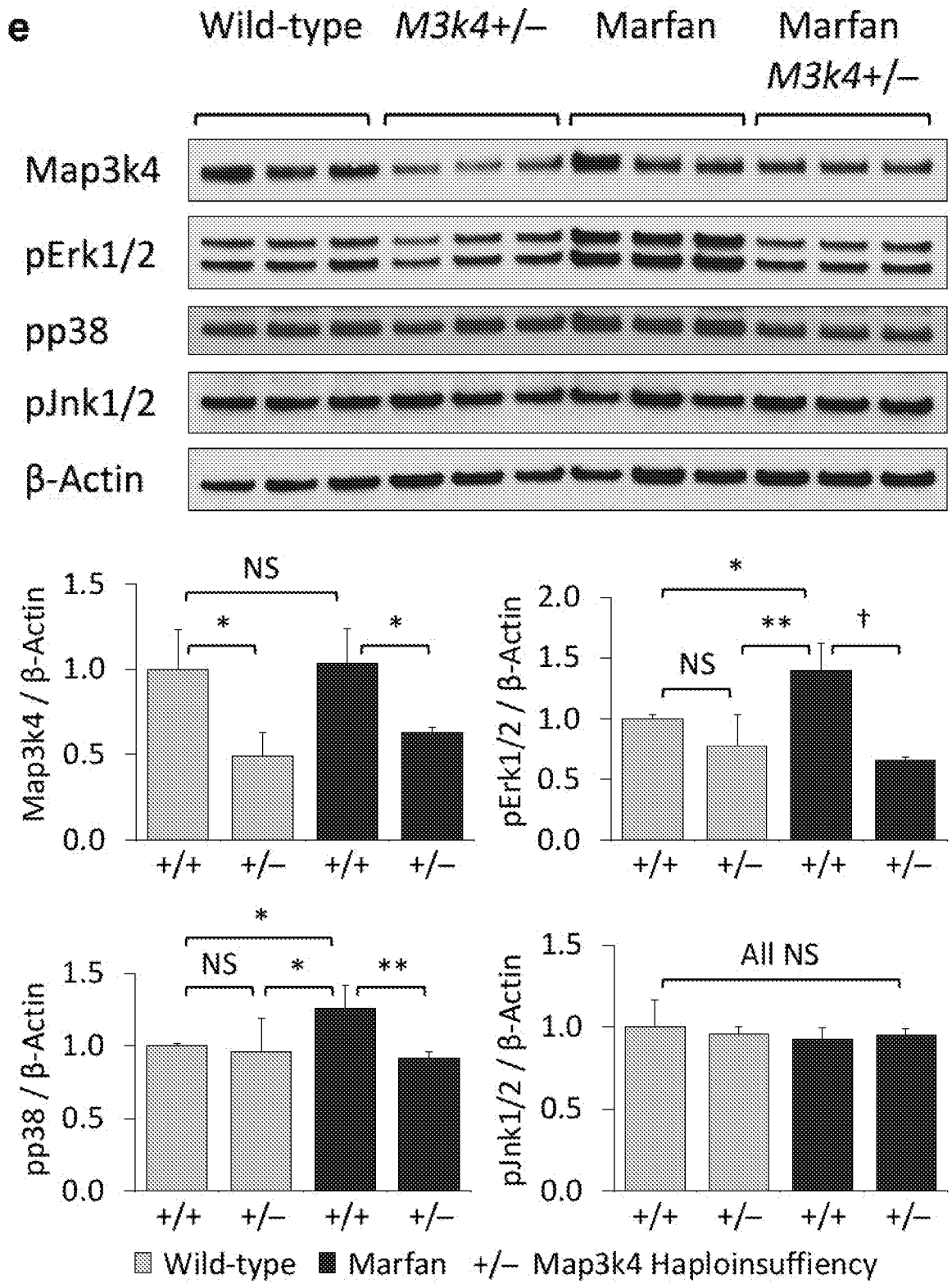

While direct sequencing of all exons, exon/intron boundaries and potential non-coding functional variants from the ENCODE dataset in the 5 MFS pedigrees did not yield a candidate variant in MAP3K4, we did observe a significant reduction in MAP3K4 expression in dermal fibroblasts of patients with mild disease compared to those with severe disease (FIG. 4D). Next, MFS mice to mice haploinsufficient for Map3k4 (Map3k4$^{+/-}$) were bred to test for genetic interaction. Aortic root growth from 2 to 6 months was reduced in MFS mice haploinsufficient for Map3k4, compared to MFS littermates that retained both alleles (FIG. 4D). Western blot analysis of the aortas of 10-month old mice confirmed that Map3k4 levels were reduced in these animals, as was activation of both Erk1/2 and p38 (FIG. 4E).

Taken together, this confluence of discovery-based and hypothesis-driven methodologies has informed disease pathogenesis in MFS and should provide confidence regarding the potential of therapeutic strategies directed against these novel target proteins. It demonstrates the power of harnessing nature's ability to generate phenotypic variability in pathological disease states through modifying genetic variation. It also highlights the utility of using mouse models to inform human disease modifier studies, since the latter can be limited by a paucity of families with discrete intrafamilial phenotypic variation, small pedigrees, allelic heterogeneity at the primary disease locus, and late onset declaration of phenotypic variation. Such issues can be mitigated by concomitant utilization of robust, validated animal models.

A role for EGFR activation in MFS has not been recognized previously; whether this relates to a failed regulatory role of fibrillin-1, or represents a more indirect consequence of events in MFS pathogenesis remains to be determined. Such mechanisms could include EGFR transactivation via known modulators such as TGFβ (Uchiyama-Tanaka Y., et al. *Kidney Int.* 62, 799-808 (2002); Vinals F., *Pouyssegur J. Mol. Cell Biol.* 21, 7218-30 (2001)), and/or Ang-II (Mehta P. K., Griendling K. K. *Am. J. Physiol. Cell Physiol.* 292, C82-97 (2007); Higuchi S., et al. *Clin. Sci.* 112, 417-28 (2007)). Interestingly, Mmp2 and 9 are both activated in MFS mice in an Erk1/2-dependent manner (Xiong W., et al. *Circ. Res.* 110, e92-e101 (2012)), and can also mediate Ang-II-dependent Egfr transactivation and consequent Erk1/2 activation in vascular cells. Furthermore the Efgr inhibitor erlotinib can abrogate Ang-II infusion-mediated TGFβ induction in vascular tissues, all of which suggests that deleterious feedforward loops involving TGFβ, Ang-II and Egfr could influence MFS disease pathogenesis.

This work supports the observations that both Smad2/3 and Erk1/2 signaling cascades are activated in MFS mice, with a direct correlation between the extent of activation of these proteins and phenotypic severity. It also illustrates prominent activation of p38 in this MFS mouse model, recapitulating prior observations in fibrillin-1 null mice (Carta, L. et al. *J. Biol. Chem.* 27, 5630-6 (2009)); this may relate to a hypomorphic Map2k6 allele on the BL6 background previously preventing its robust activation. Interestingly, Ang-II mediated Egfr transactivation has been shown to drive dual Erk1/2 and p38 activation in VSMCs, in the absence of Jnk1/2 upregulation, a direct recapitulation of our findings. In contrast, prior work has suggested that Map3k4 modulates p38 and Jnk1/2 activation without affecting Erk1/2 (Yan W., et al. *J. Mol. Biol.* 275, 25-33 (1998)).

Finally, this work highlights a role for Mmp17 in the modulation of aortic disease in MFS mice. It may achieve this effect through modulation of Egfr, as the data herein evidences.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a human subject having or at risk of developing Marfan Syndrome comprising
    administering to the subject an effective amount of a small molecule inhibitor of epidermal growth factor receptor (EGFR), thereby treating the subject.

2. The method of claim 1, wherein the human subject has or is at risk for an aortic aneurysm or emphysema.

3. The method of claim 1, wherein the human subject has or is at risk for an aneurysm.

4. The method of claim 1, wherein the administered small molecule inhibitor of EGFR is gefitinib, erlotinib, lapatinib, Brigatinib, Afatinib, Neratinib, AZD3759, AZ5104, CL-387785, Canertinib, Poziotinib, Osimertinib, PD168393, CNX-2006, Rociletinib, WZ4002, Pelitinib, AC480, TAK-285, CUDC-101, AEE788, CP-724714, Dacomitinib, AG-490, AST-1306, OSI-420, WHI-P154, WZ3146, WZ8040, Sapitinib, PKI-166, PD158780, AG 1478, PD153035 HCl, Icotinib, Varlitinib, AZD-9291, AG-1478, AG-490, Anlotinib, ARRY-380, BIBX 1382, or BMS-690514.

5. The method of claim 1, wherein the administered small molecule inhibitor of EGFR is gefitinib, lapatinib, canertinib, erlotinib HCL, pelitinib, PKI-166, PD158780, or AG 1478.

6. The method of claim 1, further comprising administering an inhibitor of transforming growth factor β (TGFβ).

7. The method of claim 1, wherein an inhibitor of transforming growth factor β (TGFβ) is not administered to the subject.

* * * * *